US009631227B2

(12) United States Patent
Paul et al.

(10) Patent No.: US 9,631,227 B2
(45) Date of Patent: Apr. 25, 2017

(54) CHEMICALLY MODIFIED LIGASE COFACTORS, DONORS AND ACCEPTORS

(71) Applicant: TriLink BioTechnologies, Inc., San Diego, CA (US)

(72) Inventors: Natasha Paul, Encinitas, CA (US); Sabrina Shore, San Diego, CA (US); Jonathan Shum, Richmond, TX (US); Alexandre Lebedev, San Diego, CA (US); Gerald Zon, San Carlos, CA (US)

(73) Assignee: TRILINK BIOTECHNOLOGIES, INC., San Diego, CA (US)

( * ) Notice: Subject to any disclaimer, the term of this patent is extended or adjusted under 35 U.S.C. 154(b) by 127 days.

(21) Appl. No.: 13/833,600

(22) Filed: Mar. 15, 2013

(65) Prior Publication Data

US 2014/0323354 A1    Oct. 30, 2014

Related U.S. Application Data

(63) Continuation of application No. 12/831,212, filed on Jul. 6, 2010, now Pat. No. 8,728,725.
(Continued)

(51) Int. Cl.
*C40B 40/06* (2006.01)
*C12Q 1/68* (2006.01)
(Continued)

(52) U.S. Cl.
CPC ............ *C12Q 1/6806* (2013.01); *C12N 15/10* (2013.01); *C12N 15/1093* (2013.01); *C12N 15/66* (2013.01)

(58) Field of Classification Search
CPC .............................. C12Q 1/6806; C12N 15/66
(Continued)

(56) References Cited

U.S. PATENT DOCUMENTS 5,508,179 A    4/1996 Wallace et al.
5,593,826 A    1/1997 Fung et al.
(Continued)

FOREIGN PATENT DOCUMENTS

JP    2000-514659 A    11/2000
JP    2007-517497 A    7/2007
(Continued)

OTHER PUBLICATIONS

Kwano, M. et al., "Reduction of non-insert sequence reads by dimer eliminator LNA oligonucleotide for small RNA deep sequencing," BioTechniques, 2010, vol. 49, pp. 751-755 (abstract).
(Continued)

*Primary Examiner* — Jezia Riley
(74) *Attorney, Agent, or Firm* — Kilpatrick Townsend & Stockton LLP

(57) ABSTRACT

Provided herein are methods for ligation of polynucleotides containing modified ligation components, particularly modified ligase cofactors, modified acceptors and modified donors. The methods readily applied to ligation-based assays for detection of a nucleic acid sequence where the use of the modified cofactor improves discrimination between matched and mismatched templates. Furthermore, the use of the modified ligation components reduces or eliminates the ligation in the absence of nucleic acid template. In addition, methods are applied to the preparation of nucleic acid libraries using modified acceptor probes and modified donor probes that reduce or eliminate probe dimerization during the ligation process.

27 Claims, 22 Drawing Sheets

Related U.S. Application Data

(60) Provisional application No. 61/223,364, filed on Jul. 6, 2009.

(51) Int. Cl.
  *C12N 15/10* (2006.01)
  *C12N 15/66* (2006.01)

(58) Field of Classification Search
  USPC .......................................... 506/26; 422/430
  See application file for complete search history.

(56) References Cited

U.S. PATENT DOCUMENTS

| | | | |
|---|---|---|---|
| 5,935,788 | A | 8/1999 | Burmer et al. |
| 6,110,710 | A | 8/2000 | Smith et al. |
| 6,297,016 | B1 | 10/2001 | Egholm et al. |
| 6,312,892 | B1 | 11/2001 | Barany et al. |
| 6,635,425 | B2 | 10/2003 | Bandaru et al. |
| 6,762,298 | B2 | 7/2004 | Beaucage et al. |
| 6,811,986 | B2 | 11/2004 | Bandaru et al. |
| 6,949,370 | B1 | 9/2005 | Barany et al. |
| 2004/0197791 | A1 | 10/2004 | Makarov et al. |
| 2005/0037346 | A1 | 2/2005 | Barany et al. |
| 2006/0292568 | A1 | 12/2006 | Brachet et al. |
| 2007/0031865 | A1 | 2/2007 | Willoughby |
| 2007/0269805 | A1 | 11/2007 | Hogers |
| 2009/0328244 | A1 | 12/2009 | Chesnut et al. |
| 2011/0008788 | A1 | 1/2011 | Paul et al. |

FOREIGN PATENT DOCUMENTS

| | | |
|---|---|---|
| WO | 98/03673 A1 | 1/1998 |
| WO | 2005/021794 A1 | 3/2005 |
| WO | 2011005762 A1 | 1/2011 |
| WO | WO 2012/094343 A1 | 6/2012 |
| WO | 2012094343 A1 | 7/2012 |

OTHER PUBLICATIONS

International Search Report and Written Opinion dated Aug. 11, 2014, issued in International Application No. PCT/US2014/029612.
EP14764953.7, "Extended European Search Report", Oct. 27, 2016, 5 pages.
Antson, et al, PCR-generated padlock probes detect signel nucleotide variation in genomic DNA, Nucleic Acids Res, 28:e58 (2000).
Ausubel, et al., "Anaysis of Glycosaminoglycans with Polysaccharide Lyases", Current Protocols in Molecular Biology, (1994), 2:17-32.
Barringer, et al, Blunt-end and single-strand ligations by *Escherichia coli* ligase: influence on an in vitro amplification scheme, Gene, 89:117-122 (1990).
Belford, et al, Multiple Nucleotide Cofactor Use by Yeast Ligase in tRNA Splicing, J Biol Chern, 268:2444-2450 (1993}.
Gao, W., Recent developments in ligase-mediated amplification and detection, Trends Biotechnology, 22:38-44 (2004).
Cheng, et al, Multiplexed profiling of candidate genes for CpG island methylation status using a flexible PCR/LDR/Universal Array assay, Genome Res, 16:282-289 (2006).
Cherepanov, et al, Dynamic mechanism of nick recognition by DNA ligase, Eur J Biochem, 269:5993-5999 (2002).
Crey-Desbiolles, et. al., Hybridization properties and enzymatic replication of oligonucleotides containing the photocleavable 7-nitroindole base analog, Nucleic Acids Res. 33:1532 131543 (2005).
Doherty, et al, Bacteriophage T7 DNA Ligase, J Biol Chern, 271:11083-11089 (1996).
Extended European Search Report dated Oct. 2, 2012 for European Application EP10797720.9, 5 pages.
European Office Action dated May 31, 2013 for European Application 10797720.9, 3 pages.
Feng, et al, Effects of deletion and site-directed mutations on ligation steps of NAD+-dependent DNA ligase: a biochemical analysis of BRCA1 C-terminal domain, Biochemistry, 43:12648-12659 (2004).
Feng, et al, Mutational analysis of bacterial NAD dependent DNA ligase, Acta Biochim Biophys Sin, 39( 8 ):608-616 (2007).
Hill, et. al., Polymerase recognition of synthetic oligodeoxyribonucleotides incorporating degenerate pyrimidine and purine bases, Proc Natl Acad Sci US A, 95: 4258 134263 (1998).
Ho, et al, Characterization of an ATP-Dependent DNA Ligase Encoded by Chlorella Virus PBCV-1, J Viral, 71:1931-1937 (1997).
International Search Report dated Sep. 20, 2010 for International Application No. PCT/US2010/041069, 3 pages.
Jeon, et al, Mutational analyses of the thermostable NAD+-dependent DNA ligase from Thermus filiformis, FEMS Microbiology Lett, 237:111-118 (2004).
Kim Joohoon et al: "Profiling the selectivity of DNA ligases in an array format with mass spectrometry",Nucleic Acids Research,vol. 38, No. 1, Jan. 2010 (Jan. 2010), ISSN: 0305-1048.
Kincaid, et al., Exploration of factors driving incorporation of unnatural dNTPS into DNA by Klenow fragment (DNA polymerase I) and DNA polymerase ex, Nucleic Acids Res., 33:2620-2628 (2005).
Kuhn, et al., Template-independent ligation of single-stranded DNA by T4 DNA ligase, FEBS Journal, 272:5991-6000 (2005).
Lai, et al, Biochemical characterization of an ATP-dependent DNA ligase from the hyperthermophilic crenarachaeon Sulfolobus shibatae, Extremophiles, 6:469-477 (2002).
Landegren, et al., A Ligase-Mediated Gene Detection Technique, Science, 241:1077-1080 (1988).
Lim, et al, Mutational analyses of Aquifex pyrophilus DNA ligase define essential domains for selfadenylation and DNA binding activity, Arch Biochem Biophys, 388:253-260 (2001).
Loakes, D., The applications of universal DNA base analogues, Nucleic Acids Res., 29:2437-132447 (2001).
Luo, et al, Identification of essential residues in Thermus thermophilus DNA ligase, Nucleic Acids Res, 24:3079-3085 (1996).
Luo J et al: "Improving the fidelity of Thermus thermophilus DNA ligase",Nucleic Acids Research, Oxford University Press,Surrey, GB, vol. 24, No. 14, Aug. 1, 1996 (Aug. 1, 1996 ), pp. 3071-3078, XP002141352, ISSN: 0305-1048, DOI: 10.1 093/NAR/24.15.3071.
Montecucco, et al, Use of ATP, dATP and their α-thio derivatives to study DNA ligase adenylation, Biochem J, 271:265-268 (1990).
Mueller, et al, In vivo footprinting of a muscle specific enhancer by ligation mediated PCR, Science, 246:780-786 (1989).
Non-Final Office Action mailed on Sep. 27, 2012 for U.S. Appl. No. 12/831,212, 7 pages.
Pfeifer, et al, Genomic sequencing by Ligation-Mediated PCR, Molecular Biotechnology, 5:281-288 (1996).
Preparata, et al., DNA Sequencing by Hybridization Using Semi-Degenerate Bases, J. Comput.Biol. 11: 753-765 (2004).
Raae, et al, Effect of ATP analogues on T4 polynucleotide ligase, Biochem Biophys Res Commun,81:24-27 (1978).
Sambrook, et al, Introduction of Recombinant Vectors into Mammalian Cells, Molecular Cloning: A Laboratory Manual, Second Edition, 16.30-16.37 (1989).
Showalter, et al, Mechanistic comparison of high-fidelity and error-prone DNA polymerases and ligases involved in DNA repair, Chem Rev, 106:340-360 (2006).
Shuman, S., Vaccinia virus DNA ligase: specificity, fidelity, and inhibition, Biochemistry, 34:16138-16147 (1995).
Sriskanda, et al, Characterization of an ATP-dependent DNA ligase from the thermophilic archaeon *Methanobacterium thermoautotrophicum*, Nucleic Acids Res, 28:2221-2228 (2000).
Tong, et al, Biochemical properties of a high fidelity DNA ligase from *Thermus* species AK16D, Nucleic Acids Res, 27:788-794 (1999).
Western, et al, A novel DNA joining activity catalyzed by T4 DNA ligase, Nucleic Acids Res, 19:809-813 (1991).
Wiedmann, et al., Ligase chain reaction (LCR)-overview and applications. PCR Methods Appl. 3:551-564 (1994).

(56) References Cited

OTHER PUBLICATIONS

Zirvi M et al: "Improved fidelity of thermostable ligases for detection of microsatellite repeat sequences using nucleoside analogs", Nucleic Acids Research, Oxford University Press, Surrey, GB, vol. 27, No. 24, Dec. 15, 1999 (Dec. 15, 1999), p. e41, XP002246189, ISSN: 0305-1048.

T-A Match

| | | Modified ATP Cofactor | | | | | | |
|---|---|---|---|---|---|---|---|---|
| | | ATP | 2'-dATP | alpha-thio-ATP | 2'-amino-2'-dATP | 2-amino-2'-dATP | 3'-amino ddATP | 2-amino ATP |
| Modified Acceptor Probe | No Modification | 1.18 | 0.75 | 0.63 | 0.61 | 0.66 | 0.99 | 0.50 |
| | PS (X1) | 0.92 | 0.45 | 0.65 | 0.64 | 0.71 | 0.94 | 0.61 |
| | PMe (X1) | 1.07 | 0.19 | 0.49 | 0.48 | 0.47 | 1.22 | 0.20 |
| | PMe (X2) | 0.74 | 0.07 | 0.64 | 0.25 | 0.32 | 0.72 | 0.42 |
| | Ome (Y1) | 0.80 | 0.08 | 0.88 | 0.17 | 0.23 | 0.90 | 0.38 |
| | Ome (Y1) | 0.94 | 0.21 | 0.87 | 0.38 | 0.47 | 1.11 | 0.16 |

Key
- > 0.85
- 0.70 to 0.85
- 0 to 0.70

T-C Mismatch

| | | Modified ATP Cofactor | | | | | | |
|---|---|---|---|---|---|---|---|---|
| | | ATP | 2'-dATP | alpha-thio-ATP | 2'-amino-2'-dATP | 2-amino-2'-dATP | 3'-amino ddATP | 2-amino ATP |
| Modified Acceptor Probe | No modification | 0.11 | 0.04 | 0.05 | 0.10 | 0.07 | 0.07 | 0.10 |
| | PS (X1) | 0.19 | 0.06 | 0.06 | 0.11 | 0.08 | 0.08 | 0.13 |
| | PMe (X1) | 0.00 | 0.01 | 0.00 | 0.01 | 0.00 | 0.00 | 0.00 |
| | PMe (X2) | 0.05 | 0.02 | 0.01 | 0.04 | 0.03 | 0.03 | 0.02 |
| | Ome (Y1) | 0.05 | 0.01 | 0.01 | 0.07 | 0.04 | 0.04 | 0.02 |
| | Ome (Y1) | 0.00 | 0.00 | 0.02 | 0.00 | 0.01 | 0.01 | 0.00 |

Key
- 0.0 to 0.01
- 0.01 to 0.10
- 0.10 to 1.00

Figure 8

SEQUENCE LISTING

```
<160> NUMBER OF SEQ ID NOS: 58

<210> SEQ ID NO 1
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 1
tagcgtcttg atagtctcgt g                                            21

<210> SEQ ID NO 2
<211> LENGTH: 21
<212> TYPE: DNA
<213> ORGANISM: Artificial Sequence
<220> FEATURE:
<223> OTHER INFORMATION: Synthetic polynucleotide
```

-continued

```
<400> SEQUENCE: 2
gtaccagtcg cctagaatac t                                              21

<210> SEQ ID NO 3
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 3
tagcgtcttg atagtctcgt gccctgttcc agcgtcggtg ttgcgtt                  47

<210> SEQ ID NO 4
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 4
tagcgtcttg atagtctcgt gccctgttcc agcgtcggtg ttgcgtg                  47

<210> SEQ ID NO 5
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 5
tagcgtcttg atagtctcgt gccctgttcc agcgtcggtg ttgcgtc                  47

<210> SEQ ID NO 6
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 6
tagcgtcttg atagtctcgt gccctgttcc agcgtcggtg ttgcgta                  47

<210> SEQ ID NO 7
<211> LENGTH: 51
<212> TYPE: DNA
<213> ORGANISM: Artificial Sequence
<220> FEATURE:
<223> OTHER INFORMATION: Synthetic polynucleotide

<400> SEQUENCE: 7
agttgtcata gtttgatcct ctagtctggg agtattctag gcgactggta c             51

<210> SEQ ID NO 8
<211> LENGTH: 59
<212> TYPE: DNA
<213> ORGANISM: Artificial Sequence
<220> FEATURE:
<223> OTHER INFORMATION: Synthetic polynucleotide

<400> SEQUENCE: 8
cccagactag aggatcaaac tatgacaact aacgcaacac cgcagacgct ggaacaggg     59

<210> SEQ ID NO 9
<211> LENGTH: 26
```

```
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: 5'-terminal modified with NH2 adapter probe

<400> SEQUENCE: 9
guucagaguu cuacaguccg acgauc                                    26

<210> SEQ ID NO 10
<211> LENGTH: 26
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: 5'-terminal modified with NH2 adapter probe
<220> FEATURE:
<221> NAME/KEY: misc_feature
<222> LOCATION: (25)..(25)
<223> OTHER INFORMATION: Residue modified with phosphorothioate

<400> SEQUENCE: 10
guucagaguu cuacaguccg acgauc                                    26

<210> SEQ ID NO 11
<211> LENGTH: 26
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: 5'-terminal modified with NH2 adapter probe
<220> FEATURE:
<221> NAME/KEY: misc_feature
<222> LOCATION: (24)..(24)
<223> OTHER INFORMATION: Residue modified with phosphorothioate

<400> SEQUENCE: 11
guucagaguu cuacaguccg acgauc                                    26

<210> SEQ ID NO 12
<211> LENGTH: 26
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: 5'-terminal modified with NH2 adapter probe
<220> FEATURE:
<221> NAME/KEY: misc_feature
<222> LOCATION: (25)..(25)
<223> OTHER INFORMATION: Resdidue is T modified with methylphosphonate

<400> SEQUENCE: 12
guucagaguu cuacaguccg acgatc                                    26

<210> SEQ ID NO 13
<211> LENGTH: 26
<212> TYPE: DNA
<213> ORGANISM: Artificial Sequence
<220> FEATURE:
```

```
<223> OTHER INFORMATION: Synthetic polynucleotide
<220> FEATURE:
<221> NAME/KEY: misc_feature
<222> LOCATION: (1)..(1)
<223> OTHER INFORMATION: 5'-terminal modified with NH2 adapter probe
<220> FEATURE:
<221> NAME/KEY: misc_feature
<222> LOCATION: (24)..(24)
<223> OTHER INFORMATION: Residue is deoxy A modified with
      methylphosphonate

<400> SEQUENCE: 13
guucagaguu cuacaguccg acgauc                                           26

<210> SEQ ID NO 14
<211> LENGTH: 26
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: 5'-terminal modified with NH2 adapter probe
<220> FEATURE:
<221> NAME/KEY: misc_feature
<222> LOCATION: (26)..(26)
<223> OTHER INFORMATION: Residue is modified with 2-'methoxy

<400> SEQUENCE: 14
guucagaguu cuacaguccg acgauc                                           26

<210> SEQ ID NO 15
<211> LENGTH: 26
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: 5'-terminal modified with NH2 adapter probe
<220> FEATURE:
<221> NAME/KEY: misc_feature
<222> LOCATION: (25)..(25)
<223> OTHER INFORMATION: Residue is modified with 2'-methoxy

<400> SEQUENCE: 15
guucagaguu cuacaguccg acgauc                                           26

<210> SEQ ID NO 16
<211> LENGTH: 26
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: 5'-terminal modified with NH2 adapter probe
<220> FEATURE:
<221> NAME/KEY: misc_feature
<222> LOCATION: (24)..(24)
<223> OTHER INFORMATION: Residue is modified with 2'-methoxy

<400> SEQUENCE: 16
guucagaguu cuacaguccg acgauc                                           26

<210> SEQ ID NO 17
<211> LENGTH: 26
<212> TYPE: RNA
```

```
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: 5'-terminal modified with NH2 adapter probe
<220> FEATURE:
<221> NAME/KEY: misc_feature
<222> LOCATION: (26)..(26)
<223> OTHER INFORMATION: Residue is modified with 2'-fluoro

<400> SEQUENCE: 17
guucagaguu cuacaguccg acgauc                                              26

<210> SEQ ID NO 18
<211> LENGTH: 26
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: 5'-terminal modified with NH2 adapter probe
<220> FEATURE:
<221> NAME/KEY: misc_feature
<222> LOCATION: (25)..(25)
<223> OTHER INFORMATION: Residue is modified with 2'-fluoro

<400> SEQUENCE: 18
guucagaguu cuacaguccg acgauc                                              26

<210> SEQ ID NO 19
<211> LENGTH: 26
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: 5'-terminal modified with NH2 adapter probe
<220> FEATURE:
<221> NAME/KEY: misc_feature
<222> LOCATION: (24)..(24)
<223> OTHER INFORMATION: Residue is modified with 2'-fluoro

<400> SEQUENCE: 19
guucagaguu cuacaguccg acgauc                                              26

<210> SEQ ID NO 20
<211> LENGTH: 51
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (51)..(51)
<223> OTHER INFORMATION: Residue is dideoxy C

<400> SEQUENCE: 20
agttgtcata gtttgatcct ctagtctggg agtattctag gcgactggta c                  51

<210> SEQ ID NO 21
<211> LENGTH: 51
<212> TYPE: DNA
<213> ORGANISM: Artificial Sequence
<220> FEATURE:
<223> OTHER INFORMATION: Synthetic polynucleotide
```

```
<220> FEATURE:
<221> NAME/KEY: misc_feature
<222> LOCATION: (1)..(1)
<223> OTHER INFORMATION: Residue modified with phosphorothioate
<220> FEATURE:
<221> NAME/KEY: misc_feature
<222> LOCATION: (51)..(51)
<223> OTHER INFORMATION: Residue is dideoxy C

<400> SEQUENCE: 21
agttgtcata gtttgatcct ctagtctggg agtattctag gcgactggta c        51

<210> SEQ ID NO 22
<211> LENGTH: 51
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (2)..(2)
<223> OTHER INFORMATION: Residue modified with phosphorothioate
<220> FEATURE:
<221> NAME/KEY: misc_feature
<222> LOCATION: (51)..(51)
<223> OTHER INFORMATION: Residue is dideoxy C

<400> SEQUENCE: 22
agttgtcata gtttgatcct ctagtctggg agtattctag gcgactggta c        51

<210> SEQ ID NO 23
<211> LENGTH: 51
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Residue is modified with methylphosphonate
<220> FEATURE:
<221> NAME/KEY: misc_feature
<222> LOCATION: (51)..(51)
<223> OTHER INFORMATION: Residue is dideoxy C

<400> SEQUENCE: 23
agttgtcata gtttgatcct ctagtctggg agtattctag gcgactggta c        51

<210> SEQ ID NO 24
<211> LENGTH: 51
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (2)..(2)
<223> OTHER INFORMATION: Residue modified with methylphosphonate
<220> FEATURE:
<221> NAME/KEY: misc_feature
<222> LOCATION: (51)..(51)
<223> OTHER INFORMATION: Residue is dideoxy C

<400> SEQUENCE: 24
agttgtcata gtttgatcct ctagtctggg agtattctag gcgactggta c        51

<210> SEQ ID NO 25
<211> LENGTH: 51
<212> TYPE: DNA
<213> ORGANISM: Artificial Sequence
<220> FEATURE:
```

```
<223> OTHER INFORMATION: Synthetic polynucleotide
<220> FEATURE:
<221> NAME/KEY: misc_feature
<222> LOCATION: (1)..(1)
<223> OTHER INFORMATION: Residue is 2-'methoxy A
<220> FEATURE:
<221> NAME/KEY: misc_feature
<222> LOCATION: (51)..(51)
<223> OTHER INFORMATION: Residue is dideoxy C

<400> SEQUENCE: 25
agttgtcata gtttgatcct ctagtctggg agtattctag gcgactggta c          51

<210> SEQ ID NO 26
<211> LENGTH: 51
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (2)..(2)
<223> OTHER INFORMATION: Residue ix 2'-methoxy G
<220> FEATURE:
<221> NAME/KEY: misc_feature
<222> LOCATION: (51)..(51)
<223> OTHER INFORMATION: Residue ix dideoxy C

<400> SEQUENCE: 26
agttgtcata gtttgatcct ctagtctggg agtattctag gcgactggta c          51

<210> SEQ ID NO 27
<211> LENGTH: 51
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (3)..(3)
<223> OTHER INFORMATION: Residue is 2'-methoxy U
<220> FEATURE:
<221> NAME/KEY: misc_feature
<222> LOCATION: (51)..(51)
<223> OTHER INFORMATION: Residue is dideoxy C

<400> SEQUENCE: 27
agutgtcata gtttgatcct ctagtctggg agtattctag gcgactggta c          51

<210> SEQ ID NO 28
<211> LENGTH: 51
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Residue is 2'-fluoro A
<220> FEATURE:
<221> NAME/KEY: misc_feature
<222> LOCATION: (51)..(51)
<223> OTHER INFORMATION: Residue is dideoxy C

<400> SEQUENCE: 28
agttgtcata gtttgatcct ctagtctggg agtattctag gcgactggta c          51

<210> SEQ ID NO 29
<211> LENGTH: 51
<212> TYPE: DNA
<213> ORGANISM: Artificial Sequence
```

```
<220> FEATURE:
<223> OTHER INFORMATION: Synthetic polynucleotide
<220> FEATURE:
<221> NAME/KEY: misc_feature
<222> LOCATION: (2)..(2)
<223> OTHER INFORMATION: Residue is 2'-fluoro G
<220> FEATURE:
<221> NAME/KEY: misc_feature
<222> LOCATION: (51)..(51)
<223> OTHER INFORMATION: Residue is dideoxy C

<400> SEQUENCE: 29
agttgtcata gtttgatcct ctagtctggg agtattctag gcgactggta c         51

<210> SEQ ID NO 30
<211> LENGTH: 51
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (3)..(3)
<223> OTHER INFORMATION: Residue is 2'-fluoro U
<220> FEATURE:
<221> NAME/KEY: misc_feature
<222> LOCATION: (51)..(51)
<223> OTHER INFORMATION: Residue is dideoxy U

<400> SEQUENCE: 30
agutgtcata gtttgatcct ctagtctggg agtattctag gcgactggta c         51

<210> SEQ ID NO 31
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 31
uggaguguga caauguguu ug                                          22

<210> SEQ ID NO 32
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 32
ccaguauuaa cugugcugcu ga                                         22

<210> SEQ ID NO 33
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 33
aguucuucag uggcaagcuu ua                                         22

<210> SEQ ID NO 34
<211> LENGTH: 21
<212> TYPE: RNA
<213> ORGANISM: Artificial Sequence
<220> FEATURE:
<223> OTHER INFORMATION: Synthetic polynucleotide
```

-continued

```
<400> SEQUENCE: 34
ugagaugaag cacuguagcu c                                              21

<210> SEQ ID NO 35
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 35
acggguuagg cucuugggag cu                                             22

<210> SEQ ID NO 36
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 36
caacaaauca cagucugcca ua                                             22

<210> SEQ ID NO 37
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 37
caagcucgcu ucuaugdguc ug                                             22

<210> SEQ ID NO 38
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 38
caacaaauca cagucugcca ua                                             22

<210> SEQ ID NO 39
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 39
aaaccguuac cauuacugag uu                                             22

<210> SEQ ID NO 40
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 40
uguaaacauc cccgacugga ag                                             22

<210> SEQ ID NO 41
<211> LENGTH: 22
```

```
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (22)..(22)
<223> OTHER INFORMATION: Residue modified with C3 propyl spacer

<400> SEQUENCE: 41
agttgtcata gtttgatcct ct                                             22

<210> SEQ ID NO 42
<211> LENGTH: 23
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (23)..(23)
<223> OTHER INFORMATION: Residue modified with C3 propyl spacer

<400> SEQUENCE: 42
aagttgtcat agtttgatcc tct                                            23

<210> SEQ ID NO 43
<211> LENGTH: 27
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: 5'-terminal modified with NH2 adapter probe

<400> SEQUENCE: 43
tttgtagagg atcaaactat gacaact                                        27

<210> SEQ ID NO 44
<211> LENGTH: 27
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: 5'-terminal modified with NH2 adapter probe
<220> FEATURE:
<221> NAME/KEY: misc_feature
<222> LOCATION: (27)..(27)
<223> OTHER INFORMATION: Residue is 2'-fluoro U

<400> SEQUENCE: 44
tttgtagagg atcaaactat gacaacu                                        27

<210> SEQ ID NO 45
<211> LENGTH: 27
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: 5'-terminal modified with NH2 adapter probe
<220> FEATURE:
<221> NAME/KEY: misc_feature
<222> LOCATION: (26)..(26)
```

<223> OTHER INFORMATION: Residue is 2'-fluoro C

<400> SEQUENCE: 45
tttgtagagg atcaaactat gacaact                                              27

<210> SEQ ID NO 46
<211> LENGTH: 27
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: 5'-terminal modified with NH2 adapter probe
<220> FEATURE:
<221> NAME/KEY: misc_feature
<222> LOCATION: (25)..(25)
<223> OTHER INFORMATION: Residue is 2-'fluoro A

<400> SEQUENCE: 46
tttgtagagg atcaaactat gacaact                                              27

<210> SEQ ID NO 47
<211> LENGTH: 27
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: 5'-terminal modified with NH2 adapter probe
<220> FEATURE:
<221> NAME/KEY: misc_feature
<222> LOCATION: (27)..(27)
<223> OTHER INFORMATION: Residue is U modified with 2'-F-ANA
      (2'-deoxy-2'-fluoro-beta-D-arabinonucleic acid)

<400> SEQUENCE: 47
tttgtagagg atcaaactat gacaacu                                              27

<210> SEQ ID NO 48
<211> LENGTH: 27
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: 5'-terminal modified with NH2 adapter probe
<220> FEATURE:
<221> NAME/KEY: misc_feature
<222> LOCATION: (26)..(26)
<223> OTHER INFORMATION: Residue is C modified with 2'-F-ANA
      (2'-deoxy-2'-fluoro-beta-D-arabinonucleic acid)

<400> SEQUENCE: 48
tttgtagagg atcaaactat gacaact                                              27

<210> SEQ ID NO 49
<211> LENGTH: 27
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: 5'-terminal modified with NH2 adapter probe

```
<220> FEATURE:
<221> NAME/KEY: misc_feature
<222> LOCATION: (25)..(25)
<223> OTHER INFORMATION: Residue is A modified with 2'-F-ANA
      (2'-deoxy-2'-fluoro-beta-D-arabinonucleic acid)

<400> SEQUENCE: 49
tttgtagagg atcaaactat gacaact                                           27

<210> SEQ ID NO 50
<211> LENGTH: 27
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: 5'-terminal modified with NH2 adapter probe
<220> FEATURE:
<221> NAME/KEY: misc_feature
<222> LOCATION: (27)..(27)
<223> OTHER INFORMATION: Residue is 2'-methoxy U

<400> SEQUENCE: 50
tttgtagagg atcaaactat gacaacu                                           27

<210> SEQ ID NO 51
<211> LENGTH: 27
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: 5'-terminal modified with NH2 adapter probe
<220> FEATURE:
<221> NAME/KEY: misc_feature
<222> LOCATION: (26)..(26)
<223> OTHER INFORMATION: Residue is 2'-methoxy C

<400> SEQUENCE: 51
tttgtagagg atcaaactat gacaact                                           27

<210> SEQ ID NO 52
<211> LENGTH: 27
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: 5'-terminal modified with NH2 adapter probe
<220> FEATURE:
<221> NAME/KEY: misc_feature
<222> LOCATION: (25)..(25)
<223> OTHER INFORMATION: Residue is 2'-methoxy A

<400> SEQUENCE: 52
tttgtagagg atcaaactat gacaact                                           27

<210> SEQ ID NO 53
<211> LENGTH: 27
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
```

```
<222> LOCATION: (1)..(1)
<223> OTHER INFORMATION: 5'-terminal modified with NH2 adapter probe
<220> FEATURE:
<221> NAME/KEY: misc_feature
<222> LOCATION: (26)..(26)
<223> OTHER INFORMATION: Residue modified with methylphosphonate

<400> SEQUENCE: 53
tttgtagagg atcaaactat gacaact                                              27

<210> SEQ ID NO 54
<211> LENGTH: 27
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: 5'-terminal modified with NH2 adapter probe
<220> FEATURE:
<221> NAME/KEY: misc_feature
<222> LOCATION: (25)..(25)
<223> OTHER INFORMATION: Residue modified with methylphosphonate

<400> SEQUENCE: 54
tttgtagagg atcaaactat gacaact                                              27

<210> SEQ ID NO 55
<211> LENGTH: 27
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: 5'-terminal modified with NH2 adapter probe
<220> FEATURE:
<221> NAME/KEY: misc_feature
<222> LOCATION: (26)..(26)
<223> OTHER INFORMATION: Residue modified with phosphorothioate

<400> SEQUENCE: 55
tttgtagagg atcaaactat gacaact                                              27

<210> SEQ ID NO 56
<211> LENGTH: 27
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: 5'-terminal modified with NH2 adapter probe
<220> FEATURE:
<221> NAME/KEY: misc_feature
<222> LOCATION: (25)..(25)
<223> OTHER INFORMATION: Residue modified with phosphorothioate

<400> SEQUENCE: 56
```

```
tttgtagagg atcaaactat gacaact                                              27

<210> SEQ ID NO 57
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 57
cuauacgacc ugcugccuuu cu                                                   22

<210> SEQ ID NO 58
<211> LENGTH: 17
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Residue modified with FAM

<400> SEQUENCE: 58
atagtctcgt gccctgc                                                         17
```

CHEMICALLY MODIFIED LIGASE COFACTORS, DONORS AND ACCEPTORS

CROSS-REFERENCE TO RELATED APPLICATION

This patent application is a continuation in part of U.S. patent application Ser. No. 12/831,212, entitled "Chemically Modified Ligas Cofactors, Donors and Acceptors," filed Jul. 6, 2010, which claims priority to U.S. Provisional Patent Application No. 61/223,364, entitled "Chemically Modified Ligase Cofactors, Donors and Acceptors," filed Jul. 6, 2009, which is hereby incorporated by reference in its entirety for all purposes.

STATEMENT OF GOVERNMENT SUPPORT

This invention was made with government support under Grant No. GM093562 awarded by the National Institute for General Medical Science, National Institutes of Health. The Government has certain rights in the invention.

The Sequence Listing written in file 95109-870702-2_ST25.TXT, created Apr. 18, 2014, 18,691 bytes, machine format IBM-PC, MS-Windows operating system, is hereby incorporated by reference.

FIELD OF THE INVENTION

Provided herein are methods and compositions for ligation of nucleic acids. In particular aspects and embodiments, the methods and compositions improve ligase specificity between matched and mismatched nucleic acid targets and/or reduce or inhibit template independent ligation using modified ligase cofactors, donors and acceptors and combinations thereof. In other particular aspects and embodiments, the methods and compositions improve ligase specificity for formation of nucleic acid libraries utilizing acceptor and donor adapter probes with modifications that reduce or inhibit probe dimerization.

BACKGROUND OF THE INVENTION

The following description is provided to assist the understanding of the reader. None of the information provided or references cited is admitted to be prior art in the present invention.

Nucleic acid ligases belong to a class of enzymes that catalyze phosphodiester bond formation between adjacent 3'-hydroxyl and 5'-phosphoryl termini in nucleic acid (e.g., RNA or DNA) in the presence of a cofactor, such as ATP or NAD+. Ligases are employed in a number of molecular biology applications including nucleic acid sequence detection, single nucleotide polymorphism (SNP) detection, protein detection, sequencing by ligation, and ligase chain reaction (LCR).

In biochemical fidelity experiments, DNA ligases have been found to tolerate a variety of nucleic acid substrate mismatches. For example, T4 DNA ligase has a tolerance for mismatches that results in a propensity to seal one of every $10^3$ mismatched duplexes. Showalter, A. K., et al., 106 Chem. Rev, 340-360 (2006). In comparison, the error rate of a conventional DNA polymerase is approximately one error for every $10^5$-$10^6$ dNTP insertions, several orders of magnitude higher in fidelity than ligase. Other atypical joining reactions of DNA ligase include intramolecular loop formation (Western, L., et al., 19 Nucleic Acids Res, 809-813 (1991)), joining of non-overlapping, blunt-ended duplexes (Barringer, K., et al., 89 Gene, 117-122 (1990), Cao, W., 22 Trends Biotechnol., 38-44 (2004)) and template-independent reactions (Barringer, K., et al., Kuhn, H., et al., 272 FEBS J, 5991-6000 (2005)).

Various approaches have been described for improving DNA ligation fidelity. For example, Luo, J., et al., 24 Nucleic Acids Res, 3079-3085 (1996) disclose modifying the third nucleotide upstream from the 3'-OH, acceptor with universal base 3-nitropyrrole and site directed mutagenesis of the ligase protein. Tong, J., et al., 27 Nucleic Acids Res, 788-794 (1999); Feng, H., et al., 43 Biochemistry, 12648-12659 (2004); Jeon, H., et al., 237 FEMS Microbiol Lett., 111-118 (2004); Lim, J., et al., 388 Arch Biochem Biophys., 253-260 (2001); and Luo, J., et al., 24 Nucleic Acids Res, 3071-3078 (1996) disclose mutating amino acid residues in the DNA ligase. Cao, W., 22 Trends Biotechnol., 38-44 (2004) disclose using an endonuclease in the ligation reaction. Egholm, M., et al., U.S. Pat. No. 6,297,016 disclose acceptor modifications. Fung, S., et al., U.S. Pat. No. 5,593,826 discloses 3'-$NH_2$ substituted acceptor probes. Bandaru, R., et al., U.S. Pat. Nos. 6,811,986 and 6,635,425 discloses use of 5'-thiophosphates in the donor (5'-phosphate) strand.

Modified ligase cofactors have been used determine ligase cofactor dependence and as ligation inhibitors. See e.g., Montecucco, A., et al., 271 Biochem J., 265-268 (1990); Shuman, S., 34 Biochemistry, 16138-16147 (1995); Raae, A., et al., 81 Biochem. Biophys. Res. Commun., 24-27 (1978); Cherepanov, A. V., et al., 269 Eur. J. Biochem., 5993-5999 (2002); Belford, H. G., et al., 268 J Biol Chem, 2444-2450 (1993); Doherty, A. J., et al., 271 J Biol Chem, 11083-11089 (1996); Ho, C. K., et al., 71 J Virol, 1931-1937 (1997); Lai, X., et al., 6 Extremophiles, 469-477 (2002); and Sriskanda, V., et al., 28 Nucleic Acids Res, 2221-2228 (2000).

Nucleic acid library preparation schemes involve the addition of adapter sequences onto the 5'- and 3'-termini of target nucleic acids. For RNA libraries, adapters are typically added in two sequential ligation steps to minimize adapter dimer formation, as described in Tian, G., et. al., 10 BMC Biotechnol, 64 (2010). First, an adenylated version of the 3'-adapter probe is ligated onto the 3'-terminus of the RNA library, in the absence of ATP, using a truncated version of T4 RNA ligase 2 that utilizes 5'-adenylated, rather than 5'-phosphorylated probes. Next, the 5'-adapter probe sequence is added onto the 5'-end of the RNA library using T4 RNA ligase 1. One approach to suppress adapter dimer formation is by hybridization of the cDNA synthesis primer after ligation of the 3'-adapter and before the 5'-adapter ligation step, as described in Nakashe, P., et al. 1 Journal OMICS Research, 6-11 (2011). Another approach, described by Kawano, M., et al. 49 Biotechniques, 751-755 (2010) employs a hybridization step between adapter dimers and an LNA sequence to block downstream replication.

Several approaches to tag double-stranded DNA (dsDNA) libraries in preparation for next generation sequencing (NGS) have been described, as reviewed by Linnarsson, S., 316, Exp Cell Res 1339-1343 (2010), and most involve a ligation step. In one approach, probe sequences are added onto dsDNA libraries by ligation of a pair of 5'-phosphorylated blunt-ended dsDNA adapter probes (P1 and P2) onto 5'-phosphorylated blunt-ended dsDNA libraries. The P1 and P2 adapter sequences are added onto both ends of the dsDNA library using T4 DNA ligase in a single step. Blunt ended adapter ligation strategies are typical for SOLiD (Life Technologies, Carlsbad, Calif.) and 454 GS FLX (Roche, Branford, Conn.) workflows. In another approach, the dsDNA library is subjected to a different polishing step, which produces dsDNA libraries that contain a single A tail on the 3'-end. The A-tailed dsDNA library is ligated to a dsDNA adapter, which contains a single T tail on the 3'-terminus and a 5'-phosphate in a single step using T4 DNA ligase. A-tailed ligation strategies are typical for the Genome Analyzer platform (Illumina, San Diego, Calif.). All three approaches are prone to adapter dimer formation, as described by Linnarsson, S., 316, Exp Cell Res 1339-1343 (2010); Quail, M. A., et al. 5, Nat Methods 1005-1010 (2008), and Huang, J., et al., 6, PLoS One, e19723 (2011).

SUMMARY OF THE INVENTION

Provided herein are methods and compositions for nucleic acid ligation. These methods involve the use of nucleic acid ligase, nucleic acid substrates, ligase cofactors, donors, acceptors, in nucleic acid ligation reactions. In certain aspects, the methods are accomplished by use of modified ligase cofactors, modified donors, modified acceptors or combinations thereof (collectively referred to herein as "modified ligase components"), which provide improved fidelity in nucleic acid ligation. In preferred embodiments, the modified ligase cofactors are modified ATP and modified NAD+.

According to one aspect, there are provided methods for a detecting a mutation in a target nucleic acid. In certain embodiments of the aspects provided herein, the method includes incubating the target nucleic acid in a reaction mixture including a cofactor dependent nucleic acid ligase, a ligase cofactor, a donor polynucleotide and an acceptor polynucleotide, where one or more of the ligase cofactor, donor polynucleotide and acceptor polynucleotide are modified; and monitoring ligation of the donor and acceptor polynucleotides, where the amount of ligation is indicative of the presence or absence of the mutation.

In a second aspect, there are provided methods for detecting the presence or absence of one of the alternative bases at a single nucleotide polymorphism (SNP) site in a target nucleic acid. In certain embodiments of the aspects provided herein, the method includes incubating the target nucleic acid in a reaction mixture including a cofactor dependent nucleic acid ligase, a ligase cofactor, a donor polynucleotide and an acceptor polynucleotide, where one or more of the ligase cofactor, donor polynucleotide and acceptor polynucleotide are modified; and monitoring ligation of the donor and acceptor polynucleotides, where the amount of ligation indicates the presence or absence of the one of the alternative bases at the single nucleotide polymorphism (SNP) in the target nucleic acid.

In a third aspect, there are provided methods for distinguishing the presence of a first nucleic acid sequence or a second nucleic acid sequence in a target nucleic acid. In certain embodiments of the aspects provided herein, the methods include incubating the target nucleic acid in a reaction mixture including a cofactor dependent nucleic acid ligase, a ligase cofactor, a donor polynucleotide and an acceptor polynucleotide, where one or more of the ligase cofactor, donor polynucleotide and acceptor polynucleotide are modified; and monitoring ligation of the donor and acceptor polynucleotides, where presence or amount of ligated nucleic acid is indicative of presence or amount of the first nucleic acid sequence in the target nucleic acid and/or the absence of the second nucleic acid sequence in the target nucleic acid; and the absence of ligation is indicative of the absence of the first nucleic acid sequence in the target nucleic acid.

In a fourth aspect, there are provided methods determining the presence or absence of a particular nucleotide at a specified position of a target nucleic acid. In certain embodiments of the aspects provided herein, the methods include incubating the target nucleic acid in a reaction mixture including a cofactor dependent nucleic acid ligase, a ligase cofactor, a donor polynucleotide and an acceptor polynucleotide, where one or more of the ligase cofactor, donor polynucleotide and acceptor polynucleotide are modified; and monitoring ligation of the donor and acceptor polynucleotides, where presence of ligated nucleic acid is indicative of presence of the particular nucleotide at the specified position of the target nucleic acid and absence of ligation is indicative of absence of the particular nucleotide at the specified position of the target nucleic acid.

In a fifth aspect, there are provided kits that include the compositions provided herein and kits for performing the methods provided herein. Kits include modified ligation components for performing ligation as described herein are also provided. For example, kits may contain ligase enzyme and modified cofactors to detect common nucleic acid targets such as allele-specific products. The kit containing a modified ligation component may include a container marked for nucleic acid ligation, instructions for performing nucleic acid ligation and/or one or more reagents selected from the group consisting of modified cofactor, nucleic acid ligase, and reaction buffer. The kit containing a modified ligation component may also include one or more donor and acceptor polynucleotides. In one embodiment, the modified donor and acceptor polynucleotides are modified. The kits may include a container marked for nucleic acid ligation, instructions for performing nucleic acid ligation and at least one modified ligation component and/or one or more reagents selected from the group consisting of ligase cofactor, nucleic acid ligase, magnesium, donor sequence, acceptor sequence, and reaction buffer.

In a sixth aspect, provided herein are methods for identifying modified ligation components for performing ligation as described herein are also provided. In some embodiments, the methods identify a modified cofactor that has increased specificity relative to the natural ligation component or other modified ligation component. For example, the methods may evaluate the performance of a modified cofactor in the presence of a matched or mismatched template. In some embodiments, the mismatched region will hybridize to the donor probe, and in other embodiments, the mismatched region will hybridize to the acceptor probe. In some embodiments the performance of a modified cofactor will be evaluated for reduction or inhibition of ligation activity in the absence of a nucleic acid template. In some embodiments, the methods identify a modified ligation component that has improved ligation specificity relative to the natural or unmodified cofactor. In some embodiments, the methods allow identification of a modified ligation component which use provides a similar rate of ligation relative to the natural or unmodified cofactor for matched nucleic acid. In other embodiments, the methods allow identification of a modified ligation component that has improved ligation specificity in the presence of mismatched nucleic acid relative to the natural or unmodified cofactor. In yet other embodiments, the methods evaluate a modified ligation component for ligation amount or yield where there are one or more base-pair mismatches at the ligation junction or within 10 bases of the ligation junction. In still further embodiments, the methods evaluate a modified ligation component for the ability to reduce or inhibit ligation in the absence of nucleic acid template.

In a seventh aspect, there are provided methods for reducing or inhibiting ligation in the absence of target nucleic acid. In certain embodiments of the aspects provided herein, the method includes incubating the target nucleic acid in a reaction mixture including a cofactor dependent nucleic acid ligase, a ligase cofactor, a donor polynucleotide and an acceptor polynucleotide, where one or more of the ligase cofactor, donor polynucleotide and acceptor polynucleotide are modified, where the presence of the modified ligation component inhibits or reduces ligation in the absence of target nucleic acid.

In some embodiments of the compositions and methods provided herein include modified ligation components, particularly modified ligase cofactor, modified acceptor, modified donors and combinations thereof. In particular embodiments, the modified ligation components include those as depicted in Formulas I-III described in further detail herein.

The modified ligation components of the methods and compositions provided herein have significant advantages. For example, an end user can use the same or similar ligation protocols and methods already in use with unmodified/natural cofactors (i.e., ATP and NAD+), unmodified donor probes or unmodified acceptor probes. The modified ligation components of the methods and compositions provided herein are compatible with existing ligation systems and reagents; no additional enzymes or reagents are needed but can be used.

The modified ligation components of the methods and compositions provided herein preferably have at least about the same efficacy for nucleic acid ligation in the presence of complementary target as compared to the unmodified ligation component. Preferably, ligation in the presence of non complementary or mismatched target nucleic acid is considered impaired when a modified ligation component is at least 50% less efficacious as a reagent in a ligation reaction compared to its corresponding unmodified ligation component, preferably at least 60% less efficacious, preferably at least 70% less efficacious, more preferably at least 80% less efficacious, more preferably at least 90% less efficacious, more preferably at least 95% less efficacious, more preferably at least 99% less efficacious and most preferably 100% less efficacious as a reagent in a ligation reaction than its corresponding unmodified ligation component. One of ordinary skill in the art is able to readily determine the level of ligation activity and efficacy of modified ligation component.

The modified ligation components of the methods and compositions provided herein preferably have no or reduced efficacy for nucleic acid ligation in the presence of a mismatched target as compared to the unmodified ligation component.

In an eighth aspect, methods are provided for preparing nucleic acid libraries utilizing modified acceptor adapter probes (also referred to herein as "modified 3'-adapter probes" and "modified acceptor probes") and modified donor adapter probes (also referred to herein as "modified 5'-adapter probes" and "modified donor probes") (collectively referred to herein as "modified adapter probes") with ligase enzyme that reduce or inhibit probe dimerization. In this aspect of the present invention, the modified adapter probes are single stranded. In certain embodiments, the method for reduction or inhibition of probe dimerization involves a first step of incubating the target nucleic acid library in a reaction mixture with a nucleic acid ligase and a 5'-adenylated modified donor adapter probe, and a second step of incubating the target nucleic acid library in a reaction mixture including a cofactor dependent nucleic acid ligase, a ligase cofactor, and a modified acceptor adapter probe. In certain embodiments, the method includes incubating the target nucleic acid library in a reaction mixture including a cofactor dependent nucleic acid ligase, a ligase cofactor, a modified donor adapter probe and a modified acceptor adapter probe. Alternatively, the ligase cofactor may also be modified. Each library preparation method provides efficient ligation of the adapter probes to the library as well as the reduction or inhibition of adapter probe dimerization. Furthermore, any adapter dimer that may form will have two or more sequential modification groups, thereby suppressing replication by nucleic acid polymerase.

In an ninth aspect, methods are provided for preparing nucleic acid libraries utilizing modified acceptor adapter probes and modified donor adapter probes with ligase enzyme that reduce or inhibit probe dimerization. In this aspect of the present invention, the modified adapter probes are double stranded. In certain embodiments, the double stranded modified adapter probes comprise a modified acceptor adapter probe hybridized to a modified donor adapter probe. The complementarity of the modified adapter and donor probes may be complete or partial. In certain embodiments, library preparation involves a blunt ended ligation step between the nucleic acid library and the double stranded modified adapter probes. In other certain embodiments, the library preparation method involves a ligation step wherein there is a single nucleotide of complementarity between the nucleic acid library and the double stranded modified adapter probes. In certain embodiments, the method includes incubating the target nucleic acid library in a reaction mixture including a cofactor dependent nucleic acid ligase, a ligase cofactor, and one or more double stranded modified adapter probes for improved library preparation specificity and reduced or inhibited probe dimerization. In certain embodiments, the method for reduction or inhibition of probe dimerization involves a first step of incubating the target nucleic acid library in a reaction mixture with a nucleic acid ligase and a 5'-adenylated double stranded modified adapter probe, and a second step of adding a ligase cofactor to the reaction mixture. Alternatively, the ligase cofactor may also be modified. Each library preparation method provides efficient ligation of the adapter probes to the library as well as the reduction or inhibition of adapter probe dimerization. Furthermore, any adapter dimer that may form will have two or more sequential modification groups, thereby suppressing replication by nucleic acid polymerase.

In a tenth aspect, these compositions may be provided in kits for preparing nucleic acid libraries. In one or more embodiments, a kit may include one or more modified donor and acceptor probes for performing ligation, one or more ligase enzymes and/or one or more modified cofactors.

As used herein, the term "ligase cofactor" refers to chemical compound that interacts with a ligase such that the ε-amino group of lysine of the ligase attacks the alpha phosphate (i.e., the phosphate directly attached to the 5' oxygen of the adenosine component) of the cofactor (e.g., ATP or NAD+) to form a covalent phosphoramidate linkage (e.g., as shown in FIG. 1). In certain embodiments, the ligase cofactor is ATP, NAD+ or GTP. Generally ligases are ATP-dependent or NAD+-dependent.

As used herein, the term "modified ligase cofactor" refers to a ligase cofactor with a substitution group attached. In preferred embodiments, the modified ligase cofactor is modified ATP or modified NAD+. In some embodiments, a modified ligase cofactor has more than one substitution group. Modified cofactors include those depicted herein, for example, Formula I. In certain embodiments, the modified ligase cofactor is not ATP-αS (i.e., 5'-α-thio adenosine triphosphate), ATP-γS (i.e., 5'-[γ-thio]-triphosphate) or AMP-PNP (i.e., 5'-[β,γ-imido]-triphosphate).

As used herein, the term "unmodified ligase cofactor" or "natural ligase cofactor" in relation to a "modified ligase cofactor" refers to the corresponding ligase cofactor without the substitution group. For example, an unmodified ligase cofactor relative to modified ATP is ATP.

As used herein, the term "donor," "donor polynucleotide," "5'-phosphorylated donor polynucleotide" or "donor probe" refers to a polynucleotide with a 5' phosphate capable of being ligated to an acceptor. A donor may be suitable for ligation when hybridized in close proximity to an acceptor on a complementary target nucleic acid in conditions suitable for nucleic acid ligation; preferably an acceptor and donor hybridize adjacent to each other on a complementary target nucleic acid. In some embodiments, a donor has at least one nucleic acid site that is not complementary (mismatch) to a target nucleic acid. In particular embodiments, the mismatch is at a nucleotide of interest (e.g., SNP site). Additional alternative polynucleotides suitable for the methods and compositions provided herein include, but are not limited to, modified ribonucleotides, modified deoxyribonucleotides, modified phosphate-sugar-backbone oligonucleotides, nucleotide analogs and mixtures thereof. In preferred embodiments, the donor is an oligonucleotide. As used herein, the term "modified donor," "modified donor polynucleotide" or "modified donor probe" refers to a donor with a substitution group. Preferably, the substitution group is in close proximity to the ligation junction (e.g., 1, 2, 3, 4, or 5 nucleotides downstream of the ligation junction). In preferred embodiments, the substitution group is at the 2' position of the ribose and/or one or more internucleotide phosphates. In some embodiments, a modified donor has more than one substitution group. Modified donors include those depicted herein, for example, Formula III.

As used herein, the term "acceptor," "acceptor polynucleotide," "3'-hydroxyl terminated acceptor polynucleotide," or "acceptor probe" refers to a polynucleotide with a 3' OH group capable being ligated to a donor. An acceptor may be suitable for ligation when hybridized in close proximity to an donor on a complementary target nucleic acid in conditions suitable for nucleic acid ligation; preferably an acceptor and donor hybridize adjacent to each other on a complementary target nucleic acid. In some embodiments, an acceptor has at least one nucleic acid site that is not complementary (mismatch) to a target nucleic acid. In particular embodiments, the mismatch is at a nucleotide of interest (e.g., SNP site). Additional alternative polynucleotides suitable for the methods and compositions provided herein include, but are not limited to, modified ribonucleotides, modified deoxyribonucleotides, modified phosphate-sugar-backbone oligonucleotides, nucleotide analogs and mixtures thereof. In preferred embodiments, the acceptor is an oligonucleotide. As used herein, the term "modified acceptor," "modified acceptor polynucleotide" or "modified acceptor probe" refers to an acceptor with a substitution group. Preferably, the substitution group is in close proximity to the ligation junction (e.g., 1, 2, 3, 4, or 5 nucleotides upstream of the ligation junction). In preferred embodiments, the substitution group is at the 2' position of the ribose and/or one or more internucleotide phosphates. In some embodiments, a modified acceptor has more than one substitution group. Modified acceptors include those depicted herein, for example, Formula II.

As used herein, the term "modified adapter probes" refers to 5'-modified adapter probe, modified donor adapter probe, modified acceptor adapter probe, and the 3'-modified adapter probe. Modified adapter probes may be single stranded or double stranded, and are referred to as "single stranded modified adapter probes" and "double stranded modified adapter probes," respectively. In certain embodiments, the double stranded modified adapter probes comprise a modified acceptor adapter probe hybridized to a modified donor adapter probe. In this circumstance, the complementarity of the modified acceptor and donor probes may be complete or partial.

As used herein, the term "substitution group" refers to any chemical moiety that can be attached to a ligase cofactor, donor, or acceptor. The substitution group may be attached at locations which include but are not limited to the phosphate, sugar, triphosphate, nucleoside base moiety and internucleotide linkage. The substitution group may be a group of any nature compatible with the process of nucleic acid ligation. In preferred embodiments, the substitution group increases the specificity or fidelity of nucleic acid ligation (e.g., the ability to ligate complementary nucleic acid and not ligate, or reduce ligation of non-complementary nucleic acid) when attached to a ligase cofactor, donor polynucleotide or acceptor polynucleotide. In preferred embodiments, the substitution group when attached to a ligase cofactor, donor polynucleotide or acceptor polynucleotide reduces, inhibits, or eliminates ligation of noncomplementary nucleic acid as compared with ligation in the absence of the substitution group. In preferred embodiments, the substitution group when attached to a ligase cofactor, donor polynucleotide or acceptor polynucleotide reduces, inhibits, or eliminates ligation of noncomplementary nucleic acid as compared with ligation of complementary nucleic acid. In preferred embodiments, the substitution group when attached to a ligase cofactor, donor polynucleotide or acceptor polynucleotide reduces, inhibits, or eliminates ligation in the absence of template. In other preferred embodiments, the substitution group when attached to a donor polynucleotide or acceptor polynucleotide reduces, inhibits, or eliminates ligation to form adapter dimers, while allowing for efficient ligation to the nucleic acid library.

In addition, the substitution group may include a detectable label. Thus, following ligation, a labeled nucleic acid may be identified by size, mass, affinity capture and/or color. Detectable labels include, but are not limited to, chromophores, fluorescent moieties, enzymes, antigens, heavy metals, magnetic probes, dyes, phosphorescent groups, radioactive materials, chemiluminescent moieties and electrochemical detecting moieties. The detectable label is preferably a fluorescent dye; a preferable affinity capture label is biotin.

As used herein, the term "modified ligation components" refers to modified ligase cofactors, modified acceptors and modified donors refers to each component individually, collectively or to combinations thereof. For example, modified ligation components may refer to modified ligase cofactors only; modified ligase cofactors having one type of modification; modified ligase cofactors having more than one type of modification; modified ligase cofactors and modified donors; modified ligase cofactors and modified acceptors; or modified ligase cofactors, modified ligase acceptors and modified ligase donors.

As used herein, the term "ligation" or "ligate" refers to methods known in the art for joining polynucleotides. Preferably ligation refers to joining the 3'-end of an acceptor polynucleotide to the 5'-end of a donor polynucleotide. In some embodiments, a nick in duplex nucleic acid is ligated to form a phosphodiester bond or equivalent internucleotide linkage, thereby forming a longer, complementary copy of the template nucleic acid sequence. A nicked nucleic acid duplex consists of a 3'-hydroxyl terminated acceptor oligonucleotide hybridized to a complementary nucleic acid template, with a 5'-phosphorylated donor oligonucleotide hybridized immediately downstream of an acceptor oligonucleotide. Ligation involving the compositions and methods provided herein may employ one or more modified cofactor, one or more modified donor and modified acceptor polynucleotides with joining by nucleic acid ligase. Ligation of donor and acceptor probes upon a target nucleic acid may occur with or without turnover of the ligated probes. Preferably, ligation occurs with turnover. A template nucleic acid may be DNA, RNA, cDNA, PNA, LNA and/or a modified nucleic acid template, or any combination thereof. While the exemplary methods described hereinafter relate to ligation, numerous other methods suitable for the methods and compositions provided herein are known in the art for enzymatic ligation of nucleic acids. As used herein, the term "ligation junction" refers to the two adjacent nucleic acid positions along a template where a donor probe and an acceptor probe are ligated.

As used herein, "blunt ended ligation" refers to the joining of two ds DNA duplexes by T4 DNA ligase without the presence of a template. Blunt ended ligations are inherently lower in efficiency, requiring a higher ligase concentration to be used. T4 DNA ligase is the only commercially-available DNA ligase to anneal blunt ends) as described by Tabor, Stanley. DNA ligases. Chapter in: Current Protocols in Molecular Biology, Book 1. 2001 Wiley Interscience.

As used herein, the term "ligase" or "nucleic acid ligase" refers to an enzyme that is capable of ligating nucleic acid. Preferably a ligase is capable of ligating the 3'-end of an acceptor polynucleotide to a the 5'-end of a donor polynucleotide. In other embodiments, the nicked duplex may contain DNA, RNA, cDNA, PNA, LNA, and/or other modified nucleosides, or any combination thereof. In some embodiments, the ligase is one of the following: bacteriophage T4 DNA ligase, *Escherichia coli* (*E. coli*) DNA ligase, *Aquifex aeolicus* DNA ligase, *Thermus aquaticus* (Taq) DNA ligase, 9° N™ DNA ligase, *Methanobacterium thermoautotrophicum* RNA ligase, *Ferroplasma acidiphilum* DNA ligase, Human DNA ligase I, Human DNA ligase II, Human DNA ligase III, Human DNA ligase IV, Vaccinia virus DNA ligase, Chlorella virus DNA ligase, *Pyrococcus furiosis* DNA ligase, *Haloferax volcanii* DNA ligase, *Acidianus ambivalens* DNA ligase, *Archaeoglobus fulgidus* DNA ligase, *Aeropyrum pernix* DNA ligase, *Cenarcheon symbiosum* DNA ligase, *Haloarcula marismortui* DNA ligase, *Ferroplasma acidarmanus* DNA ligase, *Natronomonas pharaosis* DNA ligase, *Haloquadratum walsbyi* DNA ligase, *Halobacterium salinarum* DNA ligase, *Methanosarcina acetivorans* DNA ligase, *Methanosarcina barkeri* DNA ligase, *Methanococcoides burtonii* DNA ligase, *Methanospirillum hungatei* DNA ligase, *Methanocaldococcus jannaschii* DNA ligase, *Methanopyrus kandleri* DNA ligase, *Methanosarcina mazei* DNA ligase, *Methanococcus maripaludis* DNA ligase, *Methanosaeta thermophile* DNA ligase, *Methanosphaera stadtmanae* DNA ligase, *Methanothermobacter thermautotrophicus* DNA ligase, *Nanoarchaeum equitans* DNA ligase, *Pyrococcus abyssi* DNA ligase, *Pyrobaculum aerophilum* DNA ligase, *Pyrococcus horikoshii* DNA ligase, *Picrophilus torridus* DNA ligase, *Sulfolobus acidocaldarius* DNA ligase, *Sulfolobus shibatae* DNA ligase, *Sulfolobus solfataricus* DNA ligase, *Sulfolobus tokodaii* DNA ligase, *Thermoplasma acidophilum* DNA ligase, *Thermococcus fumicolans* DNA ligase, *Thermococcus kodakarensis* DNA ligase, *Thermococcus* sp. NA1 DNA ligase, *Thermoplasma volcanium* DNA ligase, *Staphylococcus aureus* DNA ligase, *Thermus scotoductus* NAD⁺-DNA ligase, T4 RNA ligase, *Staphylococcus aureus* DNA ligase, *Methanobacterium thermoautotrophicum* DNA ligase, *Thermus* species AK16D DNA ligase, *Haemophilus influenzae* DNA ligase, *Thermus thermophilus* DNA ligase, bacteriophage T7 DNA ligase, *Haemophilus influenzae* DNA ligase, *Mycobacterium tuberculosis* DNA ligase, *Deinococcus radiodurans* RNA ligase, *Methanobacterium thermoautotrophicum* RNA ligase, *Rhodothermus marinus* RNA ligase, *Trypanosoma brucei* RNA ligase, bacteriophage T4 RNA ligase 1, Ampligase, and bacteriophage T4 RNA ligase 2.

As used herein, the term "monitoring ligation" refers to detecting the presence, detecting the absence and/or measuring the amount of ligated nucleic acid. Ligation may be monitored, for example, by detecting and/or quantifying the amount of ligation products using gel electrophoresis or a detectable label (e.g., fluorescent or chemiluminescent probe) or by correlating presence and/or amount of a product of a subsequent process to the presence and/or amount of ligation product (e.g., by directly correlating the presence and/or amount of subsequent amplification of ligated products to the amount of ligation product). Monitoring ligation also include any method of assessing the size of nucleic acids to indicate whether ligation has occurred or not or to assess what portion of total nucleic acid present in a sample has ligated and what portion has not; such results may be expressed in terms of a percentage or a ratio. Monitoring ligation includes any of the methods disclosed herein as well as methods known in the art.

As used herein, the term "replication" refers to the enzymatic formation of a copy of a nucleic acid sequence. Replication is typically accomplished by the use of a nucleic acid polymerase, which may include reverse transcriptase, DNA polymerase, and RNA polymerase.

As used herein, the term "nucleic acid" refers to a polynucleotide, an oligonucleotide, or any fragment thereof, any ribo- or deoxyriboderivatives and to naturally occurring or synthetic molecules containing natural and/or modified nucleotide residues and internucleotide linkages. These phrases also refer to DNA or RNA of natural (e.g., genomic) or synthetic origin which may be single-stranded, double-stranded, triple-stranded or tetra-stranded and may represent the sense or the antisense strand, or to any DNA-like or RNA-like material. An "RNA equivalent," in reference to a DNA sequence, is composed of the same linear sequence of nucleotides as the reference DNA sequence with the exception that all or most occurrences of the nitrogenous base thymine are replaced with uracil, and the sugar backbone is composed of ribose instead of 2'-deoxyribose. Additional alternative nucleic acid backbones suitable for the methods and compositions provided herein include but are not limited to phosphorothioate, phosphoroselenoate, alkyl phosphotriester, aryl phosphotriester, alkyl phosphonate, aryl phosphonate, Locked Nucleic Acids (LNA), and Peptide Nucleic Acids (PNA) and phosphoboronate, and combinations thereof. RNA may be used in the methods described herein and/or may be converted to cDNA by reverse-transcription for use in the methods described herein.

As used herein, the term "polynucleotide" refers to a nucleic acid chain, usually single stranded, may be naturally occurring or synthetic. Throughout this application, nucleic acids are designated by the 5'-terminus to the 3'-terminus. Standard nucleic acids, e.g., DNA and RNA, are often chemically synthesized "3' to 5'," i.e., by the addition of nucleotides to the 5'-terminus of a growing nucleic acid. Polynucleotides may include DNA, RNA, PNA, LNA, other modified nucleosides, or combinations thereof. In some embodiments, a polynucleotide is an oligonucleotide. As used herein, the term "nucleotide" refers to a subunit of a nucleic acid consisting of a phosphate group, a 5-carbon sugar and a nitrogenous base. The 5'-carbon sugar found in RNA is ribose. In DNA, the 5'-carbon sugar is 2'-deoxyribose. The term also includes analogs of such subunits.

As used herein, the term "oligonucleotide" refers to a polynucleotide having a sequence of between about 5 to about 200 nucleotides, more preferably about 10 to about 100 nucleotides, more preferably about 10 to about 70, more preferably about 10 to about 50 nucleotides, more preferably about 10 to about 30 nucleotides or more preferably about 15 to about 25 nucleotides. In some embodiments, an oligonucleotide includes a sequence of at least 5 nucleotides, at least 10 nucleotides, at least 15 nucleotides, at least 20 nucleotides, at least 25 nucleotides, at least 30 nucleotides, at least 35 nucleotides, at least 40 nucleotides, at least 45 nucleotides, at least 50 nucleotides, at least 55 nucleotides, at least 60 nucleotides, at least 65 nucleotides, at least 70 nucleotides in length, at least 75 nucleotides, at least 80 nucleotides in length, at least 90 nucleotides in length, at least 100 nucleotides in length, at least 200 nucleotides in length; or less than 200 nucleotides, less than 150 nucleotides, less than 100 nucleotides, less than 90 nucleotides, less than 80 nucleotides, less than 70 nucleotides, less than 65 nucleotides, less than 60 nucleotides, less than 55 nucleotides, less than 50 nucleotides, less than 45 nucleotides, less than 40 nucleotides, less than 35 nucleotides, less than 30 nucleotides, less than 25 nucleotides, less than 20 nucleotides, less than 15 nucleotides; or combinations thereof, in length. In certain embodiments, an oligonucleotide is 4, 5, 6, 7, 8, 9, 10, 11 or 12 nucleotides in length.

As used herein, the term "primer" or "oligonucleotide primer" refers to a polynucleotide or oligonucleotide suitable for priming an enzyme based nucleic acid extension reaction, e.g., amplification and ligation. The skilled artisan is capable of designing and preparing primers that are appropriate for extension of a target sequence. The length of primers for use in the methods and compositions provided herein depends on several factors including the nucleotide sequence identity and the temperature at which these nucleic acids are hybridized or used during in vitro nucleic acid extension. The considerations necessary to determine a preferred length for the primer of a particular sequence identity are well known to the person of ordinary skill. For example, the length of a short nucleic acid or oligonucleotide can relate to its hybridization specificity or selectivity. As used herein, the term "primer binding sequence" or "PBS" refers to a nucleic acid region that specifically hybridizes or anneals to a specified primer.

As used herein, the term "probe" or "oligonucleotide probe" refers to a polynucleotide or oligonucleotide suitable for detecting the presence or absence of specified nucleic acid.

As used herein, the term "target nucleic acid" refers to any nucleic acid of interest.

As used herein, the term "template nucleic acid" refers to a nucleic acid capable of binding to a donor and/or acceptor. Preferably the template nucleic acid comprises a target nucleic acid.

As used herein, the term "mutation" refers to a difference in a sequence of a first nucleic acid sequence as compared with a second nucleic acid sequence. For example, a mutation includes a substitution (such as a single nucleotide polymorphism), deletion, insertion, and translocation of nucleic acid in a first target nucleic sequence relative to a second nucleic acid sequence. A second nucleic acid sequence may be a wild-type sequence or the sequence of an alternative mutated site.

As used herein, the term "mismatch" refers to nucleotides or nucleic acid that are not complementary to a target nucleotide or nucleic acid. As used herein, the term "mismatch template" or "mismatched template" refers to double stranded nucleic acid where at least one base residue on either strand is not paired with any residue, or paired with an incorrect base, e.g., A not paired with T or C not paired with G. A ligation reaction with less than 100% fidelity/specificity forms a mismatched ligation product. As used herein, the term "matched template" refers to a target nucleic acid where all bases are complementary to the donor and acceptor probes.

As used herein, the term "single nucleotide polymorphism" or "SNP" refers to a single base genetic sequence variation between different individuals of a species or other specified population. In some embodiments, SNPs are single base pair positions at a specified nucleic acid site in genomic DNA at which different sequence alternatives (alleles) exist in normal individuals in some population(s) where the least frequent allele has an abundance of 1% or greater; or 0.8% or greater; or 0.5% or greater; or 0.4% or greater; or 0.3% or greater; or 0.2% or greater; or 0.1% or greater. In some embodiments, a SNP of interest is known by one of ordinary skill in the art, for example, a particular SNP is published in a scientific journal such as those accessible through Pubmed (available at http://www.ncbi.nlm.nih.gov/pubmed/) such as Science, Nature, PNAS and NEJM. In some embodiments, a SNP can be found in a database of polymorphisms such as those found at Entrez SNP (available at http://www.ncbi.nlm.nih.gov/sites/entrez?db=snp) or a human SNP database (available at http://www.ncbi.nlm.nih.gov/projects/SNP/). In some embodiments, a population includes all humans as a whole or a subset of humans, such as a group of people of a particular race, nationality, geographical region, family lineage, religion, gender, age, or from a particular period of time or era.

As used herein, the term "single nucleotide polymorphism site," "SNP site," or "SNP position" refers to a nucleic acid position where a SNP is known to occur.

As used herein, the term "terminus" with respect to a polynucleotide (preferably an oligonucleotide) refers to the nucleotides at the 3' or 5' end of an polynucleotide. Preferably the terminus of an polynucleotide includes the terminal 6 nucleotides, more preferably the terminal 5 nucleotides, more preferably the terminal 4 nucleotides, more preferably the terminal 3 nucleotides, more preferably the terminal 2 nucleotides, or more preferably the terminal nucleotide.

As used herein, the term "label" or "detectable label" refers to any compound or combination of compounds that may be attached or otherwise associated with a molecule so that the molecule can be detected directly or indirectly by detecting the label. A detectable label can be a radioisotope (e.g., carbon, phosphorus, iodine, indium, sulfur, tritium etc.), a mass isotope (e.g., $H^2$, $C^{13}$ or $N^{15}$), a dye or fluorophore (e.g., cyanine, fluorescein or rhodamine), a hapten (e.g., biotin) or any other agent that can be detected directly or indirectly. After incorporation of a labeled NTP into an amplicon or other polymerization product, the label may be detected.

As used herein, the term "hybridize" or "specifically hybridize" refers to a process where two complementary nucleic acid strands anneal to each other under appropriately stringent conditions. Hybridizations to target nucleic acids are typically and preferably conducted with probe-length nucleic acid molecules, preferably 20-100 nucleotides in length. Nucleic acid hybridization techniques are well known in the art. See, e.g., Sambrook, et al., Molecular Cloning: A Laboratory Manual, Second Edition, Cold Spring Harbor Press, Plainview, N.Y. (1989); Ausubel, F. M., et al., Current Protocols in Molecular Biology, John Wiley & Sons, Secaucus, N.J. (1994).

As used herein, the term "stringent hybridization condition" refers to hybridization conditions which do not allow for hybridization of two nucleic acids which are not completely complementary.

As used herein, the term "sample" or "test sample" refers to any liquid or solid material believed to include nucleic acid of interest. A test sample may be obtained from any biological source (i.e., a biological sample), such as cells in culture or a tissue sample or synthetically produced including a chemically synthesized template.

As used herein, the term "complement," "complementary," or "complementarity" in the context of an oligonucleotide or polynucleotide (i.e., a sequence of nucleotides such as an oligonucleotide primers or a target nucleic acid) refers to standard Watson/Crick base pairing rules. A complement sequence can also be a sequence of DNA or RNA complementary to the DNA sequence or its complement sequence, and can also be a cDNA. For example, the sequence "5'-A-G-T-C-3'" is complementary to the sequence "3'-T-C-A-G-5'." Certain nucleotides not commonly found in natural nucleic acids or chemically synthesized may be included in the nucleic acids described herein; these include but not limited to base and sugar modified nucleosides, nucleotides, and nucleic acids, such as inosine, 7-deazaguanosine, 2'-O-methylguanosine, 2'-fluoro-2'-deoxycytidine, Locked Nucleic Acids (LNA), and Peptide Nucleic Acids (PNA), and combinations thereof. Complementarity need not be perfect; stable duplexes may contain mismatched base pairs, degenerative, or unmatched nucleotides. Those skilled in the art of nucleic acid technology can determine duplex stability empirically considering a number of variables including, for example, the length of the oligonucleotide, base composition and sequence of the oligonucleotide, incidence of mismatched base pairs, ionic strength, other hybridization buffer components and conditions.

Complementarity may be partial in which only some of the nucleotide bases of two nucleic acid strands are matched according to the base pairing rules. Complementarity may be complete or total where all of the nucleotide bases of two nucleic acid strands are matched according to the base pairing rules. Complementarity may be absent where none of the nucleotide bases of two nucleic acid strands are matched according to the base pairing rules. The degree of complementarity between nucleic acid strands has significant effects on the efficiency and strength of hybridization between nucleic acid strands. This is of particular importance in ligation and amplification reactions, as well as detection methods that depend upon binding between nucleic acids. The terms may also be used in reference to individual nucleotides, especially within the context of polynucleotides. For example, a particular nucleotide within an oligonucleotide may be noted for its complementarity, or lack thereof, to a nucleotide within another nucleic acid strand, in contrast or comparison to the complementarity between the rest of the oligonucleotide and the nucleic acid strand.

As used herein, the term "substantially complementary" refers to two sequences that hybridize under near stringent hybridization conditions. The skilled artisan will understand that substantially complementary sequences need not hybridize along their entire length. In particular, substantially complementary sequences comprise a contiguous sequence of bases that do not hybridize to a target sequence, positioned 3' or 5' to a contiguous sequence of bases that hybridize under stringent hybridization conditions to a target sequence.

As used herein, a polynucleotide, oligonucleotide, primer or probe is "specific" for a nucleic acid if the polynucleotide or oligonucleotide primer hybridization sequence of the a polynucleotide or oligonucleotide primer has at least 50% sequence identity with a portion of the nucleic acid when the polynucleotide or oligonucleotide primer and the nucleic acid are aligned. A polynucleotide or oligonucleotide primer that is specific for a nucleic acid is one that, under the appropriate hybridization or washing conditions, is capable of hybridizing to the target of interest and not substantially hybridizing to nucleic acids sequences which are not of interest. Higher levels of sequence identity are preferred and include at least 75%, at least 80%, at least 85%, at least 90%, at least 95%, at least 99%, and more preferably 100% sequence identity.

As used herein, the term "nucleoside" includes all naturally occurring nucleosides, including all forms of nucleoside bases and furanosides found in natural nucleic acids. Base rings most commonly found in naturally occurring nucleosides are purine and pyrimidine rings. Naturally occurring purine rings include, for example, adenine, guanine, and $N^6$-methyladenine. Naturally occurring pyrimidine rings include, for example, cytosine, thymine, and 5-methylcytosine. Naturally occurring nucleosides for example include but not limited to ribo and 2'-deoxyribo derivatives of adenosine, guanosine, cytidine, thymidine, uridine, inosine, 7-deazaguanosine, 7-methylguanosine. Naturally occurring nucleosides also include modifications to the ribose sugar, as seen for 2'-O-methyluridine.

As used herein, the terms "nucleoside analogs," "modified nucleosides," or "nucleoside derivatives" include synthetic nucleosides as described herein. Nucleoside derivatives also include nucleosides having modified base or/and sugar moieties, with or without protecting groups. Such analogs include, for example, 2'-deoxy-2'-fluorouridine, and the like. The compounds and methods of provided herein include such base rings and synthetic analogs thereof, as well as unnatural heterocycle-substituted base sugars, and even acyclic substituted base sugars. Moreover, nucleoside derivatives include other purine and pyrimidine derivatives, for example, halogen-substituted purines (e.g., 6-fluoropurine), halogen-substituted pyrimidines, $N^6$-ethyladenine, $N^4$-(alkyl)-cytosines, 5-ethylcytosine, and the like. Nucleoside derivatives and analogs encompass a wide variety of modifications, such as those described in U.S. Pat. No. 6,762,298.

As used herein, the terms "universal base," "degenerate base," "universal base analog" and "degenerate base analog" includes, for example, an analog with an artificial base which is preferably recognizable by nucleic acid ligase as a substitute for any specific nucleobase of a nucleoside such as dA, A, dT, dU, U, dC, C, dG, G and other specific nucleobases. Nucleosides containing universal bases or degenerate bases can also be used and examples can be found in Loakes, D., 29 Nucleic Acids Res. 2437-2447 (2001); Crey-Desbiolles, C., et. al., 33 Nucleic Acids Res. 1532-1543 (2005); Kincaid, K., et. al., 33 Nucleic Acids Res. 2620-

2628 (2005); Preparata, F P, Oliver, J S, 11 J. Comput. Biol. 753-765 (2004); and Hill, F., et. al., 95 Proc Natl Acad Sci USA 4258-4263 (1998).

As used herein, the term "internucleotide linkage" refers to the bond or bonds that connect two nucleosides of an oligonucleotide primer or nucleic acid and may be a natural phosphodiester linkage or modified linkage.

As used herein, the term "acyl" denotes the group —C(O)$R^a$, where $R^a$ is hydrogen, lower alkyl, cycloalkyl, heterocyclyl, aryl, heteroaryl, and the like.

As used herein, the term "substituted acyl" denotes the group —C(O)$R^{a'}$, where $R^{a'}$ is substituted lower alkyl, substituted cycloalkyl, substituted heterocyclyl, substituted aryl, substituted heteroaryl, and the like.

As used herein, the term "acyloxy" denotes the group —OC(O)$R^b$, where $R^b$ is hydrogen, lower alkyl, substituted lower alkyl, cycloalkyl, substituted cycloalkyl, heterocyclyl, substituted heterocyclyl, aryl, substituted aryl, heteroaryl, substituted heteroaryl, and the like.

As used herein, the term "alkane" refers to an organic compound that includes carbon atoms and hydrogen atoms, and includes C—H bonds and additionally includes C—C single bonds in alkanes other than methane. The term "alkane" includes straight-chain alkanes such as alkanes having from 1 to 20 carbon atoms. In some embodiments, alkanes include straight-chain alkanes such as alkanes having from 1 to 8 carbon atoms such as methane, ethane, propane, butane, pentane, hexane, heptane, and octane. The term "alkane" also includes branched-chain alkanes such as, but not limited to branched chain alkanes having from 1 to 20, and in some embodiments from 1 to 8 carbon atoms such as, but not limited to, 2-methylpropane, 2,2-dimethylpropane, 2-methylbutane, 2,3-dimethylbutane, 2,2-dimethylbutane, 2-methylpentane, 3-methylpentane, 2,3-dimethylpentane, 2,4-dimethylpentane, 2,2-dimethylpentane, 3,3-dimethylpentane, 2-methylhexane, 3-methylhexane, 2,2-dimethylhexane, 2,3-dimethylhexane, 2,4-dimethylhexane, 2,5-dimethylhexane, 3,3-dimethylhexane, 3,4-dimethylhexane, 2-methylheptane, 3-methylheptane, 4-methylheptane, 3-ethylpentane, 3-ethyl-2-methylpentane, 3-ethylhexane, and the like. A C—C or a C—H bond of an alkane may be replaced with a bond to another group such as a hydroxyl group, a halogen such as F, Cl, Br, or I, a sulfhydryl group, or an amine group. Alkanes replaced with such groups may respectively be named as hydroxyalkanes, haloalkanes such as fluoroalkanes, chloroalkanes, bromoalkanes, iodoalkanes, mercaptoalkanes, and aminoalkanes.

As used herein, the term "alkenyl" refers to a straight-chain or branched-chain hydrocarbyl, which has one or more double bonds and, unless otherwise specified, contains from about 2 to about 20 carbon atoms, preferably from about 2 to about 10 carbon atoms, more preferably from about 2 to about 8 carbon atoms, and most preferably from about 2 to about 6 carbon atoms. Examples of alkenyl radicals include vinyl, allyl, 1,4-butadienyl, isopropenyl, and the like.

As used herein, the term "alkenylaryl" refers to alkenyl-substituted aryl groups and "substituted alkenylaryl" refers to alkenylaryl groups further bearing one or more substituents as set forth herein.

As used herein, the term "alkenylene" refers to divalent straight or branched chain hydrocarbyl groups having at least one carbon-carbon double bond, and typically containing 2-20 carbon atoms, preferably 2-12 carbon atoms, preferably 2-8 carbon atoms, and "substituted alkenylene" refers to alkenylene groups further bearing one or more substituents as set forth herein.

As used herein, the term "alkyl" refers to a single bond chain of hydrocarbons usually ranging from 1-20 carbon atoms, preferably 1-8 carbon atoms, examples include methyl, ethyl, propyl, isopropyl, and the like. Examples of such alkyl radicals include methyl, ethyl, propyl, isopropyl, n-butyl, sec-butyl, isobutyl, tert-butyl, pentyl, isoamyl, hexyl, octyl, dodecanyl, and the like.

As used herein, the term "lower alkyl" refers to a straight chain or a branched chain of hydrocarbons usually ranging from 1-6 carbon atoms, preferably 2-5 carbon atoms. Examples include ethyl, propyl, isopropyl, and the like.

As used herein, the term "alkylene" refers to a divalent hydrocarbyl containing 1-20 carbon atoms, preferably 1-15 carbon atoms, straight chain or branched, from which two hydrogen atoms are taken from the same carbon atom or from different carbon atoms. Examples of alkylene include, but are not limited to, methylene (—$CH_2$—), ethylene (—$CH_2CH_2$—), and the like.

As used herein, the term "alkynyl" refers to a straight-chain or branched-chain hydrocarbyl, which has one or more triple bonds and contains from about 2-20 carbon atoms, preferably from about 2-10 carbon atoms, more preferably from about 2-8 carbon atoms, and most preferably from about 2-6 carbon atoms. Examples of alkynyl radicals include ethynyl, propynyl (propargyl), butynyl, and the like.

As used herein, the term "alkynylaryl" refers to alkynyl-substituted aryl groups and "substituted alkynylaryl" refers to alkynylaryl groups further bearing one or more substituents as set forth herein.

As used herein, the term "alkoxy" denotes the group —O$R^c$, where $R^c$ is lower alkyl, substituted lower alkyl, aryl, substituted aryl, aralkyl, substituted aralkyl, heteroalkyl, heteroarylalkyl, cycloalkyl, substituted cycloalkyl, cycloheteroalkyl, or substituted cycloheteroalkyl as defined.

As used herein, the term "lower alkoxy" denotes the group —O$R^d$, where $R^d$ is lower alkyl.

As used herein, the term "alkylaryl" refers to alkyl-substituted aryl groups and "substituted alkylaryl" refers to alkylaryl groups further bearing one or more substituents as set forth herein.

As used herein, the term "alkylcarbonylamino" denotes the group —N$R^e$C(O)$R^f$, where $R^e$ is optionally substituted alkyl, and $R^f$ is hydrogen or alkyl.

As used herein, the term "alkylsulfinyl" denotes the group —S(O)$R^g$, where $R^g$ is optionally substituted alkyl.

As used herein, the term "alkylsulfonyl" denotes the group —S(O)$_2R^g$, where $R^g$ is optionally substituted alkyl.

As used herein, the term "alkylsulfonylamino" denotes the group —N$R^e$S(O)$_2R^f$, where $R^e$ is optionally substituted alkyl, and $R^f$ is hydrogen or alkyl.

As used herein, the term "alkylthio" refers to the group —S—$R^h$, where $R^h$ is alkyl.

As used herein, the term "substituted alkylthio" refers to the group —S—$R^i$, where $R^i$ is substituted alkyl.

As used herein, the term "alkynylene" refers to divalent straight or branched chain hydrocarbyl groups having at least one carbon-carbon triple bond, and typically having in the range of about 2-12 carbon atoms, preferably about 2-8 carbon atoms, and "substituted alkynylene" refers to alkynylene groups further bearing one or more substituents as set forth herein.

As used herein, the term "amido" denotes the group —C(O)N$R^jR^{j'}$, where $R^j$ and $R^{j'}$ may independently be hydrogen, lower alkyl, substituted lower alkyl, alkyl, substituted alkyl, aryl, substituted aryl, heteroaryl, or substituted heteroaryl.

As used herein, the term "substituted amido" denotes the group —C(O)NR$^k$R$^{k'}$, where R$^k$ and R$^{k'}$ are independently hydrogen, lower alkyl, substituted lower alkyl, aryl, substituted aryl, heteroaryl, or substituted heteroaryl, provided, however, that at least one of R$^k$ and R$^{k'}$ is not hydrogen. R$^k$R$^{k'}$ in combination with the nitrogen may form an optionally substituted heterocyclic or heteroaryl ring.

As used herein, the term "amidino" denotes the group —C(=NR$^m$)NR$^{m'}$R$^{m''}$, where R$^m$, R$^{m'}$, and R$^{m''}$ are independently hydrogen or optionally substituted alkyl, aryl, or heteroaryl.

As used herein, the term "amino" or "amine" denotes the group —NR''R''', where R'' and R''' may independently be hydrogen, lower alkyl, substituted lower alkyl, alkyl, substituted alkyl, aryl, substituted aryl, heteroaryl, or substituted heteroaryl as defined herein. A "divalent amine" denotes the group —NH—. A "substituted divalent amine" denotes the group —NR— where R is lower alkyl, substituted lower alkyl, alkyl, substituted alkyl, aryl, substituted aryl, heteroaryl, or substituted heteroaryl.

As used herein, the term "substituted amino" or "substituted amine" denotes the group —NR$^p$R$^{p'}$, where R$^p$ and R$^{p'}$ are independently hydrogen, lower alkyl, substituted lower alkyl, alkyl, substituted alkyl, aryl, substituted aryl, heteroaryl, substituted heteroaryl, provided, however, that at least one of R$^p$ and R$^{p'}$ is not hydrogen. R$^p$R$^{p'}$ in combination with the nitrogen may form an optionally substituted heterocyclic, or heteroaryl ring.

As used herein, the term "arylalkynyl" refers to aryl-substituted alkynyl groups and "substituted arylalkynyl" refers to arylalkynyl groups further bearing one or more substituents as set forth herein.

As used herein, the term "aralkyl" refers to alkyl as defined herein, where an alkyl hydrogen atom is replaced by an aryl as defined herein. Examples of aralkyl radicals include benzyl, phenethyl, 1-phenylpropyl, 2-phenylpropyl, 3-phenylpropyl, 1-naphthylpropyl, 2-naphthylpropyl, 3-naphthylpropyl, 3-naphthylbutyl, and the like.

As used herein, the term "aroyl" refers to aryl-carbonyl species such as benzoyl and "substituted aroyl" refers to aroyl groups further bearing one or more substituents as set forth herein.

As used herein, the term "arylalkyl" refers to aryl-substituted alkyl groups and "substituted arylalkyl" refers to arylalkyl groups further bearing one or more substituents as set forth herein.

As used herein, the term "aryl" alone or in combination refers to phenyl, naphthyl or fused aromatic heterocyclic optionally with a cycloalkyl of preferably 5-7, more preferably 5-6, ring members and/or optionally substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like.

As used herein, the term "arylcarbonylamino" denotes the group —NR$^q$C(O)R$^r$, wherein R$^q$ is hydrogen or lower alkyl or alkyl and R$^r$ is optionally substituted aryl.

As used herein, the term "arylene" refers to divalent aromatic groups typically having in the range of 6 up to 14 carbon atoms and "substituted arylene" refers to arylene groups further bearing one or more substituents as set forth herein.

As used herein, the term "aryloxy" denotes the group —OAr, where Ar is an aryl, or substituted aryl group.

As used herein, the term "arylsulfonylamino" denotes the group —NR$^q$S(O)$_2$R$^r$, where R$^q$ is hydrogen or lower alkyl, or alkyl and R$^r$ is optionally substituted aryl.

As used herein, the term "a carbamate group" denotes the group —O—C(O)—NR$_2$, where each R is independently H, alkyl, substituted alkyl, aryl, or substituted aryl as set forth herein.

As used herein, the term "dithiocarbamate group" denotes the group —S—C(S)—NR$_2$, where each R is independently H, alkyl, substituted alkyl, aryl, or substituted aryl as set forth herein.

As used herein, the term "carbocycle" refers to a saturated, unsaturated, or aromatic group having a single ring or multiple condensed rings composed of linked carbon atoms. The ring(s) can optionally be unsubstituted or substituted with, e.g., halogen, lower alkyl, alkoxy, alkylthio, acetylene, amino, amido, carboxyl, hydroxyl, aryl, aryloxy, heterocycle, hetaryl, substituted hetaryl, nitro, cyano, thiol, sulfamido, and the like.

As used herein, the term "cycloalkenyl" refers to cyclic ring-containing groups containing in the range of 3-20 carbon atoms and having at least one carbon-carbon double bond, and "substituted cycloalkenyl" refers to cycloalkenyl groups further bearing one or more substituents as set forth herein.

As used herein, the term "cycloalkyl" refers to a monocyclic or polycyclic alkyl group containing 3-15 carbon atoms, and "substituted cycloalkyl" refers to cycloalkyl groups further bearing one or more substituents as set forth herein.

As used herein, the term "cycloalkylene" refers to divalent ring-containing groups containing in the range of about 3-12 carbon atoms, and "substituted cycloalkylene" refers to cycloalkylene groups further bearing one or more substituents as set forth herein.

As used herein, the term "guanidinyl" denotes the group —N=C(NH$_2$)$_2$ and "substituted guanidinyl" denotes the group —N=C(NR$_2$)$_2$, where each R is independently H, alkyl, substituted alkyl, aryl, or substituted aryl as set forth herein.

As used herein, the term "halo" or "halogen" refers to all halogens, i.e., chloro (Cl), fluoro (F), bromo (Br), and iodo (I).

As used herein, the term "heteroaryl" refers to a monocyclic aromatic ring structure containing 5 or 6 ring atoms, or a bicyclic aromatic group having 8-10 atoms, containing one or more, preferably 1-4, more preferably 1-3, even more preferably 1-2 heteroatoms independently selected from the group O, S, and N, and optionally substituted with 1-3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl, or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like. Heteroaryl is also intended to include oxidized S or N, such as sulfinyl, sulfonyl, and N-oxide of a tertiary ring nitrogen. A carbon or nitrogen atom is the point of attachment of the heteroaryl ring structure such that a stable aromatic ring is retained. Examples of heteroaryl groups are phthalimide, pyridinyl, pyridazinyl, pyrazinyl, quinazolinyl, purinyl, indolyl, quinolinyl, pyrimidinyl, pyrrolyl, oxazolyl, thiazolyl, thienyl, isoxazolyl, oxathiadiazolyl, isothiazolyl, tetrazolyl, imidazolyl, triazinyl, furanyl, benzofuryl, indolyl, and the like. A substituted heteroaryl contains a substituent attached at an available carbon or nitrogen to produce a stable compound.

As used herein, the term "substituted heteroaryl" refers to a heterocycle optionally mono or poly substituted with one or more functional groups, e.g., halogen, lower alkyl, lower alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido, and the like.

As used herein, the term "heteroarylcarbonylamino" denotes the group —$NR^qC(O)R^r$, where $R^q$ is hydrogen or lower alkyl, and $R^r$ is optionally substituted aryl.

As used herein, the term "heteroaryloxy" denotes the group —OHet, where Het is an optionally substituted heteroaryl group.

As used herein, the term "heteroarylsulfonylamino" denotes the group —$NR^qS(O)_2R^s$, where $R^q$ is hydrogen or lower alkyl and $R^s$ is optionally substituted heteroaryl.

As used herein, the term "heterocycle" refers to a saturated, unsaturated, or aromatic group having a single ring (e.g., morpholino, pyridyl or furyl) or multiple condensed rings (e.g., naphthpyridyl, quinoxalyl, quinolinyl, indolizinyl or benzo[b]thienyl) and having carbon atoms and at least one hetero atom, such as N, O or S, within the ring, which can optionally be unsubstituted or substituted with, e.g., halogen, lower alkyl, lower alkoxy, alkylthio, acetylene, amino, amido, carboxyl, hydroxyl, aryl, aryloxy, heterocycle, hetaryl, substituted hetaryl, nitro, cyano, thiol, sulfamido, and the like.

As used herein, the term "substituted heterocycle" refers to a heterocycle substituted with 1 or more, e.g., 1, 2, or 3, substituents selected from the group consisting of optionally substituted alkyl, optionally substituted alkenyl, optionally substituted alkynyl, halo, hydroxy, alkoxy, alkylthio, alkylsulfinyl, alkylsulfonyl, acyloxy, aryl, substituted aryl, aryloxy, heteroaryloxy, amino, amido, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, acyl, carboxyl, heterocycle, substituted heterocycle, hetaryl, substituted hetaryl, nitro, cyano, thiol, sulfonamido, and oxo, attached at any available point to produce a stable compound.

As used herein, the term "hydrocarbyl" refers to any organic radical where the backbone thereof comprises carbon and hydrogen only. Thus, hydrocarbyl embraces alkyl, cycloalkyl, alkenyl, cycloalkenyl, alkynyl, aryl, alkylaryl, arylalkyl, arylalkenyl, alkenylaryl, arylalkynyl, alkynylaryl, and the like.

As used herein, the term "substituted hydrocarbyl" refers to any of the above-referenced hydrocarbyl groups further bearing one or more substituents selected from hydroxy, hydrocarbyloxy, substituted hydrocarbyloxy, alkylthio, substituted alkylthio, arylthio, substituted arylthio, amino, alkylamino, substituted alkylamino, carboxy, —C(S)SR, —C(O)SR, —$C(S)NR_2$, where each R is independently hydrogen, alkyl or substituted alkyl, nitro, cyano, halo, —$SO_3M$ or —$OSO_3M$, where M is H, Na, K, Zn, Ca, or meglumine, guanidinyl, substituted guanidinyl, hydrocarbyl, substituted hydrocarbyl, hydrocarbylcarbonyl, substituted hydrocarbylcarbonyl, hydrocarbyloxycarbonyl, substituted hydrocarbyloxycarbonyl, hydrocarbylcarbonyloxy, substituted hydrocarbylcarbonyloxy, acyl, acyloxy, heterocyclic, substituted heterocyclic, heteroaryl, substituted heteroaryl, heteroarylcarbonyl, substituted heteroarylcarbonyl, carbamoyl, monoalkylcarbamoyl, dialkylcarbamoyl, arylcarbamoyl, a carbamate group, a dithiocarbamate group, aroyl, substituted aroyl, organosulfonyl, substituted organosulfonyl, organosulfinyl, substituted alkylsulfinyl, alkylsulfonylamino, substituted alkylsulfonylamino, arylsulfonylamino, substituted arylsulfonylamino, a sulfonamide group, sulfuryl, and the like, including two or more of the above-described groups attached to the hydrocarbyl moiety by such linker/spacer moieties as —O—, —S—, —NR—, where R is hydrogen, alkyl or substituted alkyl, —C(O)—, —C(S)—, —C(=NR')—, —C(=CR'$_2$)—, where R' is alkyl or substituted alkyl, —O—C(O)—, —O—C(O)—O—, —O—C(O)—NR— (or —NR—C(O)—O—), —NR—C(O)—, —NR—C(O)—NR—, —S—C(O)—, —S—C(O)—O—, —S—C(O)—NR—, —O—$S(O)_2$—, —O—$S(O)_2$—O—, —O—$S(O)_2$—NR—, —O—S(O)—, —O—S(O)—O—, —O—S(O)—NR—, —O—NR—C(O)—, —O—NR—C(O)—O—, —O—NR—C(O)—NR—, —NR—O—C(O)—, —NR—O—C(O)—O—, —NR—O—C(O)—NR—, —O—NR—C(S)—, —O—NR—C(S)—O—, —O—NR—C(S)—NR—, —NR—O—C(S)—, —NR—O—C(S)—O—, —NR—O—C(S)—NR—, —O—C(S)—, —O—C(S)—O—, —O—C(S)—NR— (or —NR—C(S)—O—), —NR—C(S)—, —NR—C(S)—NR—, —S—$S(O)_2$—, —S—$S(O)_2$—O—, —S—$S(O)_2$—NR—, —NR—O—S(O)—, —NR—O—S(O)—O—, —NR—O—S(O)—NR—, —NR—O—$S(O)_2$—, —NR—O—$S(O)_2$—O—, —NR—O—$S(O)_2$—NR—, —O—NR—S(O)—, —O—NR—S(O)—O—, —O—NR—S(O)—NR—, —O—NR—$S(O)_2$—O—, —O—NR—$S(O)_2$—NR—, —O—NR—$S(O)_2$—, —O—$P(O)R_2$—, —S—$P(O)R_2$—, or —NR—$P(O)R_2$—, where each R is independently hydrogen, alkyl or substituted alkyl, and the like.

As used herein, the term "hydrocarbyloxy" denotes —O-hydrocarbyl groups containing 2-20 carbon atoms and "substituted hydrocarbyloxy" refers to hydrocarbyloxy groups further bearing one or more substituents as set forth herein.

As used herein, the term "hydrocarbylcarbonyl" refers to —C(O)-hydrocarbyl groups containing 2-20 carbon atoms and "substituted hydrocarbylcarbonyl" refers to hydrocarbylcarbonyl groups further bearing one or more substituents as set forth herein.

As used herein, the term "hydrocarbyloxycarbonyl" refers to —C(O)—O— hydrocarbyl containing 2-20 carbon atoms and "substituted hydrocarbyloxycarbonyl" refers to hydrocarbyloxycarbonyl groups further bearing one or more substituents as set forth herein.

As used herein, the term "hydrocarbylcarbonyloxy" refers to —O—C(O)— hydrocarbyl groups 2-20 carbon atoms and "substituted hydrocarbylcarbonyloxy" refers to hydrocarbylcarbonyloxy groups further bearing one or more substituents as set forth herein.

As used herein, the term "hydrocarbylene" refers to any divalent organic radical wherein the backbone thereof comprises carbon and hydrogen only. Thus, hydrocarbylene embraces alkylene, cycloalkylene, alkenylene, cycloalkenylene, alkynylene, arylene, alkylarylene, arylalkylene, arylalkenylene, alkenylarylene, arylalkynylene, alkynylarylene, and the like, and "substituted hydrocarbylene" refers to any of the above-referenced hydrocarbylene groups further bearing one or more substituents as set forth herein.

As used herein, the term "hydroxyl" or "hydroxy" refers to the group —OH.

As used herein, the term "organosulfinyl" denotes the group —S(O)-organo, where organo embraces alkyl-, alkoxy-, alkylamino-, and aryl moieties, as well as substituted alkyl-, alkoxy-, alkylamino-, and aryl moieties.

As used herein, the term "organosulfonyl" denotes the group —S(O)$_2$-organo, where organo embraces alkyl-, alkoxy- and alkylamino-moieties, as well as substituted alkyl-, alkoxy- or alkylamino-moieties.

As used herein, the term "oxo" refers to an oxygen substituent double bonded to the attached carbon.

As used herein, the term "sulfinyl" denotes the group —S(O)—.

As used herein, the term "substituted sulfinyl" denotes the group —S(O)R$^t$, where R$^t$ is lower alkyl, substituted lower alkyl, cycloalkyl, substituted cycloalkyl, cycloalkylalkyl, substituted cycloalkylalkyl, heterocyclyl, substituted heterocyclyl, heterocyclylalkyl, substituted hetereocyclylalkyl, aryl, substituted aryl, heteroaryl, substituted heteroaryl, heteroaralkyl, substituted heteroaralkyl, aralkyl, or substituted aralkyl.

As used herein, the term "sulfonyl" denotes the group —S(O)$_2$—.

As used herein, the term "substituted sulfonyl" denotes the group —S(O)$_2$R$^t$, where R$^t$ is lower alkyl, substituted lower alkyl, cycloalkyl, substituted cycloalkyl, cycloalkylalkyl, substituted cycloalkylalkyl, heterocyclyl, substituted heterocyclyl, heterocyclylalkyl, substituted hetereocyclylalkyl, aryl, substituted aryl, heteroaryl, substituted heteroaryl, heteroaralkyl, substituted heteroaralkyl, aralkyl, or substituted aralkyl.

As used herein, the term "sulfonylamino" denotes the group —NR'S(O)$_2$— where R$^q$ is hydrogen or lower alkyl.

As used herein, the term "substituted sulfonylamino" denotes the group —NR$^q$S(O)$_2$R$^u$, where R$^q$ is hydrogen or lower alkyl and R$^u$ is lower alkyl, substituted lower alkyl, cycloalkyl, substituted cycloalkyl, heterocyclyl, substituted heterocyclyl, aryl, substituted aryl, heteroaryl, substituted heteroaryl, heteroaralkyl, substituted heteroaralkyl, aralkyl, or substituted aralkyl.

As used herein, the term "sulfuryl" denotes the group —S(O)$_2$—.

As used herein in connection with numerical values, the term "approximately" or "about" means 10% of the indicated value.

BRIEF DESCRIPTION OF THE FIGURES

FIG. 3A depicts amplification curves of a six-fold dilution series of a ligation product, including a control (NTC) from a ligation performed in the absence of template. FIG. 3B depicts dissociation curve from the reactions performed in FIG. 3A. FIG. 3C depicts a standard curve in which the Ct values extracted from the standard curve were plotted against the dilution factor.

FIG. 8 shows tables of relative ligation yields using sugar and backbone modified acceptor strands in combination with different modified ATP cofactors. These values are relative to the ligation yields using natural acceptor strands and ATP with matched (T-A) and mismatched (T-C) base pairs at the 3'-end of the acceptor strand, as described in Example 1. In the matched case (T-A), values in dot-shaded cells represent greater than 0.85 relative ligation yield, values in unshaded cells represent 0.70-0.85 relative ligation yield, and values in gray-shaded cells represent 0-0.70 relative ligation yield. In the mismatched case (T-C), values in dot-shaded cells represent 0.0-0.01 relative ligation yield, values in unshaded cells represent 0.01-0.10 relative ligation yield, and values in gray-shaded cells represent 0.10-1.00 relative ligation yield. Combinations with preferred performance criteria have greater than 0.85 relative yield in the matched case (T-A) (e.g., dot-shaded cells in FIG. 8, top chart) and less than 0.01 relative ligation yield in the presence of a mismatched template (T-C) (e.g., dot-shaded cells in FIG. 8, bottom chart).

DETAILED DESCRIPTION OF THE INVENTION

Figure 1:
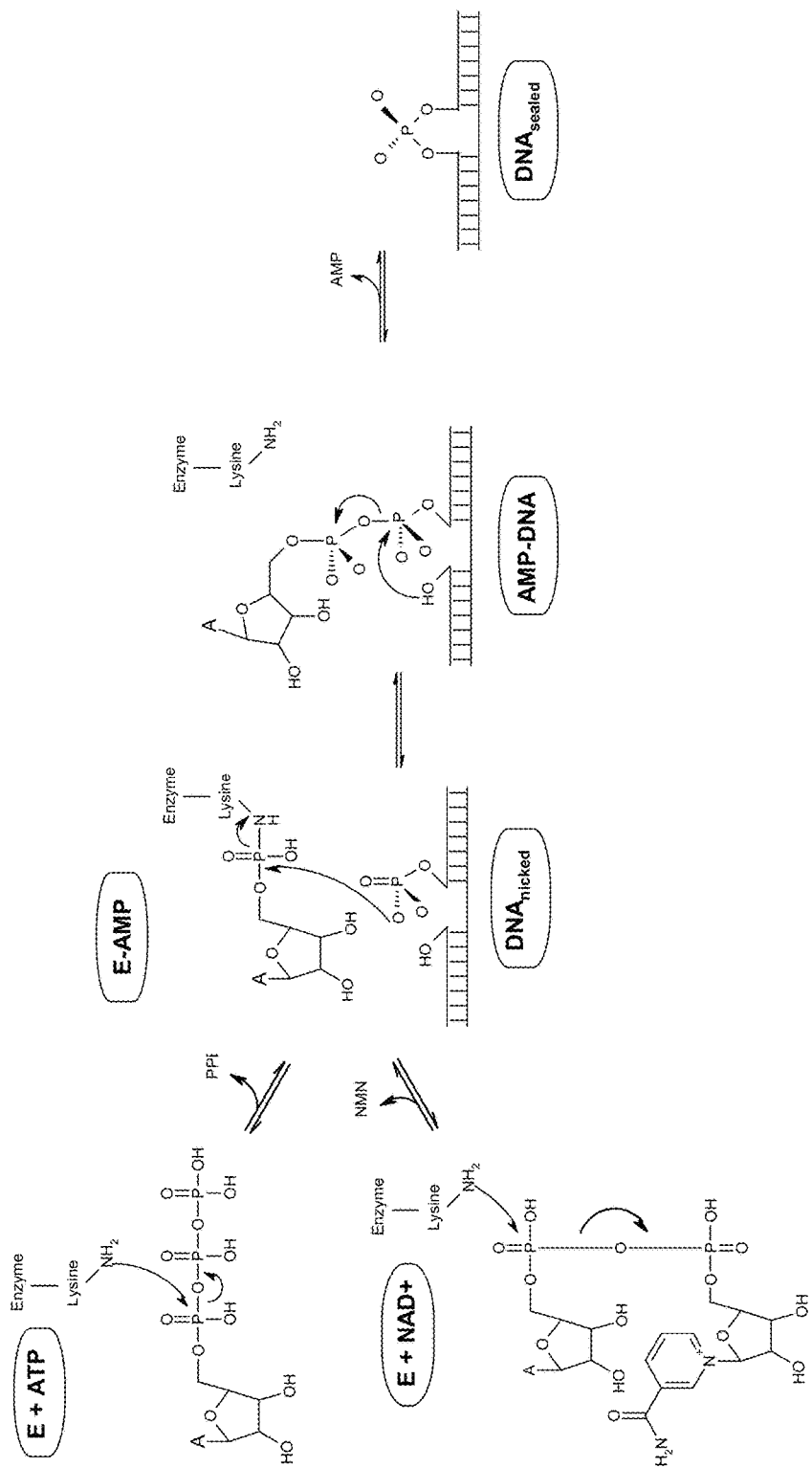
FIG. 1 is a schematic representation of the mechanism of phosphodiester bond formation by ATP-dependent and NAD+-dependent DNA ligases.

A nucleic acid ligation reaction involves (a) adenylation of the ligase enzyme, (b) hybridization of donor and acceptor polynucleotides to a target nucleic acid followed by (c) transfer of the adenylate to the donor strand and ligation to form a joined, complementary copy of the nucleic acid sequence by a nucleic acid ligase. However, ligation of donors and acceptors can occur 1) when the donor and or acceptor has a mismatch (noncomplementary) relative to the template nucleic acid or 2) in the absence of template nucleic acid.

The methods and compositions herein provide improved methods and compositions for nucleic acid ligation. In particular aspects, the methods and compositions are directed to the use of modified ligation components in enzymatic ligation reactions. In other aspects, the process of nucleic acid ligation employs one or more modified cofactor, modified donor, and/or modified acceptor, the presence of which impairs the formation of undesired ligation products in the absence of template or in the presence of mismatches.

Modified Ligase Cofactors

Certain aspects and embodiments of the compositions and methods provided herein include at least one modified ligase cofactor. In preferred embodiments, the modified ligase cofactor is a modified ATP having one or more substitution groups.

In embodiments of the aspects herein, modified ATPs and derivatives thereof in accordance with the invention provide compounds of Formula IA:

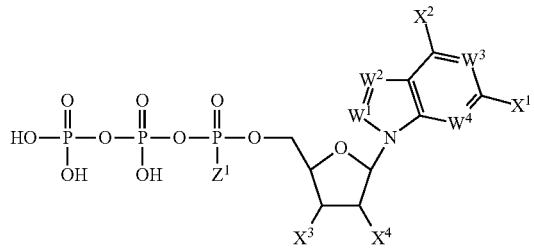

wherein:
$W^1$, $W^2$, $W^3$, and $W^4$ are each independently selected from the group consisting of N, $CR^1$, and $N^+R^1$;
each $R^1$ is independently selected from the group consisting of H, F, Cl, Br, I, $OR^2$, $SR^2$, $SeR^2$, $NR^2R^3$, $N_3$, $C(Y)R^4$, substituted or non-substituted alkyl, alkenyl, alkynyl, aryl, and aralkyl,
wherein any substituent may each optionally contain one or more heteroatoms;
$Z^1$ is selected from the group consisting of H, F, $R^2$, $OR^2$, $SR^2$, $SeR^2$, $NR^2R^3$, $NR^2OR^2$, $NR^2$—$NR^2R^3$, CN, $N_3$, $(BH_3)^-M^+$, and $C(Y)R^4$;
$M^+$ is a cation;
each $R^2$ and each $R^3$ is independently selected from the group consisting of H or substituted or non-substituted alkyl, alkenyl, alkynyl, aryl, and aralkyl,
wherein any substituent may each optionally contain one or more heteroatoms;
each $R^4$ is selected from the group consisting of H, F, Cl, Br, $OR^2$, $SR^2$, $SeR^2$, $NR^2R^3$, $C(Y)R^2$ and substituted or non-substituted alkyl, alkenyl, alkynyl, aryl, and aralkyl,
wherein any substituent may each optionally contain one or more heteroatoms;
each Y is selected from the group consisting of O, S, Se, $CR^1R^1$, and $NR^1$; and
$X^1$, $X^2$, $X^3$, and $X^4$ are each independently selected from the group consisting of $R^1$, $NR^2OR^2$, $NR^2$—$NR^2R^3$, CN, $N_3$, NO, $NO_2$, NCO, NCS, OCN, SCN, and $SSR^2$.

Preferred embodiments of modified ATP have the structure:

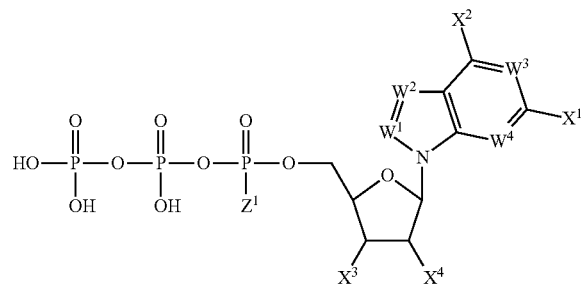

wherein:
$W^1$, $W^2$, $W^3$, and $W^4$ are each independently selected from the group consisting of N, $N^+$—$CH_3$, $N^+$—$CH_2CH_3$, $N^+$—$CH_2CH_2CH_3$, $N^+$—$CH_2CH_2CH_2CH_3$, $N^+$—$CH(CH_3)_2$, CH, C—$CH_3$, C—$CH_2CH_3$, C—$CH_2CH_2CH_3$, C—$CH_2CH_2CH_2CH_3$, C—$CH(CH_3)_2$, C—$NH_2$, C—$NHCH_3$, C—$N(CH_3)_2$, C—$N_3$, and C—OH;
$Z^1$ is selected from the group consisting of H, F, $CH_3$, phenyl, $OCH_3$, $OCH_2CH_3$, $OCH_2CH_2CH_3$, $OCH_2CH_2CH_2CH_3$, $OCH(CH_3)_2$, SH, $SCH_3$, $SCH_2CH_3$, $SCH_2CH_2CH_3$, $SCH_2CH_2CH_2CH_3$, $SCH(CH_3)_2$, SeH, $SeCH_3$, $SeCH_2CH_3$, $SeCH_2CH_2CH_3$, $SeCH_2CH_2CH_2CH_3$, $SeCH(CH_3)_2$, $NH_2$, $NHCH_3$, $NCH_3CH_3$, $NHOCH_3$, $NCH_3OCH_3$, NH—$NH_2$, NH—$NHCH_3$, NH—$NCH_3CH_3$, $NCH_3$—$NH_2$, $NCH_3$—$NHCH_3$, $NCH_3$—$NCH_3CH_3$, CN, $N_3$, and $(BH_3)^-M^+$;
$M^+$ is a cation;
$X^1$ is selected from the group consisting of H, $NH_2$, OH, $NHCH_3$, and $N(CH_3)_2$;
$X^2$ is selected from the group consisting of H, Cl, OH, $NH_2$, $NHCH_3$, and $N(CH_3)_2$;
$X^3$ is selected from the group consisting of H, F, $CH_3$, OH, SH, $OCH_3$, $NH_2$, $NHCH_3$, $N(CH_3)_2$, and $N_3$; and
$X^4$ is selected from the group consisting of H, F, OH, $OCH_3$, $NH_2$, $NHCH_3$, $N(CH_3)_2$, and $N_3$.

Preferred embodiments of modified ATP have the structure:

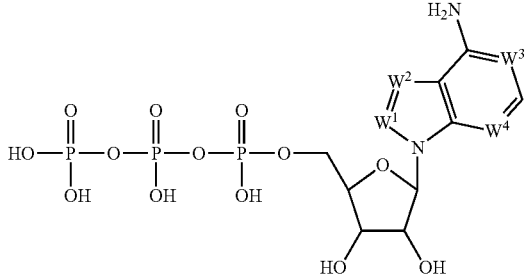

wherein:
$W^1$, $W^2$, $W^3$, and $W^4$ are each independently selected from the group consisting of N, $CR^1$, and $N^+R^1$; and
each $R^1$ is independently selected from the group consisting of H, F, Cl, Br, I, $OR^2$, $SR^2$, $SeR^2$, $NR^2R^3$, $N_3$, $C(Y)R^4$, and substituted or non-substituted alkyl, alkenyl, alkynyl, aryl, and aralkyl,
wherein any substituent may each optionally contain one or more heteroatoms;
each $R^2$ and each $R^3$ is independently selected from the group consisting of H or substituted or non-substituted alkyl, alkenyl, alkynyl, aryl, and aralkyl,
wherein any substituent may each optionally contain one or more heteroatoms;
each $R^4$ is selected from the group consisting of H, F, Cl, Br, $OR^2$, $SR^2$, $SeR^2$, $NR^2R^3$, $C(Y)R^2$ and substituted or non-substituted alkyl, alkenyl, alkynyl, aryl, and aralkyl,
wherein any substituent may each optionally contain one or more heteroatoms; and
each Y is selected from the group consisting of O, S, Se, $CR^1R^1$, and $NR^1$.

Preferred embodiments of modified ATP have the structure:

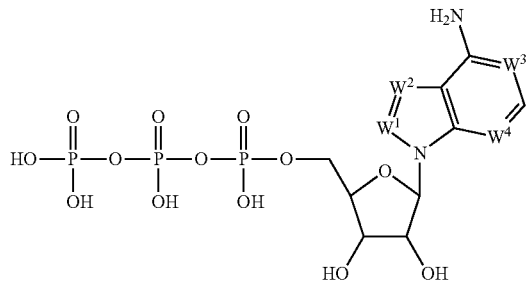

wherein:
$W^1$, $W^2$, $W^3$, and $W^4$ are each independently selected from the group consisting of N, $N^+$—$CH_3$, $N^+$—$CH_2CH_3$, $N^+$—$CH_2CH_2CH_3$, $N^+$—$CH_2CH_2CH_2CH_3$, $N^+$—$CH(CH_3)_2$, CH, C—$CH_3$, C—$CH_2CH_3$, C—$CH_2CH_2CH_3$, C—$CH_2CH_2CH_2CH_3$, C—$CH(CH_3)_2$, C—$NH_2$, C—$NHCH_3$, C—$N(CH_3)_2$, C—$N_3$, and C—OH.

Preferred embodiments of modified ATP have the structure:

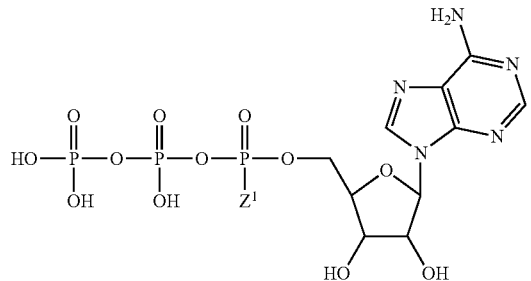

wherein:
$Z^1$ is selected from the group consisting of H, F, $R^1$, $OR^1$, $SR^1$, $SeR^1$, $NR^1R^2$, $NR^1OR^1$, $NR^1$—$NR^1R^1$, CN, $N_3$, $(BH_3)^-M^+$, and $C(Y)R^2$;
$M^+$ is a cation;
each $R^1$ is independently selected from the group consisting of H or substituted or non-substituted alkyl, alkenyl, alkynyl, aryl, and aralkyl,
wherein any substituent may each optionally contain one or more heteroatoms;
each $R^2$ is selected from the group consisting of H, F, Cl, Br, $OR^1$, $SR^1$, $SeR^1$, $NR^1R^1$, $C(Y)R^1$ and substituted or non-substituted alkyl, alkenyl, alkynyl, aryl, and aralkyl,
wherein any substituent may each optionally contain one or more heteroatoms; and each Y is selected from the group consisting of O, S, Se, CR$^1$R$^1$, and NR$^1$.

Preferred embodiments of modified ATP have the structure:

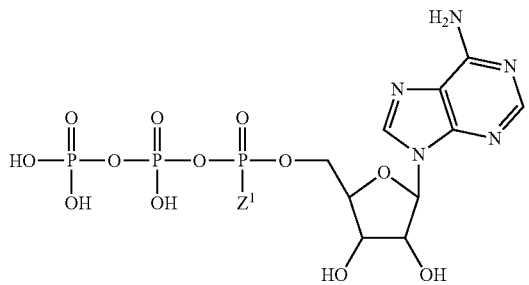

wherein:

Z$^1$ is selected from the group consisting of H, F, CH$_3$, phenyl, OCH$_3$, OCH$_2$CH$_3$, OCH$_2$CH$_2$CH$_3$, OCH$_2$CH$_2$CH$_2$CH$_3$, OCH(CH$_3$)$_2$, SH, SCH$_3$, SCH$_2$CH$_3$, SCH$_2$CH$_2$CH$_3$, SCH$_2$CH$_2$CH$_2$CH$_3$, SCH(CH$_3$)$_2$, SeH, SeCH$_3$, SeCH$_2$CH$_3$, SeCH$_2$CH$_2$CH$_3$, SeCH$_2$CH$_2$CH$_2$CH$_3$, SeCH(CH$_3$)$_2$, NH$_2$, NHCH$_3$, NCH$_3$CH$_3$, NHOCH$_3$, NCH$_3$OCH$_3$, NH—NH$_2$, NH—NHCH$_3$, NH—NCH$_3$CH$_3$, NCH$_3$—NH$_2$, NCH$_3$—NHCH$_3$, NCH$_3$—NCH$_3$CH$_3$, CN, N$_3$, and (BH$_3$)$^-$M$^+$;

M$^+$ is a cation

Preferred embodiments of modified ATP have the structure:

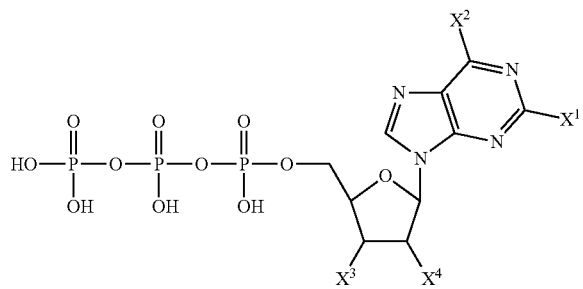

wherein:

X$^1$, X$^2$, X$^3$, and X$^4$ are each independently selected from the group consisting of R$^1$, NR$^2$R$^3$, NR$^2$OR$^2$, NR$^2$—NR$^2$R$^3$, CN, N$_3$, NO, NO$_2$, NCO, NCS, OCN, SCN, and SSR$^2$;

each R$^1$ is independently selected from the group consisting of H, F, Cl, Br, I, OR$^2$, SR$^2$, SeR$^2$, NR$^2$R$^3$, C(Y)R$^4$, and substituted or non-substituted alkyl, alkenyl, alkynyl, aryl, and aralkyl,
    wherein any substituent may each optionally contain one or more heteroatoms;

each R$^2$ and each R$^3$ is independently selected from the group consisting of H or substituted or non-substituted alkyl, alkenyl, alkynyl, aryl, and aralkyl,
    wherein any substituent may each optionally contain one or more heteroatoms;

each R$^4$ is selected from the group consisting of H, F, Cl, Br, OR$^2$, SR$^2$, SeR$^2$, NR$^2$R$^3$, C(Y)R$^2$ and substituted or non-substituted alkyl, alkenyl, alkynyl, aryl, and aralkyl,
    wherein any substituent may each optionally contain one or more heteroatoms; and each Y is selected from the group consisting of O, S, Se, CR$^1$R$^1$, and NR$^1$.

Preferred embodiments of modified ATP have the structure:

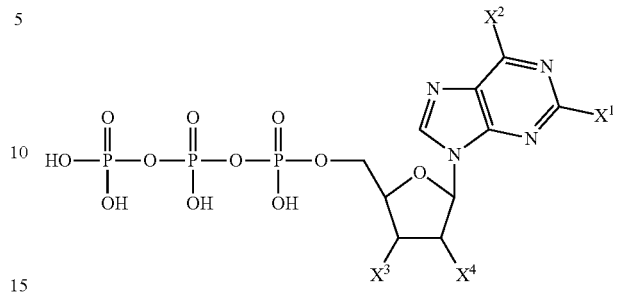

wherein:

X$^1$ is selected from the group consisting of H, NH$_2$, OH, NHCH$_3$, and N(CH$_3$)$_2$;

X$^2$ is selected from the group consisting of H, Cl, OH, NH$_2$, NH(CH$_3$), and N(CH$_3$)$_2$;

X$^3$ is selected from the group consisting of H, F, CH$_3$, OH, SH, OCH$_3$, NH$_2$, NHCH$_3$, N(CH$_3$)$_2$, and N$_3$; and X$^4$ is selected from the group consisting of H, F, OH, SH, OCH$_3$, NH$_2$, NHCH$_3$, N(CH$_3$)$_2$, and N$_3$.

Preferred embodiments of modified ATP have the structure:

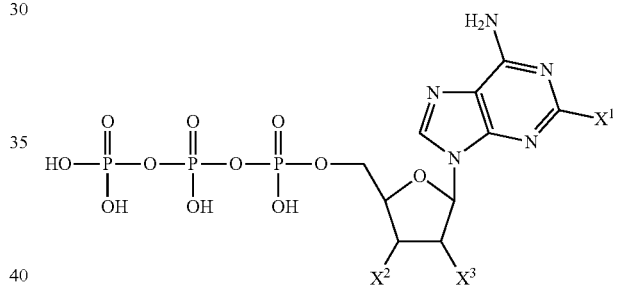

wherein:

X$^1$, X$^2$, and X$^3$ are each independently selected from the group consisting of R$^1$, NR$^2$OR$^2$, NR$^2$—NR$^2$R$^3$, CN, N$_3$, NO, NO$_2$, NCO, NCS, OCN, SCN, and SSR$^2$;

each R$^1$ is independently selected from the group consisting of H, F, Cl, Br, I, OR$^2$, SR$^2$, SeR$^2$, NR$^2$R$^3$, N$_3$, C(Y)R$^4$, substituted or non-substituted alkyl, alkenyl, alkynyl, aryl, and aralkyl,
    wherein any substituent may each optionally contain one or more heteroatoms;

each R$^2$ and each R$^3$ is independently selected from the group consisting of H or substituted or non-substituted alkyl, alkenyl, alkynyl, aryl, and aralkyl,
    wherein any substituent may each optionally contain one or more heteroatoms;

each R$^4$ is selected from the group consisting of H, F, Cl, Br, OR$^2$, SR$^2$, SeR$^2$, NR$^2$R$^3$, C(Y)R$^2$ and substituted or non-substituted alkyl, alkenyl, alkynyl, aryl, and aralkyl,
    wherein any substituent may each optionally contain one or more heteroatoms;

each Y is selected from the group consisting of O, S, Se, CR$^1$R$^1$, and NR$^1$.

Preferred embodiments of modified ATP have the structure:

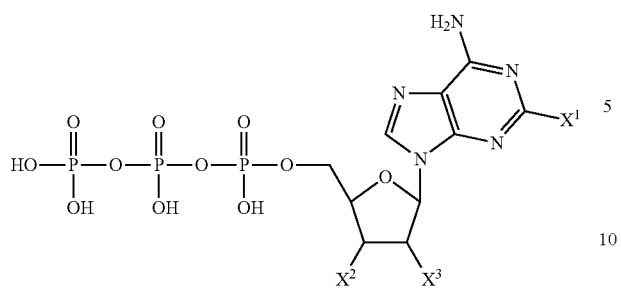

wherein:
$X^1$ is selected from the group consisting of H, $NH_2$, OH, $NHCH_3$, and $N(CH_3)_2$;
$X^2$ is selected from the group consisting of H, F, $CH_3$, OH, SH, $OCH_3$, $NH_2$, $NHCH_3$, $N(CH_3)_2$, and $N_3$; and
$X^3$ is selected from the group consisting of H, F, OH, SH, $OCH_3$, $NH_2$, $NHCH_3$, $N(CH_3)_2$, and $N_3$.

Preferred embodiments of modified ATP have the structure:

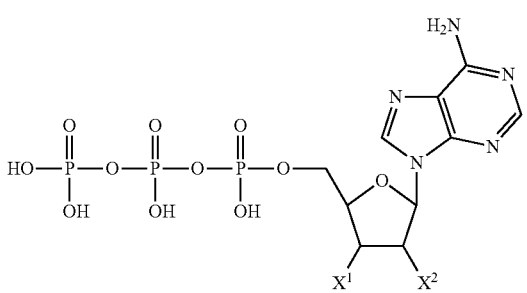

wherein:
$X^1$ and $X^2$ are each independently selected from the group consisting of $R^1$, $NR^2OR^2$, $NR^2$—$NR^2R^3$, CN, $N_3$, NO, $NO_2$, NCO, NCS, OCN, SCN, and $SSR^2$;
each $R^1$ is independently selected from the group consisting of H, F, Cl, Br, I, $OR^2$, $SR^2$, $SeR^2$, $NR^2R^3$, $N_3$, $C(Y)R^4$, substituted or non-substituted alkyl, alkenyl, alkynyl, aryl, and aralkyl,
  wherein any substituent may each optionally contain one or more heteroatoms;
each $R^2$ and each $R^3$ is independently selected from the group consisting of H or substituted or non-substituted alkyl, alkenyl, alkynyl, aryl, and aralkyl,
  wherein any substituent may each optionally contain one or more heteroatoms;
each $R^4$ is selected from the group consisting of H, F, Cl, Br, $OR^2$, $SR^2$, $SeR^2$, $NR^2R^3$, $C(Y)R^2$ and substituted or non-substituted alkyl, alkenyl, alkynyl, aryl, and aralkyl,
  wherein any substituent may each optionally contain one or more heteroatoms;
each Y is selected from the group consisting of O, S, Se, $CR^1R^1$, and $NR^1$.

Preferred embodiments of modified ATP have the structure:

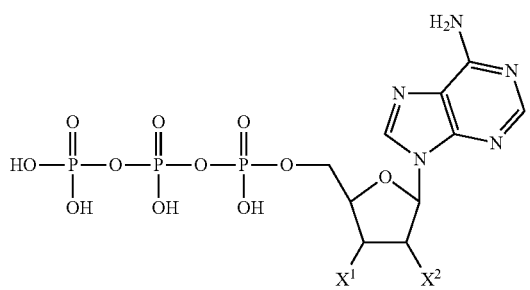

wherein:
$X^1$ is selected from the group consisting of H, F, $CH_3$, OH, SH, $OCH_3$, $NH_2$, $NHCH_3$, $N(CH_3)_2$, and $N_3$; and
$X^2$ is selected from the group consisting of H, F, OH, SH, $OCH_3$, $NH_2$, $NHCH_3$, $N(CH_3)_2$, and $N_3$.

Preferred embodiments of modified ATP have the structure:

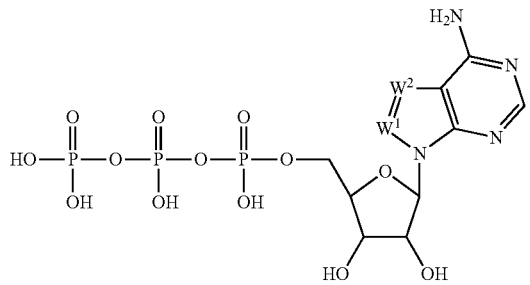

wherein:
$W^1$ and $W^2$ are each independently selected from the group consisting of N, $CR^1$, and $N^+R^1$; and
each $R^1$ is independently selected from the group consisting of H, F, Cl, Br, I, $OR^2$, $SR^2$, $SeR^2$, $NR^2R^3$, $N_3$, $C(Y)R^4$, and substituted or non-substituted alkyl, alkenyl, alkynyl, aryl, and aralkyl,
  wherein any substituent may each optionally contain one or more heteroatoms;
each $R^2$ and each $R^3$ is independently selected from the group consisting of H or substituted or non-substituted alkyl, alkenyl, alkynyl, aryl, and aralkyl,
  wherein any substituent may each optionally contain one or more heteroatoms;
each $R^4$ is selected from the group consisting of H, F, Cl, Br, $OR^2$, $SR^2$, $SeR^2$, $NR^2R^3$, $C(Y)R^2$ and substituted or non-substituted alkyl, alkenyl, alkynyl, aryl, and aralkyl,
  wherein any substituent may each optionally contain one or more heteroatoms;
each Y is selected from the group consisting of O, S, Se, $CR^1R^1$, and $NR^1$.

Preferred embodiments of modified ATP have the structure:

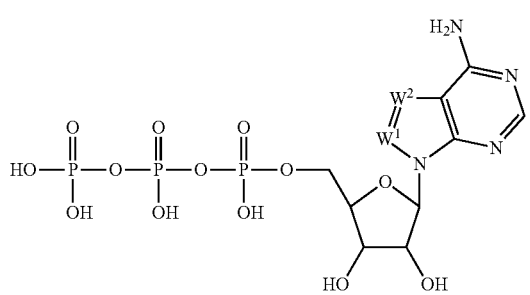

wherein:

W¹ and W² are each independently selected from the group consisting of N, N⁺—CH₃, N⁺—CH₂CH₃, N⁺—CH₂CH₂CH₃, N⁺—CH₂CH₂CH₂CH₃, N⁺—CH(CH₃)₂, CH, C—N₃, C—CH₃, C—CH₂CH₃, C—CH₂CH₂CH₃, C—CH₂CH₂CH₂CH₃, C—CH(CH₃)₂, C—NH₂, C—NHCH₃, C—N(CH₃)₂, and C—OH.

Certain preferred embodiments of modified ATP are as follows.

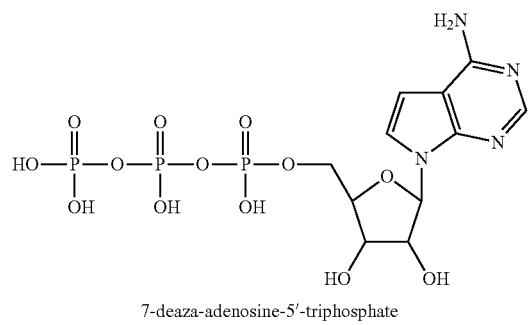

7-deaza-adenosine-5′-triphosphate

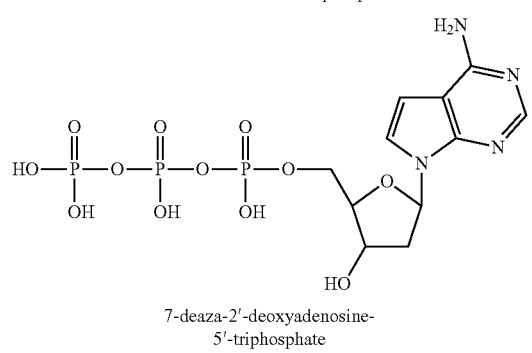

7-deaza-2′-deoxyadenosine-
5′-triphosphate

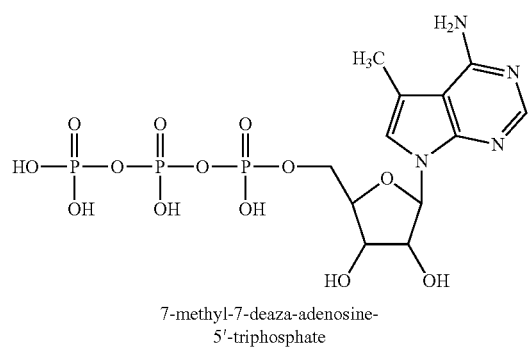

7-methyl-7-deaza-adenosine-
5′-triphosphate

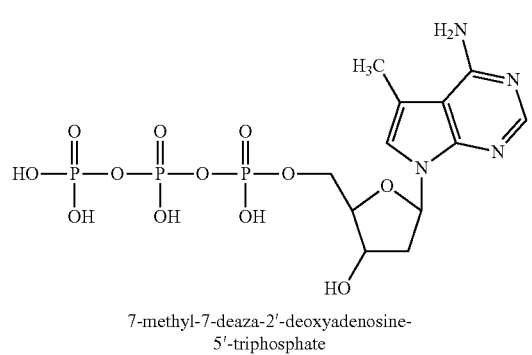

7-methyl-7-deaza-2′-deoxyadenosine-
5′-triphosphate

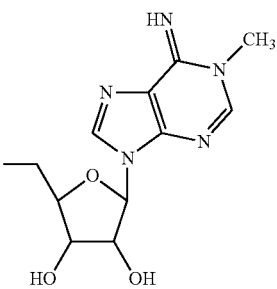

N1-methyl-adenosine-5′-triphosphate

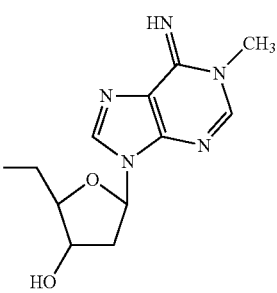

N1-methyl-2′-deoxyadenosine-
5′-triphosphate

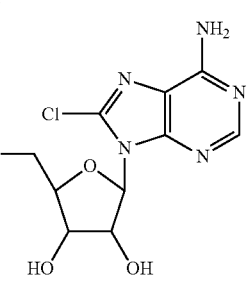

8-chloro-adenosine-
5′-triphosphate

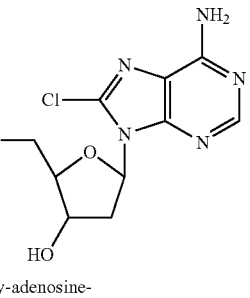

8-chloro-2′-deoxy-adenosine-
5′-triphosphate

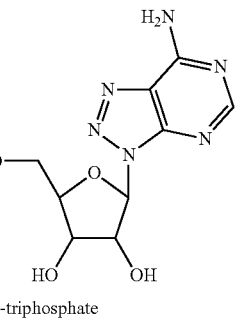

8-aza-adenosine-5′-triphosphate

-continued

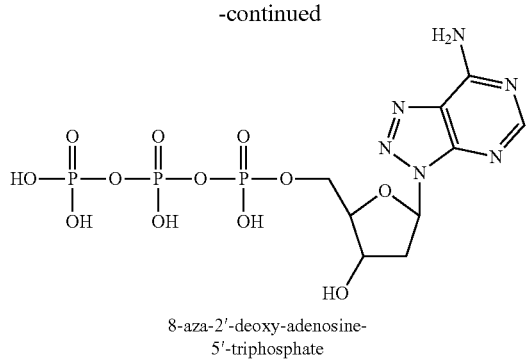

8-aza-2'-deoxy-adenosine-
5'-triphosphate

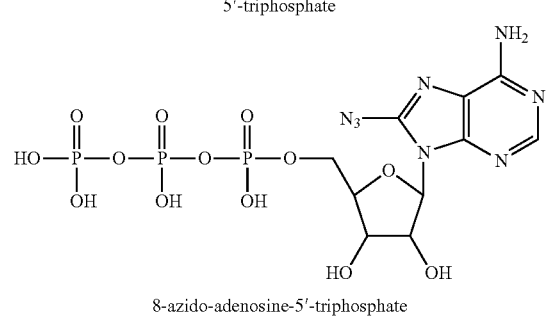

8-azido-adenosine-5'-triphosphate

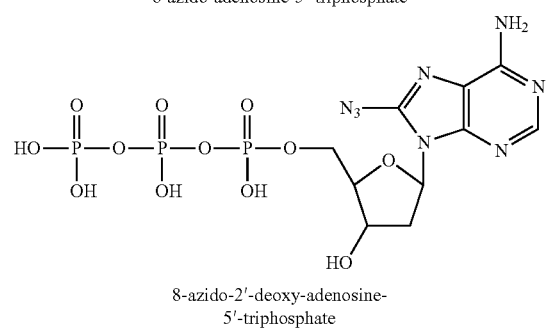

8-azido-2'-deoxy-adenosine-
5'-triphosphate

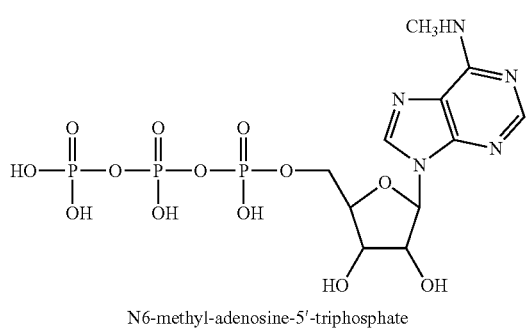

N6-methyl-adenosine-5'-triphosphate

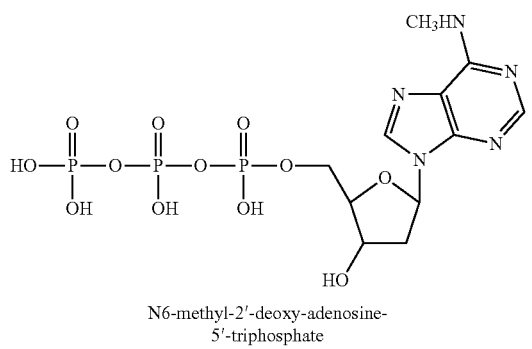

N6-methyl-2'-deoxy-adenosine-
5'-triphosphate

-continued

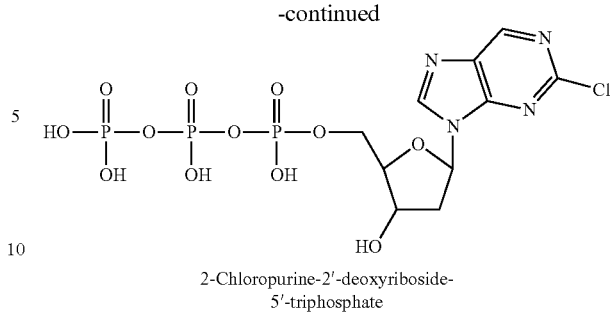

2-Chloropurine-2'-deoxyriboside-
5'-triphosphate

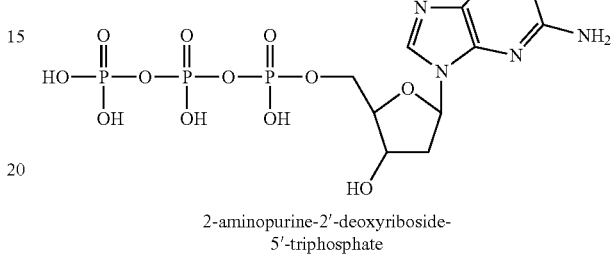

2-aminopurine-2'-deoxyriboside-
5'-triphosphate

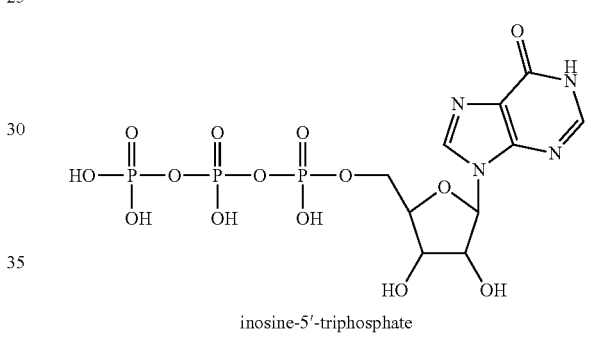

inosine-5'-triphosphate

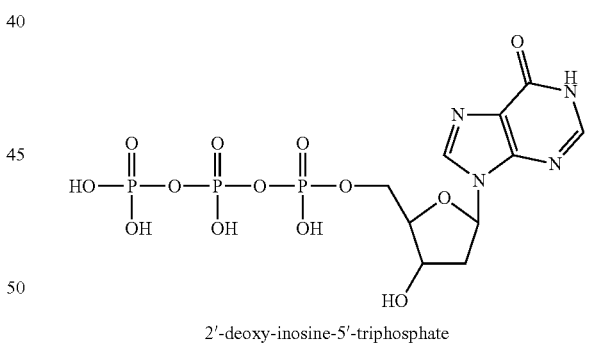

2'-deoxy-inosine-5'-triphosphate

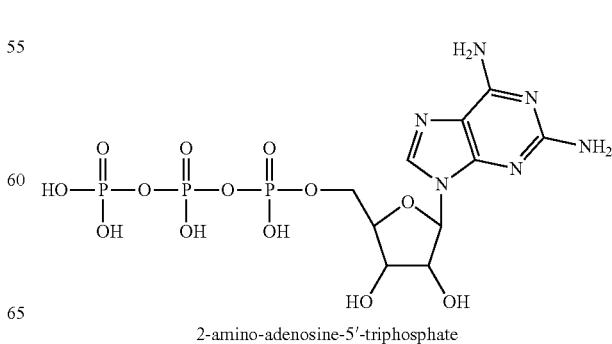

2-amino-adenosine-5'-triphosphate

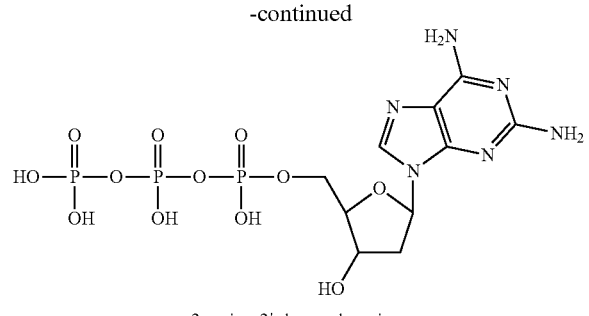

2-amino-2'-deoxyadenosine-
5'-triphosphate

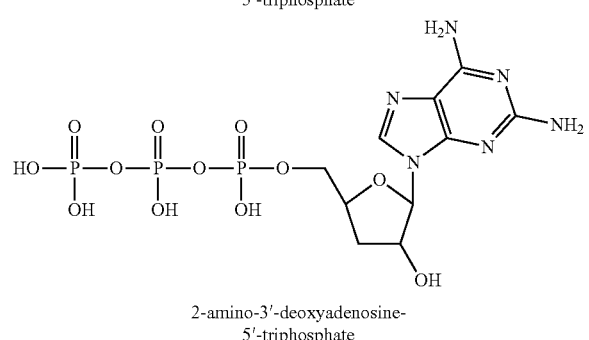

2-amino-3'-deoxyadenosine-
5'-triphosphate

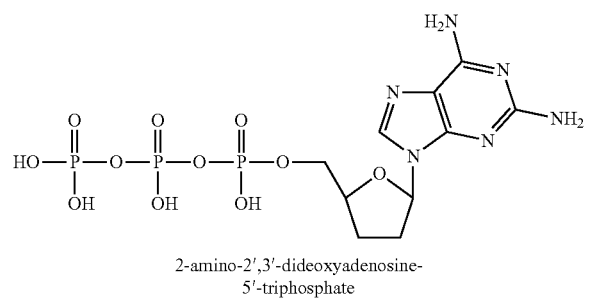

2-amino-2',3'-dideoxyadenosine-
5'-triphosphate

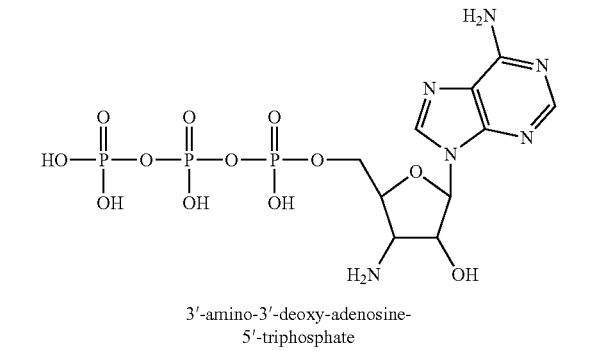

3'-amino-3'-deoxy-adenosine-
5'-triphosphate

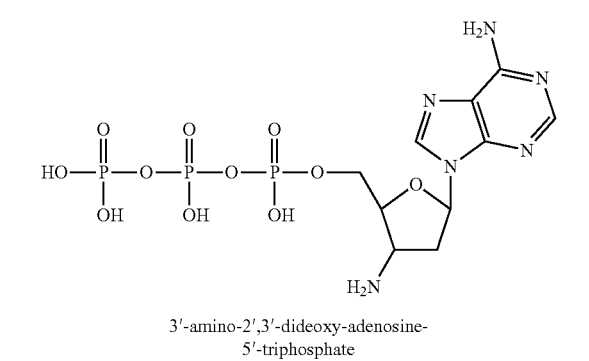

3'-amino-2',3'-dideoxy-adenosine-
5'-triphosphate

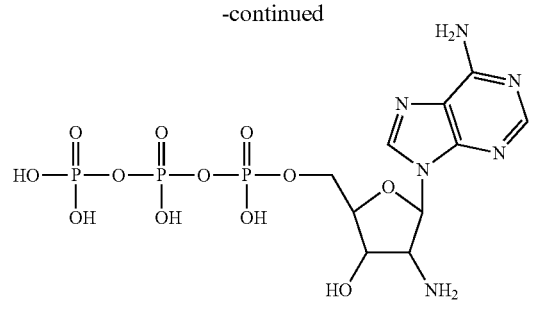

2'-amino-2'-deoxy-adenosine-
5'-triphosphate

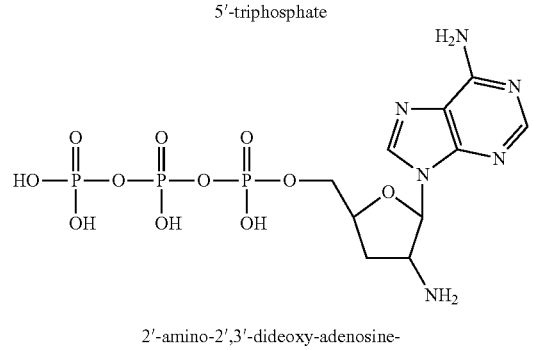

2'-amino-2',3'-dideoxy-adenosine-
5'-triphosphate

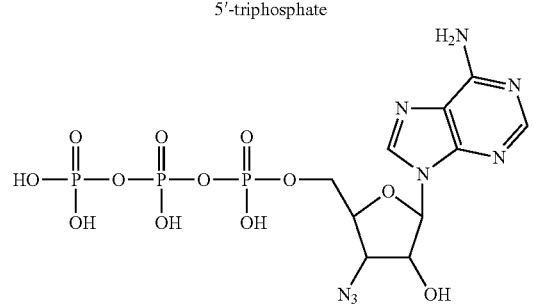

3'-azido-3'-deoxy-adenosine-
5'-triphosphate

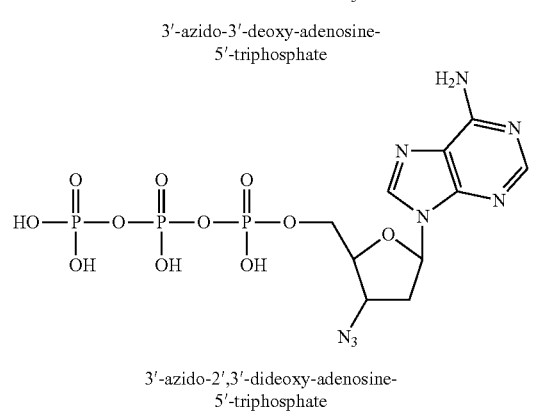

3'-azido-2',3'-dideoxy-adenosine-
5'-triphosphate

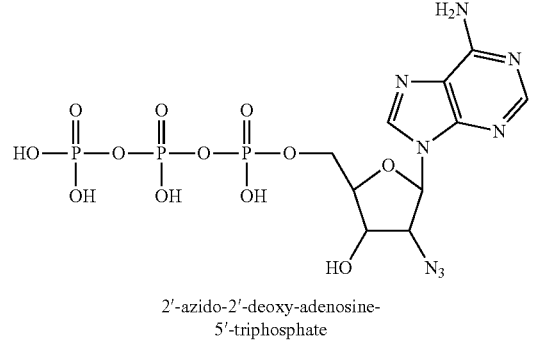

2'-azido-2'-deoxy-adenosine-
5'-triphosphate

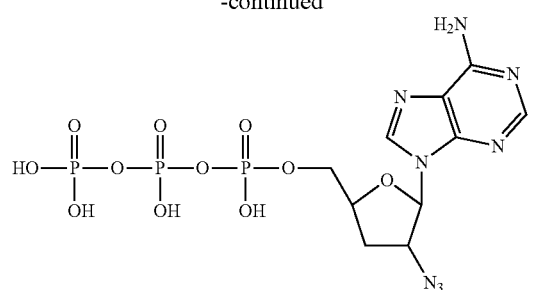

2'-azido-2',3'-dideoxy-adenosine-
5'-triphosphate

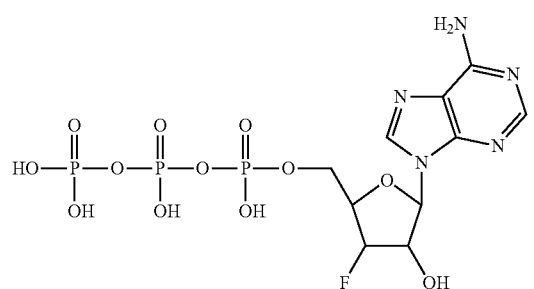

3'-fluoro-3'-deoxy-adenosine-
5'-triphosphate

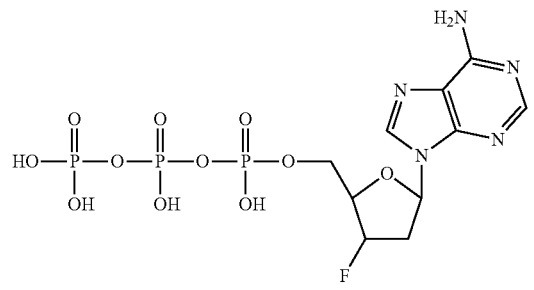

3'-fluoro-2',3'-dideoxy-adenosine-
5'-triphosphate

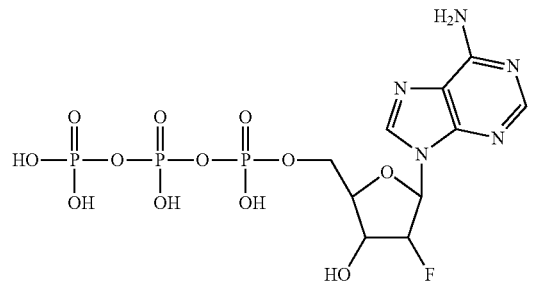

2'-fluoro-2'-deoxy-adenosine-
5'-triphosphate

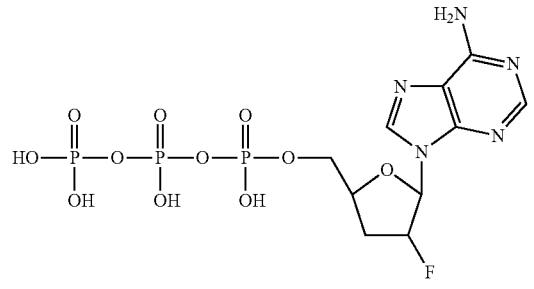

2'-fluoro-2',3'-dideoxy-adenosine-
5'-triphosphate

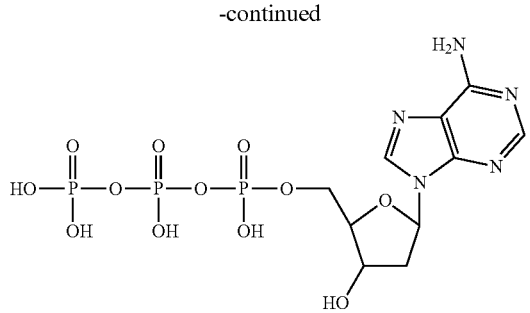

2'-deoxy-adenosine-
5'-triphosphate

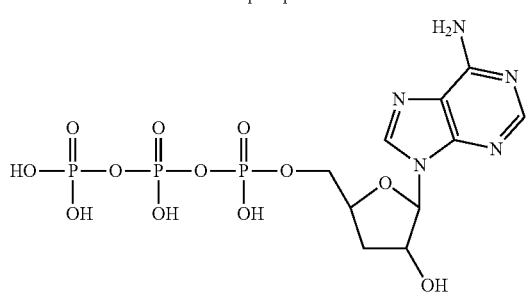

3'-deoxy-adenosine-
5'-triphosphate

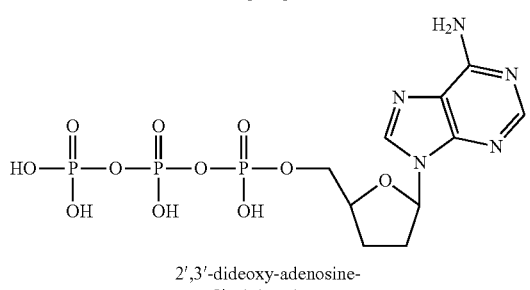

2',3'-dideoxy-adenosine-
5'-triphosphate

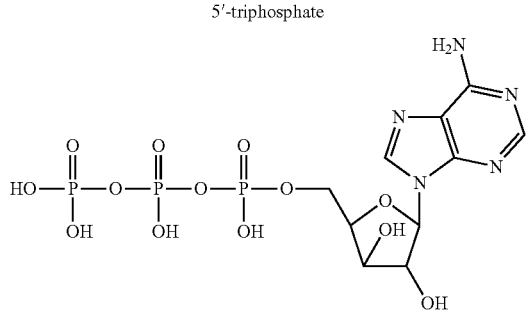

2'-ara-adenosine-
5'-triphosphate

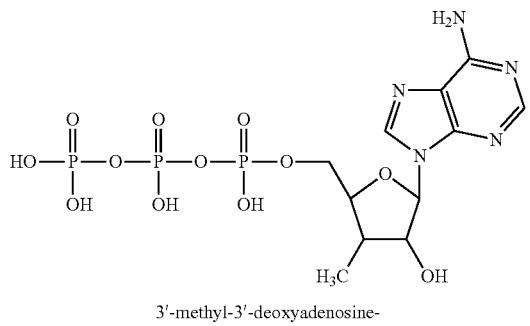

3'-methyl-3'-deoxyadenosine-
5'-triphosphate

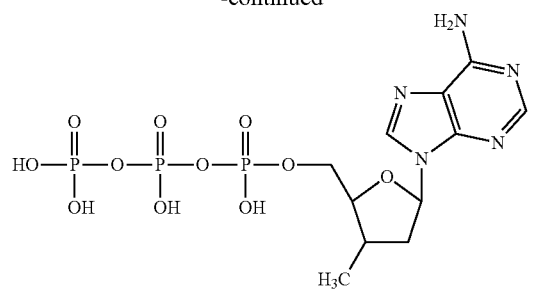

3'-methyl-2',3'-dideoxyadenosine-
5'-triphosphate

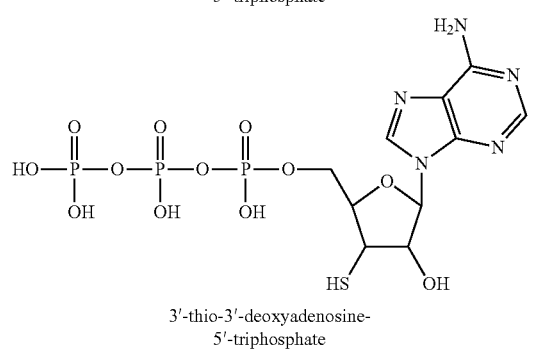

3'-thio-3'-deoxyadenosine-
5'-triphosphate

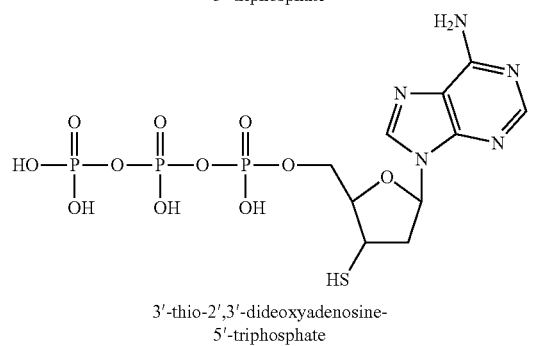

3'-thio-2',3'-dideoxyadenosine-
5'-triphosphate

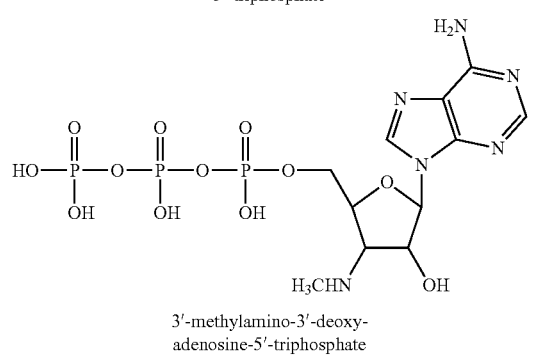

3'-methylamino-3'-deoxy-
adenosine-5'-triphosphate

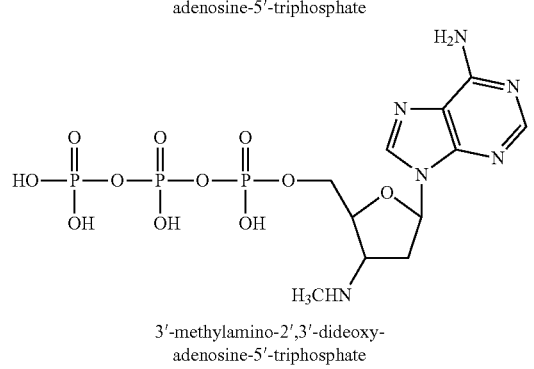

3'-methylamino-2',3'-dideoxy-
adenosine-5'-triphosphate

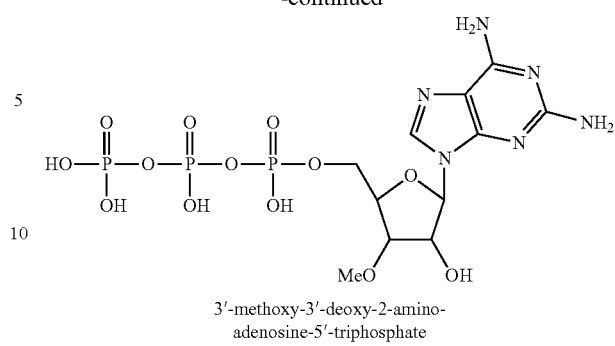

3'-methoxy-3'-deoxy-2-amino-
adenosine-5'-triphosphate

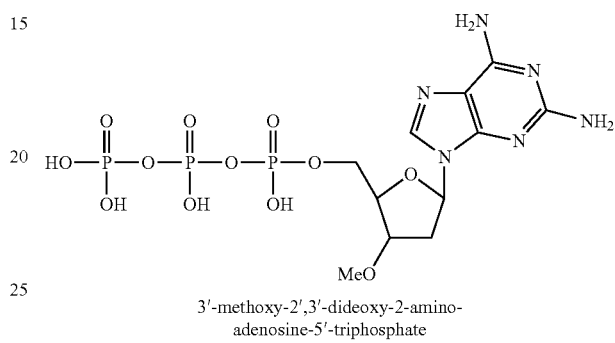

3'-methoxy-2',3'-dideoxy-2-amino-
adenosine-5'-triphosphate

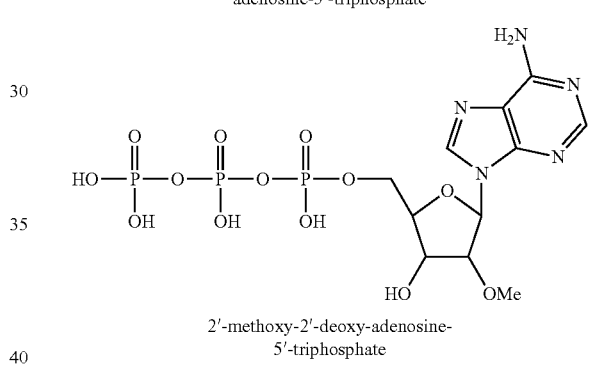

2'-methoxy-2'-deoxy-adenosine-
5'-triphosphate

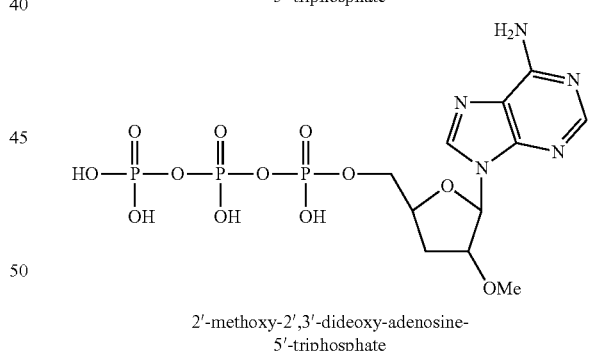

2'-methoxy-2',3'-dideoxy-adenosine-
5'-triphosphate

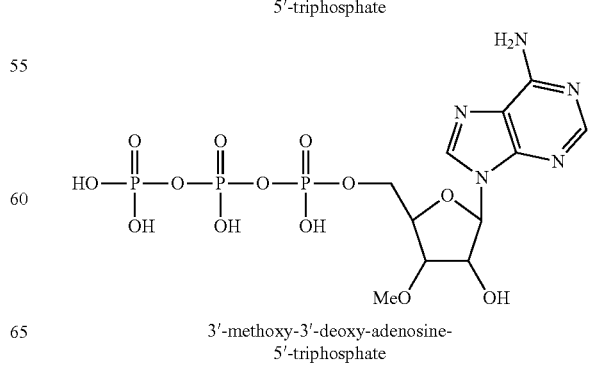

3'-methoxy-3'-deoxy-adenosine-
5'-triphosphate

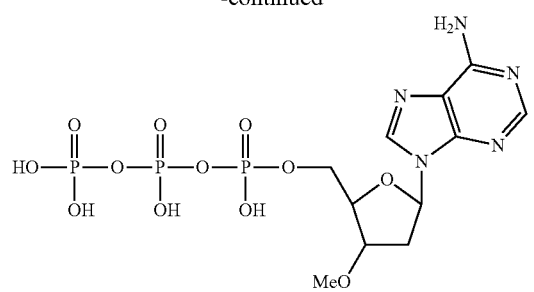

3'-methoxy-2',3'-dideoxy-adenosine-
5'-triphosphate

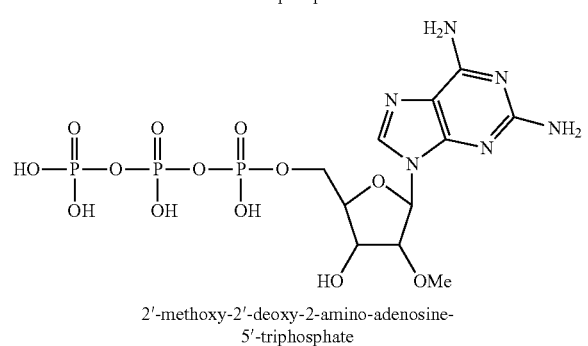

2'-methoxy-2'-deoxy-2-amino-adenosine-
5'-triphosphate

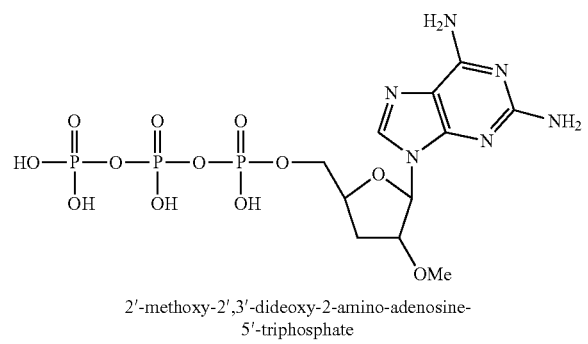

2'-methoxy-2',3'-dideoxy-2-amino-adenosine-
5'-triphosphate

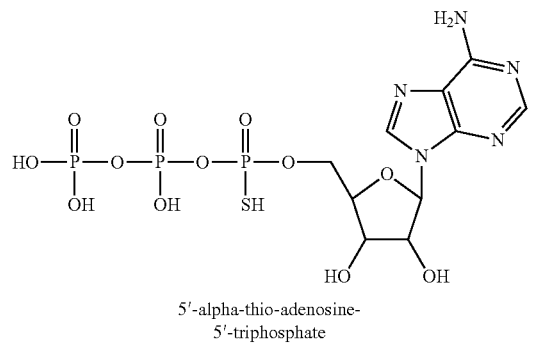

5'-alpha-thio-adenosine-
5'-triphosphate

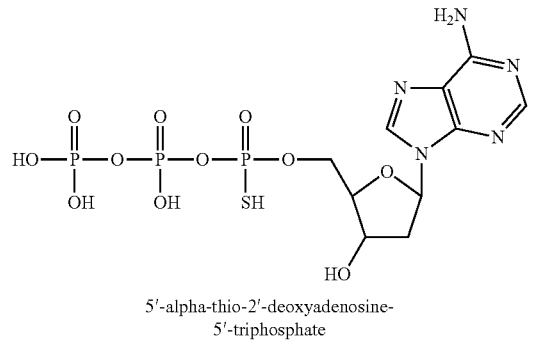

5'-alpha-thio-2'-deoxyadenosine-
5'-triphosphate

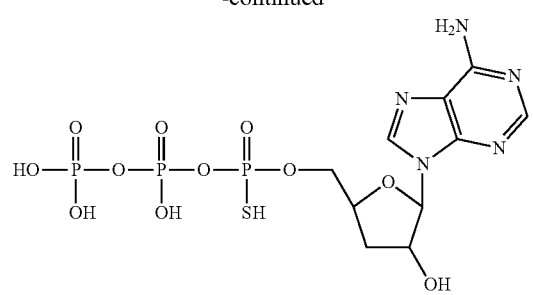

5'-alpha-thio-3'-deoxyadenosine-
5'-triphosphate

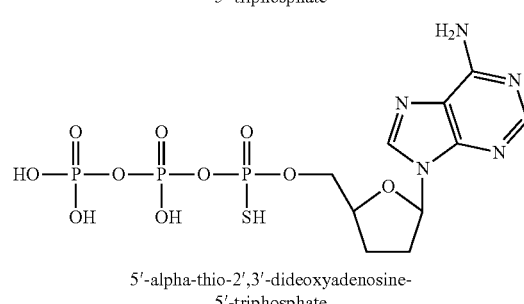

5'-alpha-thio-2',3'-dideoxyadenosine-
5'-triphosphate

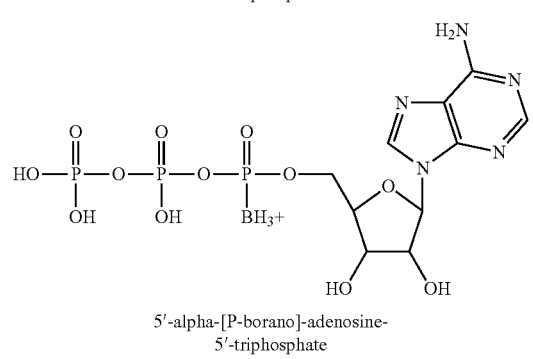

5'-alpha-[P-borano]-adenosine-
5'-triphosphate

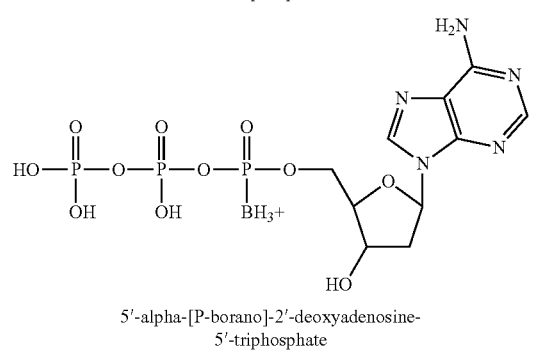

5'-alpha-[P-borano]-2'-deoxyadenosine-
5'-triphosphate

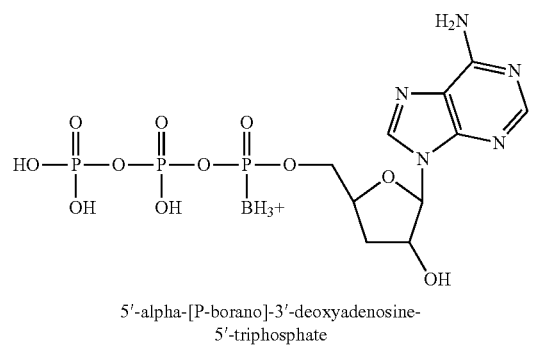

5'-alpha-[P-borano]-3'-deoxyadenosine-
5'-triphosphate

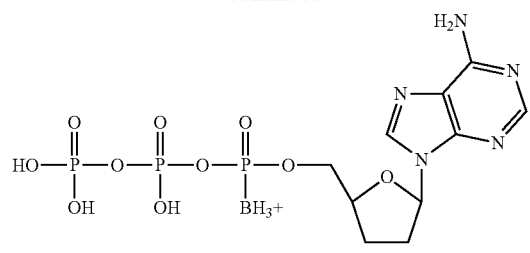

5′-alpha-[P-borano]-2′,3′-dideoxyadenosine-5′-triphosphate

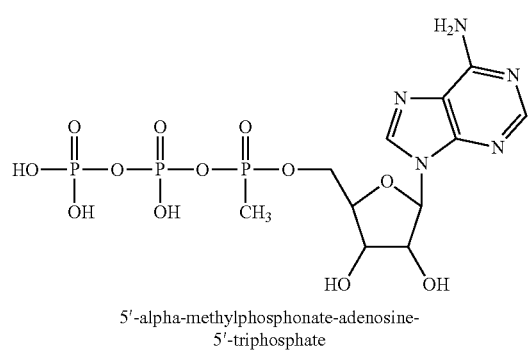

5′-alpha-methylphosphonate-adenosine-5′-triphosphate

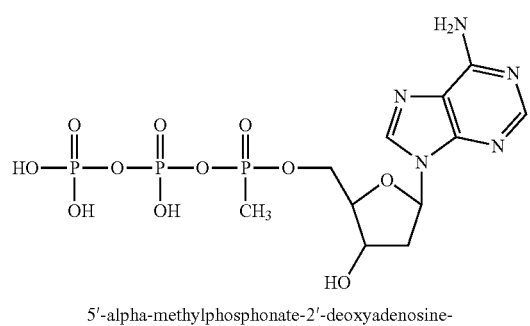

5′-alpha-methylphosphonate-2′-deoxyadenosine-5′-triphosphate

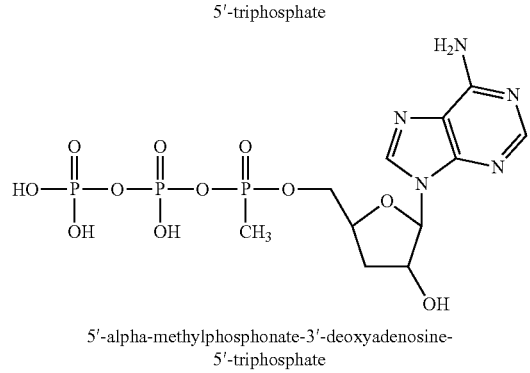

5′-alpha-methylphosphonate-3′-deoxyadenosine-5′-triphosphate

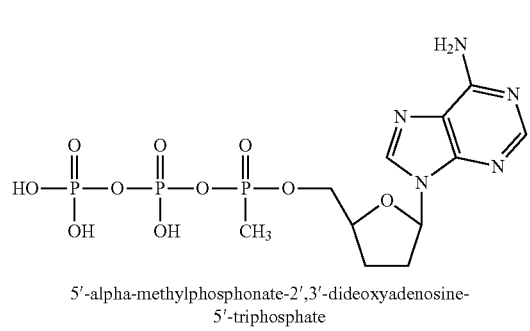

5′-alpha-methylphosphonate-2′,3′-dideoxyadenosine-5′-triphosphate

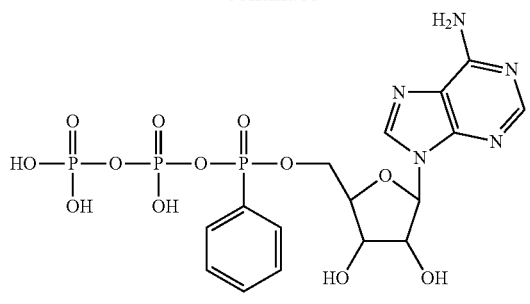

5′-alpha-phenylphosphonate-adenosine-5′-triphosphate

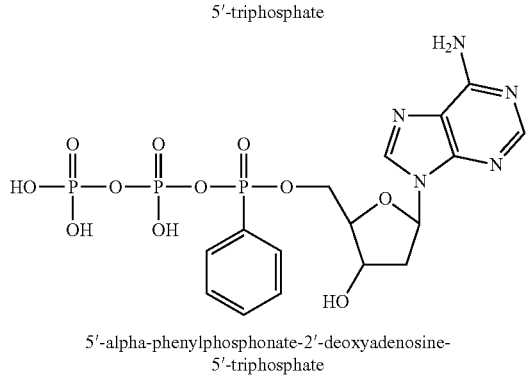

5′-alpha-phenylphosphonate-2′-deoxyadenosine-5′-triphosphate

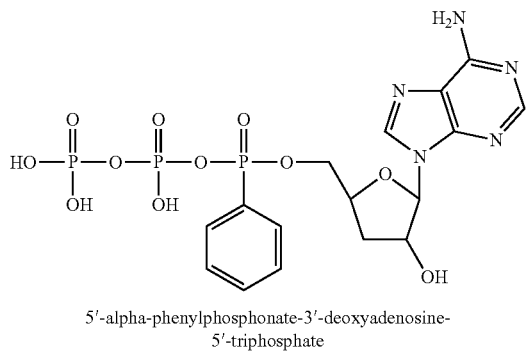

5′-alpha-phenylphosphonate-3′-deoxyadenosine-5′-triphosphate

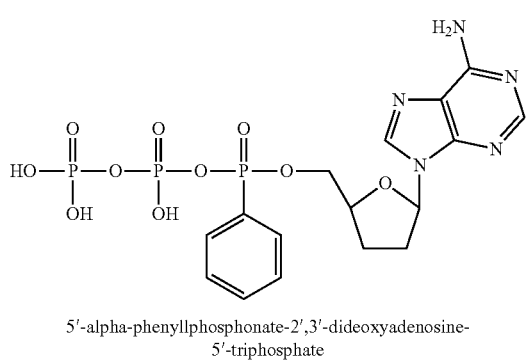

5′-alpha-phenyllphosphonate-2′,3′-dideoxyadenosine-5′-triphosphate

Certain aspects and embodiments of the compositions and methods provided herein include at least one modified ligase cofactor. In preferred embodiments, the modified ligase cofactor is a modified NAD+ having one or more substitution groups.

In embodiments of the aspects herein, modified NAD+s and derivatives thereof in accordance with the invention provide compounds of Formula IB:

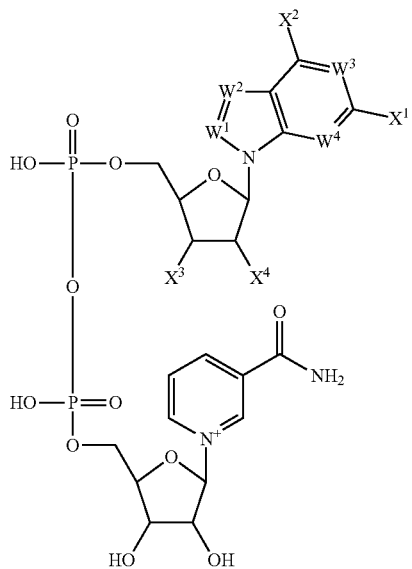

wherein:
$W^1$, $W^2$, $W^3$, and $W^4$ are each independently selected from the group consisting of N, $CR^1$, and $N^+R^1$;

each $R^1$ is independently selected from the group consisting of H, F, Cl, Br, I, $OR^2$, $SR^2$, $SeR^2$, $NR^2R^3$, C(Y)R, and substituted or non-substituted alkyl, alkenyl, alkynyl, aryl, and aralkyl,
 wherein any substituent may each optionally contain one or more heteroatoms;

each $R^2$ and each $R^3$ is independently selected from the group consisting of H or substituted or non-substituted alkyl, alkenyl, alkynyl, aryl, and aralkyl,
 wherein any substituent may each optionally contain one or more heteroatoms;

each $R^4$ is selected from the group consisting of H, F, Cl, Br, $OR^2$, $SR^2$, $SeR^2$, $NR^2R^3$, $C(Y)R^2$, and substituted or non-substituted alkyl, alkenyl, alkynyl, aryl, and aralkyl,
 wherein any substituent may each optionally contain one or more heteroatoms;

each Y is selected from the group consisting of O, S, Se, $C(R^1)_2$, and $NR^1$; and $X^1$, $X^2$, $X^3$, and $X^4$ are each independently selected from the group consisting of $R^1$, $NR^2OR^2$, $NR^2$—$NR^2R^3$, CN, $N_3$, NO, $NO_2$, NCO, NCS, OCN, SCN, and $SSR^2$.

Preferred embodiments of modified NAD+ have the structure:

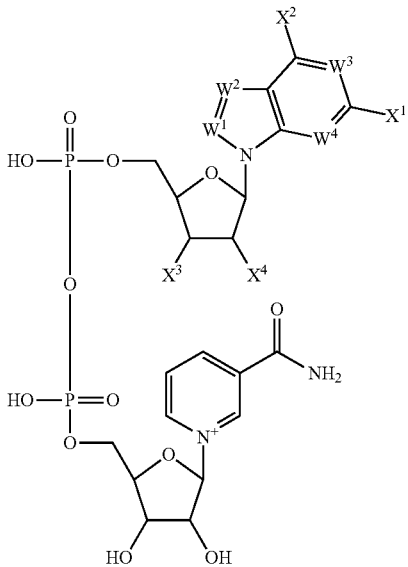

wherein:
$W^1$, $W^2$, $W^3$, and $W^4$, are each independently selected from the group consisting of N, $N^+$—$CH_3$, $N^+$—$CH_2CH_3$, $N^+$—$CH_2CH_2CH_3$, $N^+$—$CH_2CH_2CH_2CH_3$, $N^+$—$CH(CH_3)_2$, CH, C—$CH_3$, C—$CH_2CH_3$, C—$CH_2CH_2CH_3$, C—$CH_2CH_2CH_2CH_3$, C—$CH(CH_3)_2$, C—$NH_2$, C—$NHCH_3$, C—$N(CH_3)_2$, C—$N_3$, and C—OH;

$X^1$ is selected from the group consisting of H, $NH_2$, OH, $NHCH_3$, and $N(CH_3)_2$;

$X^2$ is selected from the group consisting of H, Cl, OH, $NH_2$, $NH(CH_3)$, and $N(CH_3)_2$;

$X^3$ is selected from the group consisting of H, F, $CH_3$, OH, SH, $OCH_3$, $NH_2$, $NHCH_3$, $N(CH_3)_2$, and $N_3$; and $X^4$ is selected from the group consisting of H, F, OH, $OCH_3$, $NH_2$, $NHCH_3$, $N(CH_3)_2$, and $N_3$.

Preferred embodiments of modified NAD+ have the structure:

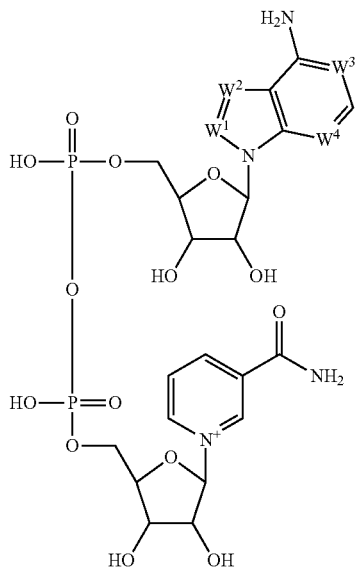

wherein:
W$^1$, W$^2$, W$^3$, and W$^4$ are each independently selected from the group consisting of N, CR$^1$, and N$^+$R$^1$; and
each R$^1$ is independently selected from the group consisting of H, F, Cl, Br, I, OR$^2$, SR$^2$, SeR$^2$, NR$^2$R$^3$, N$_3$, C(Y)R$^4$, and substituted or non-substituted alkyl, alkenyl, alkynyl, aryl, and aralkyl,
wherein any substituent may each optionally contain one or more heteroatoms;
each R$^2$ and each R$^3$ is independently selected from the group consisting of H or substituted or non-substituted alkyl, alkenyl, alkynyl, aryl, and aralkyl,
wherein any substituent may each optionally contain one or more heteroatoms;
each R$^4$ is selected from the group consisting of H, F, Cl, Br, OR$^2$, SR$^2$, SeR$^2$, NR$^2$R$^3$, C(Y)R$^2$, and substituted or non-substituted alkyl, alkenyl, alkynyl, aryl, and aralkyl,
wherein any substituent may each optionally contain one or more heteroatoms; and
each Y is selected from the group consisting of O, S, Se, CR$^1$R$^1$, and NR$^1$.

Preferred embodiments of modified NAD+ have the structure:

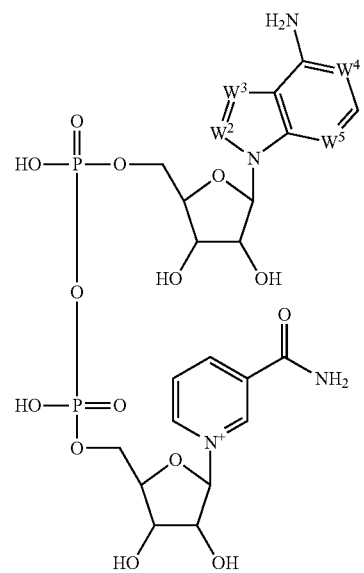

wherein:
W$^2$, W$^3$, W$^4$, and W$^5$ are each independently selected from the group consisting of N, N$^+$—CH$_3$, N$^+$—CH$_2$CH$_3$, N$^+$—CH$_2$CH$_2$CH$_3$, N$^+$—CH$_2$CH$_2$CH$_2$CH$_3$, N$^+$—CH(CH$_3$)$_2$, CH, C—CH$_3$, C—CH$_2$CH$_3$, C—CH$_2$CH$_2$CH$_3$, C—CH$_2$CH$_2$CH$_2$CH$_3$, C—CH(CH$_3$)$_2$, C—NH$_2$, C—NHCH$_3$, C—N(CH$_3$)$_2$, C—N$_3$, and C—OH.

Preferred embodiments of modified NAD+ have the structure:

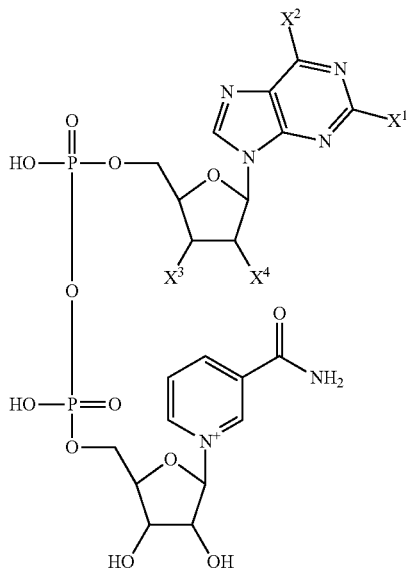

wherein:
X$^1$, X$^2$, X$^3$, and X$^4$ are each independently selected from the group consisting of R$^1$, NR$^2$OR$^2$, NR$^2$—NR$^2$R$^3$, CN, N$_3$, NO, NO$_2$, NCO, NCS, OCN, SCN, and SSR$^2$;
each R$^1$ is independently selected from the group consisting of H, F, Cl, Br, I, OR$^2$, SR$^2$, SeR$^2$, NR$^2$R$^3$, C(Y)R$^4$, and substituted or non-substituted alkyl, alkenyl, alkynyl, aryl, and aralkyl,
wherein any substituent may each optionally contain one or more heteroatoms;
each R$^2$ and each R$^3$ is independently selected from the group consisting of H or substituted or non-substituted alkyl, alkenyl, alkynyl, aryl, and aralkyl,
wherein any substituent may each optionally contain one or more heteroatoms;
each R$^4$ is selected from the group consisting of H, F, Cl, Br, OR$^2$, SR$^2$, SeR$^2$, NR$^2$R$^3$, C(Y)R$^2$ and substituted or non-substituted alkyl, alkenyl, alkynyl, aryl, and aralkyl,
wherein any substituent may each optionally contain one or more heteroatoms; and
each Y is selected from the group consisting of O, S, Se, CR$^1$R$^1$, and NR$^1$.

Preferred embodiments of modified NAD+ have the structure:

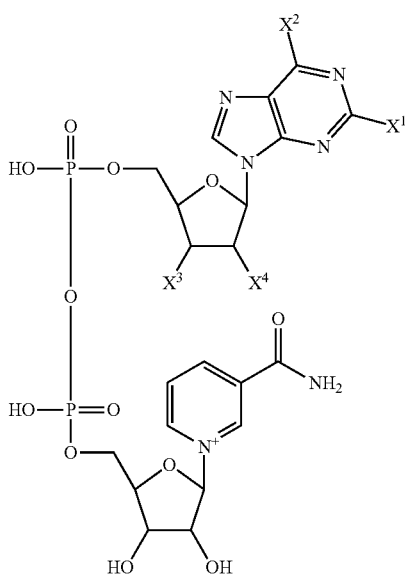

wherein:
X¹ is selected from the group consisting of H, NH₂, OH, NHCH₃, and N(CH₃)₂;
X² is selected from the group consisting of H, Cl, OH, NH₂, NH(CH₃), and N(CH₃)₂;
X³ is selected from the group consisting of H, F, CH₃, OH, SH, OCH₃, NH₂, NHCH₃, N(CH₃)₂, and N₃; and
X⁴ is selected from the group consisting of H, F, OH, OCH₃, NH₂, NHCH₃, N(CH₃)₂, and N₃.

Preferred embodiments of modified NAD+ have the structure:

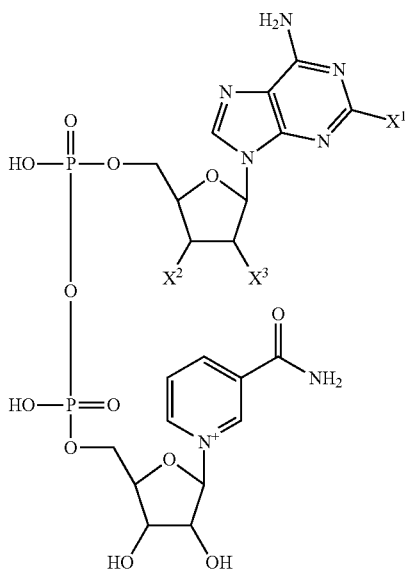

wherein:
X¹, X², and X³ are each independently selected from the group consisting of R¹, NR²OR², NR²—NR²R³, CN, N₃, NO, NO₂, NCO, NCS, OCN, SCN, and SSR²;
each R¹ is independently selected from the group consisting of H, F, Cl, Br, I, OR², SR², SeR², NR²R³, C(Y)R⁴, and substituted or non-substituted alkyl, alkenyl, alkynyl, aryl, and aralkyl,
  wherein any substituent may each optionally contain one or more heteroatoms;
each R² and each R³ is independently selected from the group consisting of H or substituted or non-substituted alkyl, alkenyl, alkynyl, aryl, and aralkyl,
  wherein any substituent may each optionally contain one or more heteroatoms;
each R⁴ is selected from the group consisting of H, F, Cl, Br, OR², SR², SeR², NR²R³, C(Y)R², and substituted or non-substituted alkyl, alkenyl, alkynyl, aryl, and aralkyl,
  wherein any substituent may each optionally contain one or more heteroatoms;
each Y is selected from the group consisting of O, S, Se, CR¹R¹, and NR¹.

Preferred embodiments of modified NAD+ have the structure:

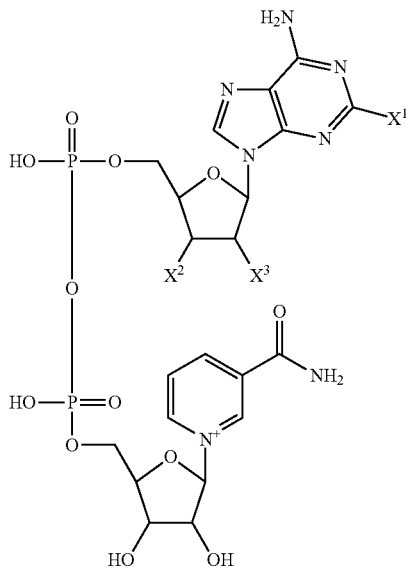

wherein:
X¹ is selected from the group consisting of H, NH₂, OH, NHCH₃, and N(CH₃)₂;
X² is selected from the group consisting of H, F, CH₃, OH, SH, OCH₃, NH₂, NHCH₃, N(CH₃)₂, and N₃; and
X³ is selected from the group consisting of H, F, OH, OCH₃, NH₂, NHCH₃, N(CH₃)₂, and N₃.

Preferred embodiments of modified NAD+ have the structure:

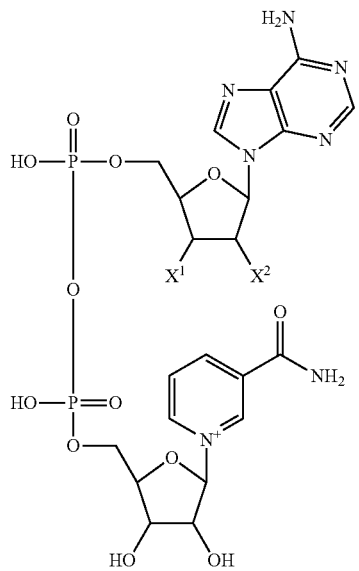

wherein:
X¹ and X² are each independently selected from the group consisting of R¹, NR²OR², NR²—NR²R³, CN, N₃, NO, NO₂, NCO, NCS, OCN, SCN, and SSR²;

each R¹ is independently selected from the group consisting of H, F, Cl, Br, I, OR², SR², SeR², NR²R³, C(Y)R⁴, and substituted or non-substituted alkyl, alkenyl, alkynyl, aryl, and aralkyl,
  wherein any substituent may each optionally contain one or more heteroatoms;
each R² and each R³ is independently selected from the group consisting of H or substituted or non-substituted alkyl, alkenyl, alkynyl, aryl, and aralkyl,
  wherein any substituent may each optionally contain one or more heteroatoms;
each R⁴ is selected from the group consisting of H, F, Cl, Br, OR², SR², SeR², NR²R³, C(Y)R², and substituted or non-substituted alkyl, alkenyl, alkynyl, aryl, and aralkyl,
  wherein any substituent may each optionally contain one or more heteroatoms; and
each Y is selected from the group consisting of O, S, Se, CR¹R¹, and NR¹.

Preferred embodiments of modified NAD+ have the structure:

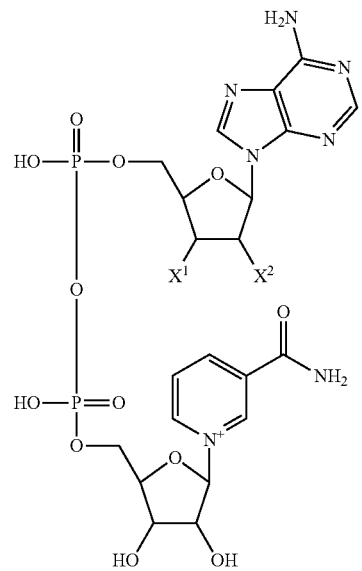

wherein:
X¹ is selected from the group consisting of H, F, CH₃, OH, SH, OCH₃, NH₂, NHCH₃, N(CH₃)₂, and N₃; and
X² is selected from the group consisting of H, F, OH, OCH₃, NH₂, NHCH₃, N(CH₃)₂, and N₃.

Preferred embodiments of modified NAD+ have the structure:

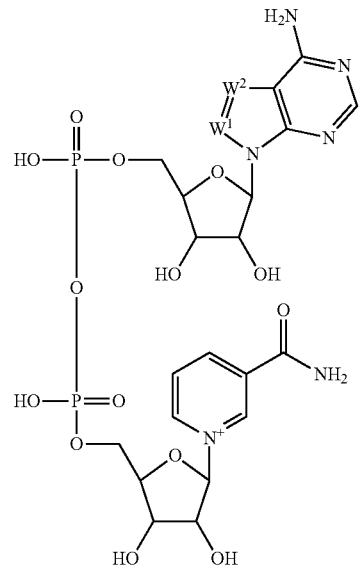

wherein:
W¹ and W² are each independently selected from the group consisting of N, CR¹, and N⁺R¹; and
each R¹ is independently selected from the group consisting of H, F, Cl, Br, I, OR², SR², SeR², NR²R³, N₃, C(Y)R⁴, and substituted or non-substituted alkyl, alkenyl, alkynyl, aryl, and aralkyl,
  wherein any substituent may each optionally contain one or more heteroatoms;
each R² and each R³ is independently selected from the group consisting of H or substituted or non-substituted alkyl, alkenyl, alkynyl, aryl, and aralkyl,
  wherein any substituent may each optionally contain one or more heteroatoms;

each R⁴ is selected from the group consisting of H, F, Cl, Br, OR², SR², SeR², NR²R³, C(Y)R², and substituted or non-substituted alkyl, alkenyl, alkynyl, aryl, and aralkyl, wherein any substituent may each optionally contain one or more heteroatoms; and each Y is selected from the group consisting of O, S, Se, CR¹R¹, and NR¹.

Preferred embodiments of modified NAD+ have the structure:

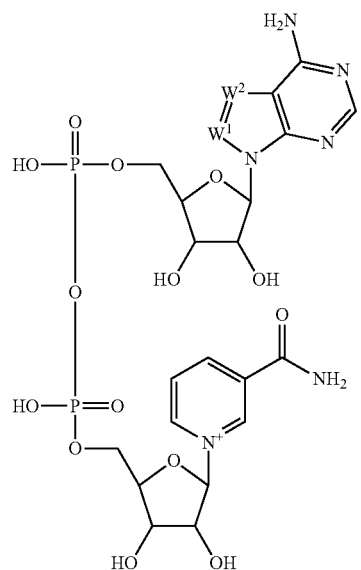

wherein:
W¹ and W² are each independently selected from the group consisting of N, N⁺—CH₃, N⁺—CH₂CH₃, N⁺—CH₂CH₂CH₃, N⁺—CH₂CH₂CH₂CH₃, N⁺—CH(CH₃)₂, CH, C—N₃, C—CH₃, C—CH₂CH₃, C—CH₂CH₂CH₃, C—CH₂CH₂CH₂CH₃, C—CH(CH₃)₂, C—NH₂, C—NHCH₃, C—N(CH₃)₂, and C—OH.

Preferred embodiments of modified NAD+ have the structure:

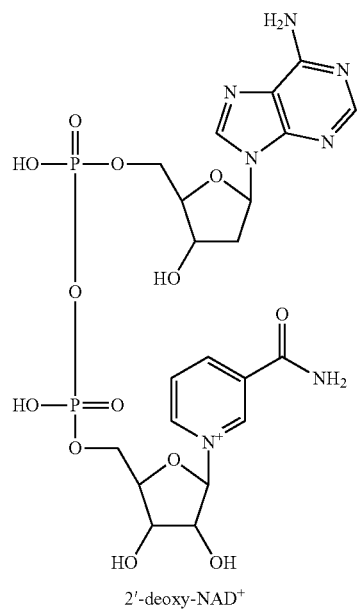

2'-deoxy-NAD⁺

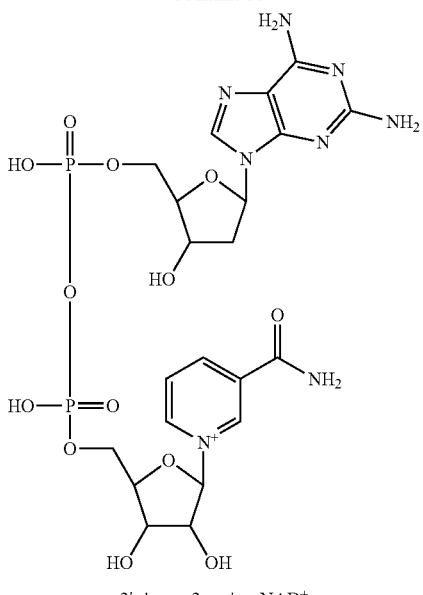

2'-deoxy-2-amino-NAD⁺

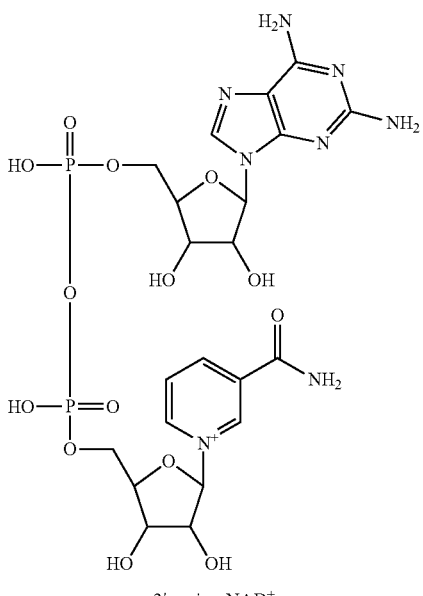

2'-amino-NAD⁺

-continued

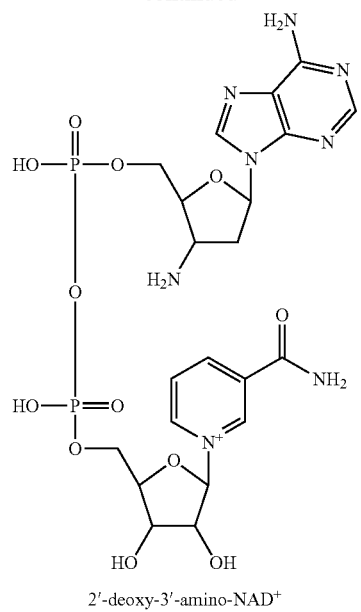

2'-deoxy-3'-amino-NAD⁺

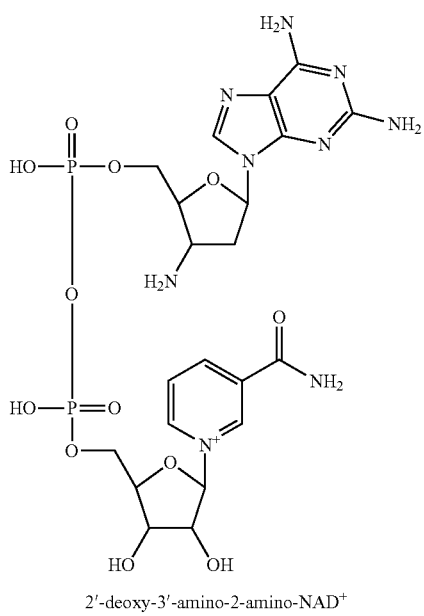

2'-deoxy-3'-amino-2-amino-NAD⁺

-continued

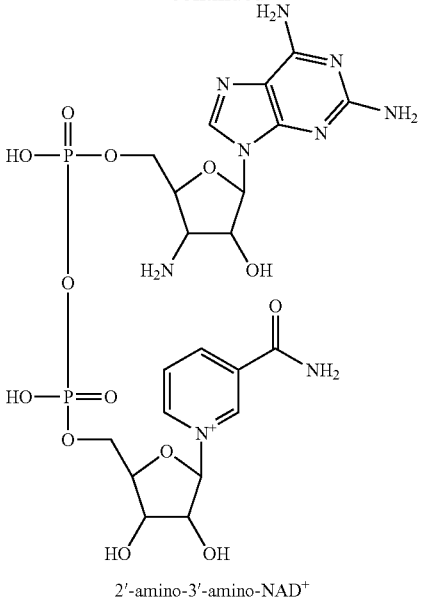

2'-amino-3'-amino-NAD⁺

Modified Acceptors

Certain aspects and embodiments of the compositions and methods provided herein include at least one modified acceptor. In preferred embodiments, the modified acceptor has one or more substitution groups. In some embodiments, modified acceptors suitable for use with the methods and compositions described herein include those as described in the art, for example, PNA-DNA chimeric probes in Egholm, M., et al., U.S. Pat. No. 6,297,016) and 3'-NH₂ substituted probes (Fung, S., et al., U.S. Pat. No. 5,593,826), In embodiments of the aspects herein, modified acceptors and derivatives thereof in accordance with the invention provide compounds of Formula II:

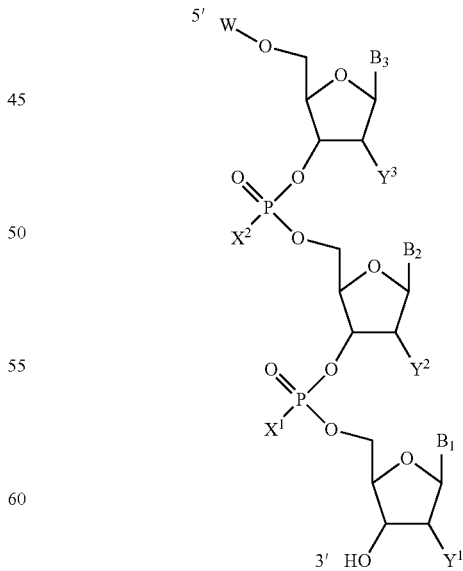

wherein:
B¹, B², and B³ are each independently selected from the group consisting of a substituted or non-substituted purine or pyrimidine, any aza or deaza derivative thereof, and any "universal base" or "degenerate base", which is preferably recognizable by a nucleic acid polymerase or ligase;

$X^1$ and $X^2$ are each independently selected from the group consisting of OH, SH, $CH_3$, and $OCH_2CH_3$;

$Y^1$, $Y^2$, and $Y^3$ are each independently selected from the group consisting of H, F, OH, and $OCH_3$; and W is selected from H or an oligonucleotidyl residue.

Preferred embodiments of modified acceptors have the structure:

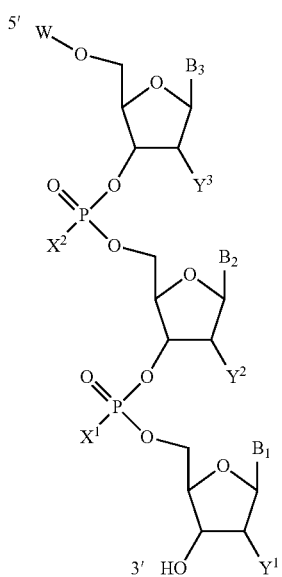

wherein:

$B^1$, $B^2$, and $B^3$ are each independently selected from the group consisting of a substituted or non-substituted purine or pyrimidine, any aza or deaza derivative thereof, and any "universal base" or "degenerate base", which is preferably recognizable by a nucleic acid polymerase or ligase;

$X^1$ is independently selected from the group consisting of OH, SH, $OCH_2CH_3$, and $CH_3$;

$X^2$ is independently selected from the group consisting of OH, SH, $OCH_2CH_3$, and $CH_3$;

$Y^1$, $Y^2$ and $Y^3$ are each independently selected from the group consisting of H and $OCH_3$;

W is selected from H or an oligonucleotidyl residue.

Modified Donors

Certain aspects and embodiments of the compositions and methods provided herein include at least one modified donor. In preferred embodiments, the modified donor has one or more substitution groups. In some embodiments, modified acceptors suitable for use with the methods and compositions described herein include those as described in the art, for example, use of 5'-thiophosphates in the donor (5'-phosphate) strand (Bandaru, R., et al., U.S. Pat. Nos. 6,811,986 and 6,635,425).

In embodiments of the aspects herein, modified donors and derivatives thereof in accordance with the invention provide compounds of Formula III:

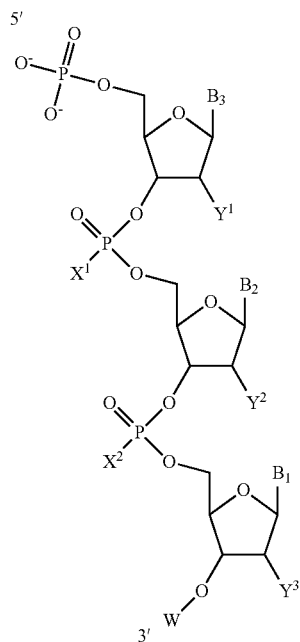

wherein:

$B^1$, $B^2$, and $B^3$ are each independently selected from the group consisting of a substituted or non-substituted purine or pyrimidine, any aza or deaza derivative thereof, and any "universal base" or "degenerate base", which is preferably recognizable by a nucleic acid polymerase or ligase;

$X^1$ and $X^2$ are each independently selected from the group consisting of OH, SH, $CH_3$, and $OCH_2CH_3$;

$Y^1$, $Y^2$, and $Y^3$ are each independently selected from the group consisting of H, F, OH, and $OCH_3$; and W is selected from H or an oligonucleotidyl residue.

Preferred embodiments of modified donors have the structure:

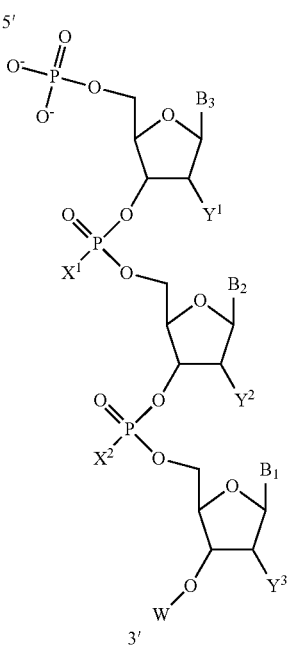

wherein:
B$^1$, B$^2$, and B$^3$ are each independently selected from the group consisting of a substituted or non-substituted purine or pyrimidine, any aza or deaza derivative thereof, and any "universal base" or "degenerate base", which is preferably recognizable by a nucleic acid polymerase or ligase;
X$^1$ and X$^2$ are each independently selected from the group consisting of OH, SH, OCH$_2$CH$_3$, or CH$_3$;
Y$^1$, Y$^2$, and Y$^3$ are each independently selected from the group consisting of H and OCH$_3$;
W is selected from H or an oligonucleotidyl residue.

In embodiments of the aspects herein, modified donors and derivatives thereof in accordance with the invention provide compounds of Formula IV:

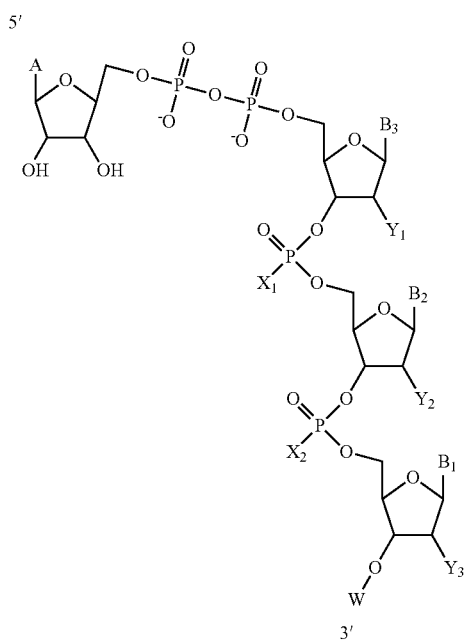

wherein:
A is adenine;
B$^1$, B$^2$, and B$^3$ are each independently selected from the group consisting of a substituted or non-substituted purine or pyrimidine, any aza or deaza derivative thereof, and any "universal base" or "degenerate base", which is preferably recognizable by a nucleic acid polymerase or ligase;
X$^1$ and X$^2$ are each independently selected from the group consisting of OH, SH, CH$_3$, and OCH$_2$CH$_3$;
Y$^1$, Y$^2$, and Y$^3$ are each independently selected from the group consisting of H, F, OH, and OCH$_3$; and
W is selected from H or an oligonucleotidyl residue.

Combinations of Modified Ligase Cofactors, Modified Acceptors and Modified Donors Certain aspects and embodiments of the compositions and methods provided herein include the use of combinations of modified ligase cofactors, modified acceptors and modified donors. Any possible combination of two or more may be used. In some embodiments, more than one type of ligase cofactor, modified acceptor or modified donor may be used.

Exemplary combinations include combinations of two or more of modified ligase cofactors, modified acceptors and modified donors selected from the groups as follows:

Modified Acceptors:

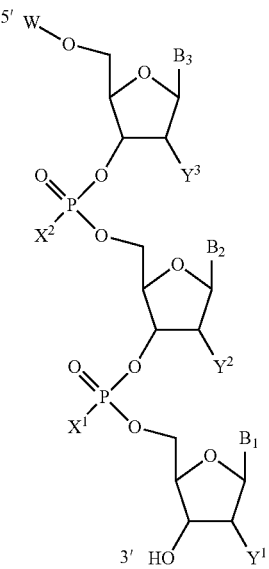

wherein:
B$^1$, B$^2$, and B$^3$ are each independently selected from the group consisting of a substituted or non-substituted purine or pyrimidine, any aza or deaza derivative thereof, and any "universal base" or "degenerate base", which is preferably recognizable by a nucleic acid polymerase or ligase;
X$^1$ and X$^2$ are each independently selected from the group consisting of OH, SH, CH$_3$, and OCH$_2$CH$_3$;
Y$^1$, Y$^2$, and Y$^3$ are each independently selected from the group consisting of H, F, OH, and OCH$_3$; and
W is selected from H or an oligonucleotidyl residue.

Modified Donors:

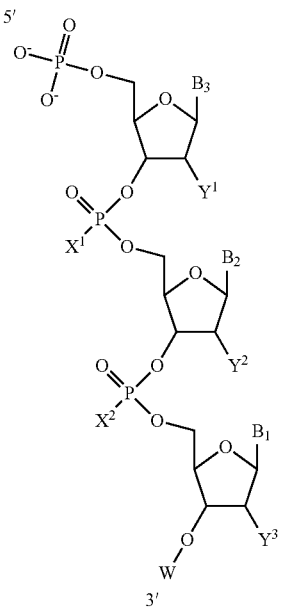

wherein:
- B¹, B², and B³ are each independently selected from the group consisting of a substituted or non-substituted purine or pyrimidine, any aza or deaza derivative thereof, and any "universal base" or "degenerate base", which is preferably recognizable by a nucleic acid polymerase or ligase;
- X¹ and X² are each independently selected from the group consisting of OH, SH, CH$_3$, and OCH$_2$CH$_3$;
- Y¹, Y², and Y³ are each independently selected from the group consisting of H, F, OH, and OCH$_3$; and
- W is selected from H or an oligonucleotidyl residue.

Modified Cofactors:

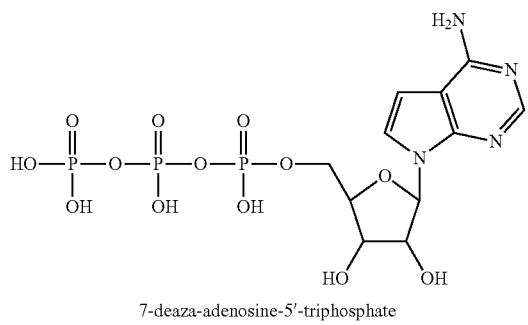

7-deaza-adenosine-5'-triphosphate

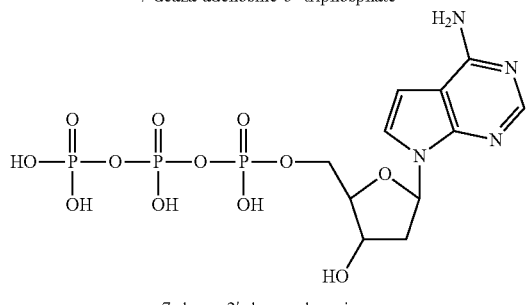

7-deaza-2'-deoxyadenosine-5'-triphosphate

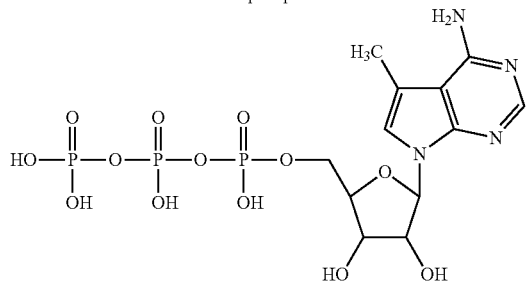

7-methyl-7-deaza-adenosine-5'-triphosphate

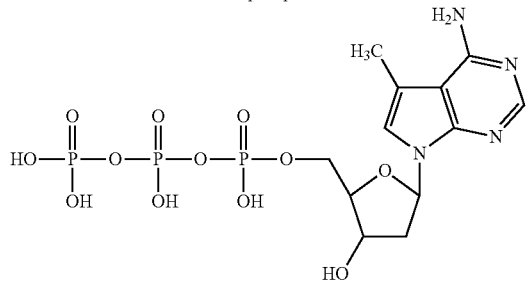

7-methyl-7-deaza-2'-deoxyadenosine-5'-triphosphate

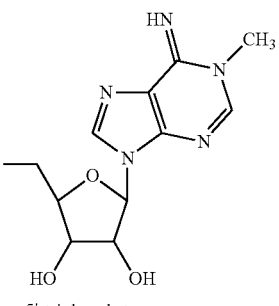

N1-methyl-adenosine-5'-triphosphate

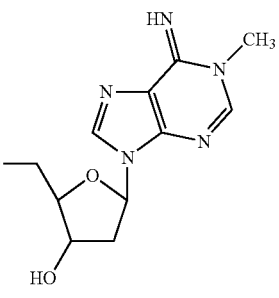

N1-methyl-2'-deoxyadenosine-5'-triphosphate

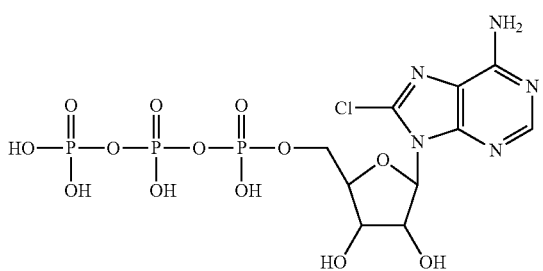

8-chloro-adenosine-5'-triphosphate

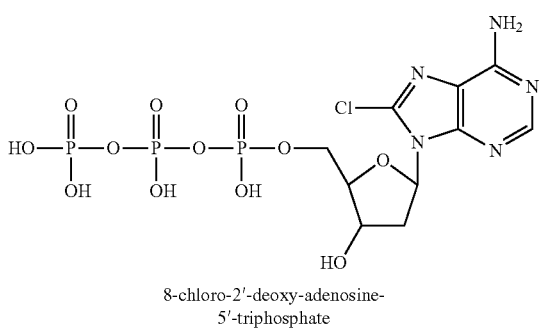

8-chloro-2'-deoxy-adenosine-5'-triphosphate

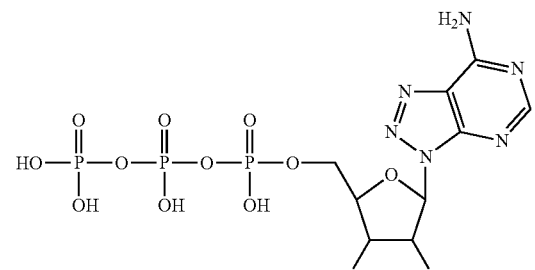

8-aza-adenosine-5'-triphosphate

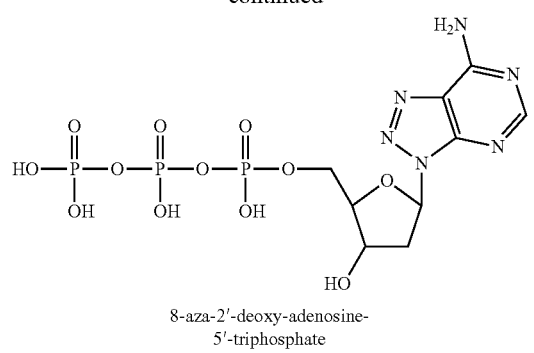

8-aza-2'-deoxy-adenosine-
5'-triphosphate

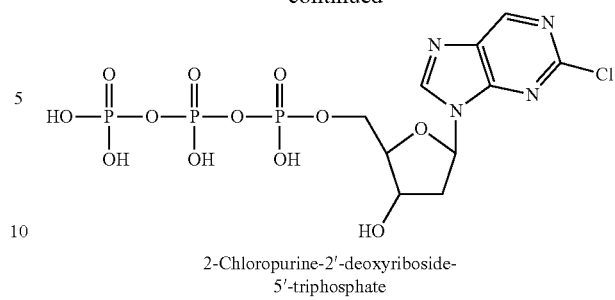

2-Chloropurine-2'-deoxyriboside-
5'-triphosphate 8-azido-adenosine-5'-triphosphate

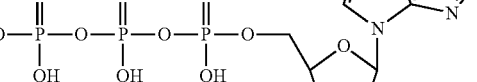

2-aminopurine-2'-deoxyriboside-
5'-triphosphate 8-azido-2'-deoxy-adenosine-
5'-triphosphate

inosine-5'-triphosphate

N6-methyl-adenosine-5'-triphosphate

2'-deoxy-inosine-5'-triphosphate

N6-methyl-2'-deoxy-adenosine-
5'-triphosphate

2-amino-adenosine-5'-triphosphate

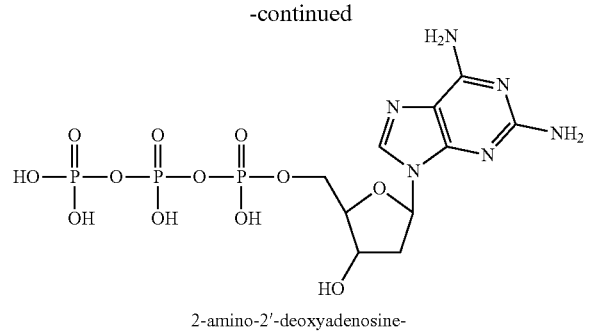

2-amino-2'-deoxyadenosine-
5'-triphosphate

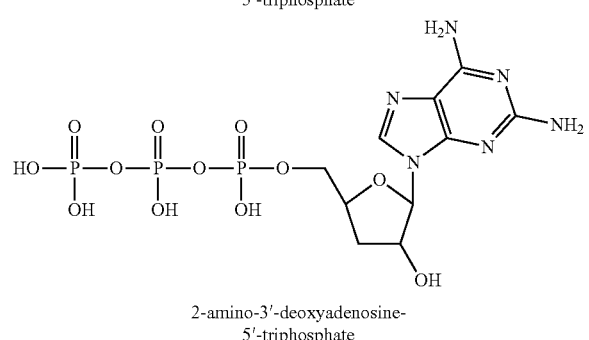

2-amino-3'-deoxyadenosine-
5'-triphosphate

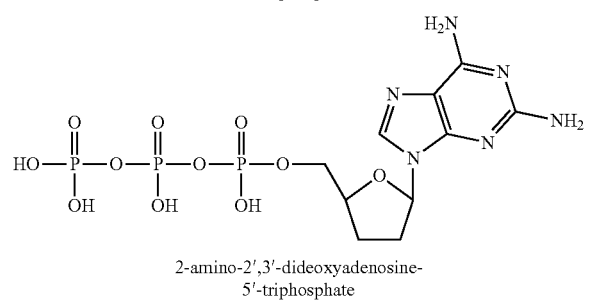

2-amino-2',3'-dideoxyadenosine-
5'-triphosphate

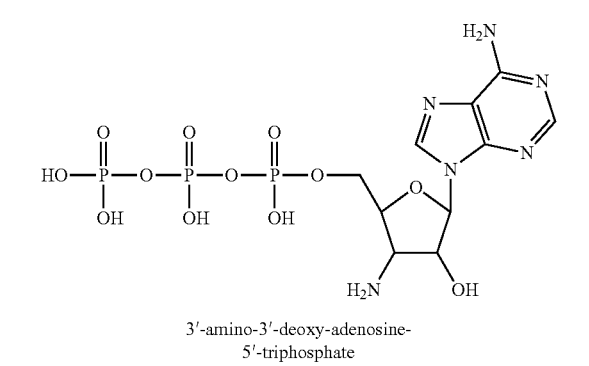

3'-amino-3'-deoxy-adenosine-
5'-triphosphate

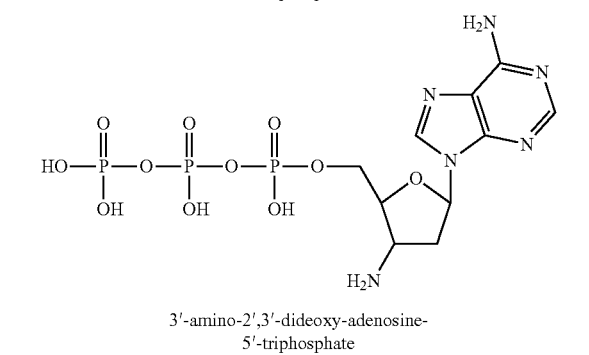

3'-amino-2',3'-dideoxy-adenosine-
5'-triphosphate

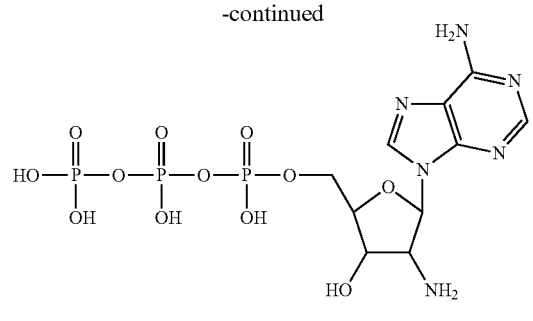

2'-amino-2'-deoxy-adenosine-
5'-triphosphate

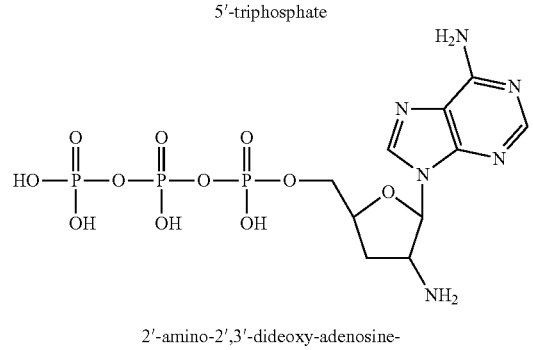

2'-amino-2',3'-dideoxy-adenosine-
5'-triphosphate

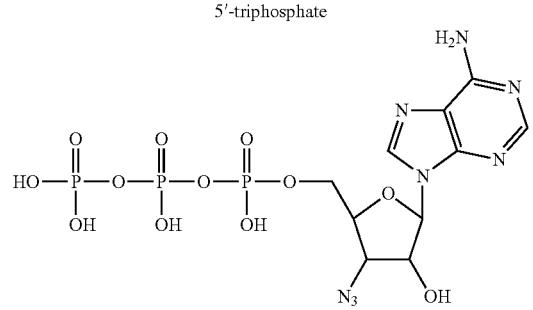

3'-azido-3'-deoxy-adenosine-
5'-triphosphate

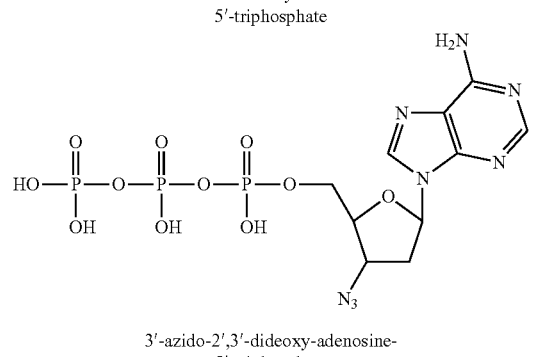

3'-azido-2',3'-dideoxy-adenosine-
5'-triphosphate

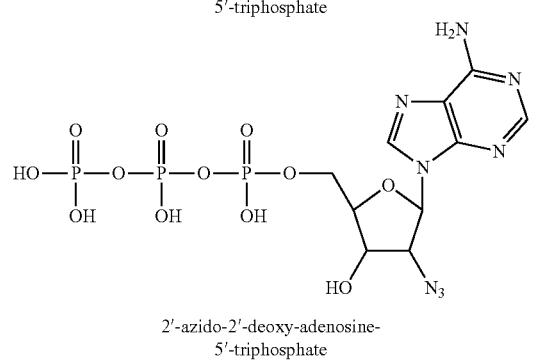

2'-azido-2'-deoxy-adenosine-
5'-triphosphate

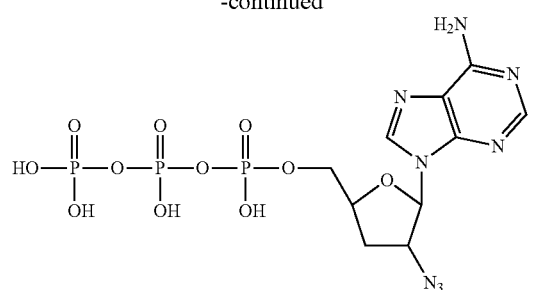

2'-azido-2',3'-dideoxy-adenosine-
5'-triphosphate

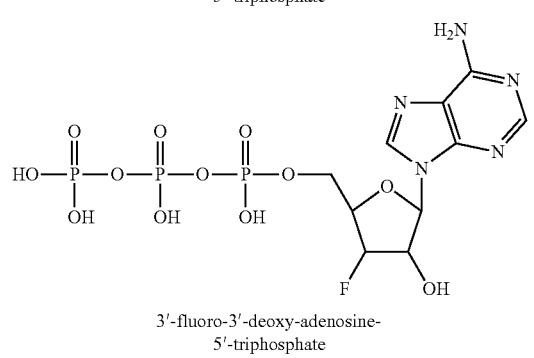

3'-fluoro-3'-deoxy-adenosine-
5'-triphosphate

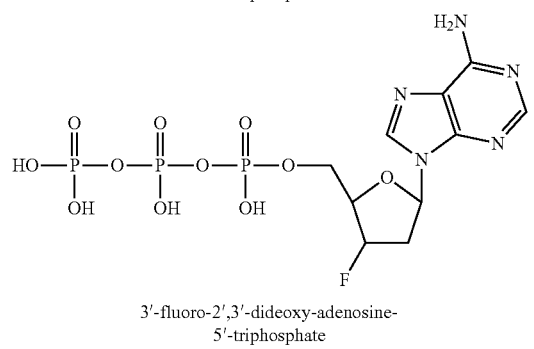

3'-fluoro-2',3'-dideoxy-adenosine-
5'-triphosphate

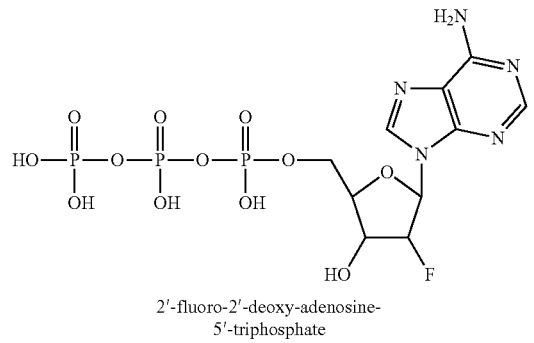

2'-fluoro-2'-deoxy-adenosine-
5'-triphosphate

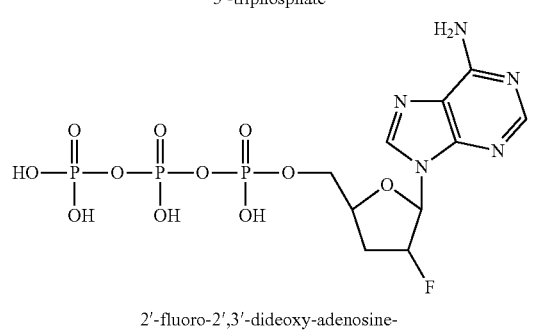

2'-fluoro-2',3'-dideoxy-adenosine-
5'-triphosphate

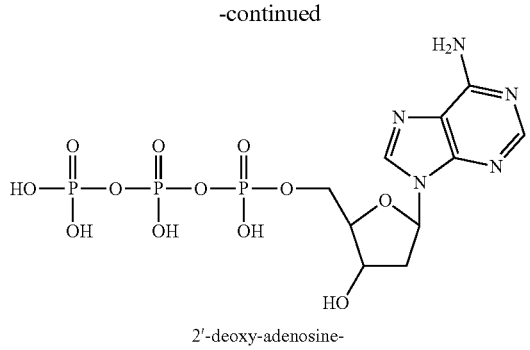

2'-deoxy-adenosine-
5'-triphosphate

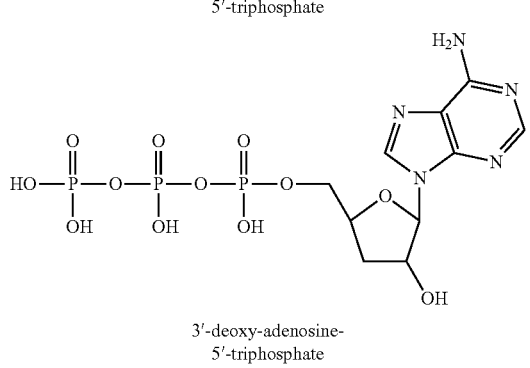

3'-deoxy-adenosine-
5'-triphosphate

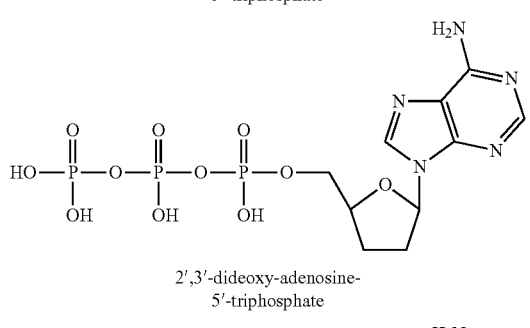

2',3'-dideoxy-adenosine-
5'-triphosphate

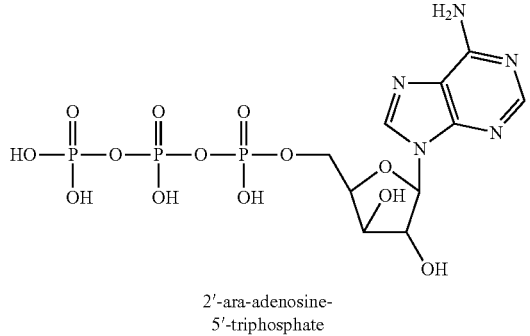

2'-ara-adenosine-
5'-triphosphate

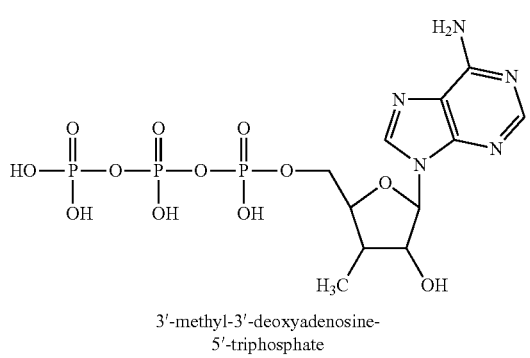

3'-methyl-3'-deoxyadenosine-
5'-triphosphate

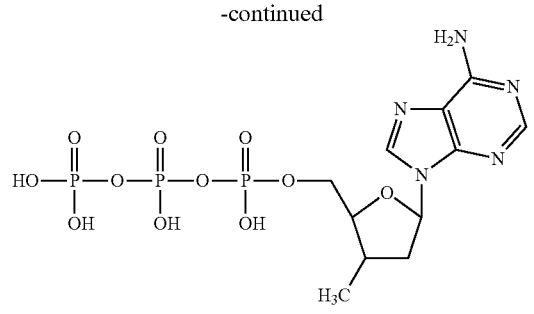

3'-methyl-2',3'-dideoxyadenosine-
5'-triphosphate

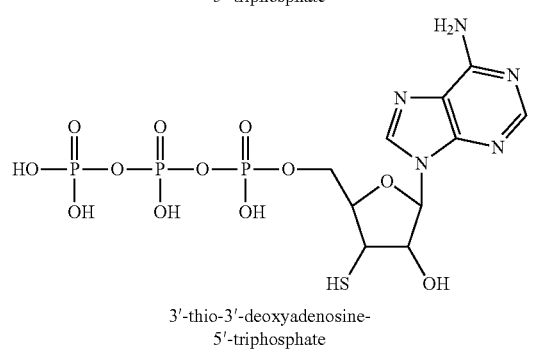

3'-thio-3'-deoxyadenosine-
5'-triphosphate

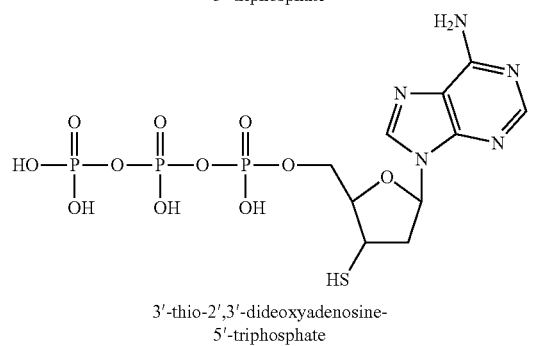

3'-thio-2',3'-dideoxyadenosine-
5'-triphosphate

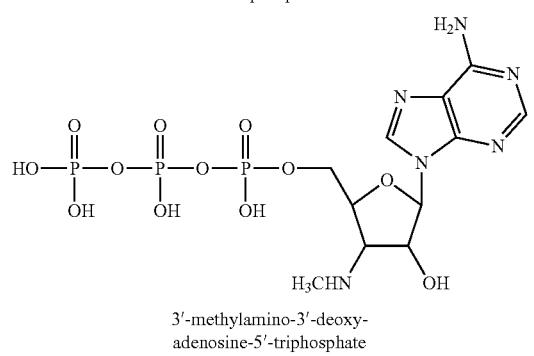

3'-methylamino-3'-deoxy-
adenosine-5'-triphosphate

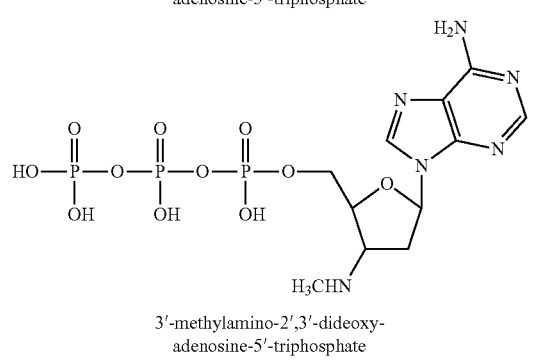

3'-methylamino-2',3'-dideoxy-
adenosine-5'-triphosphate

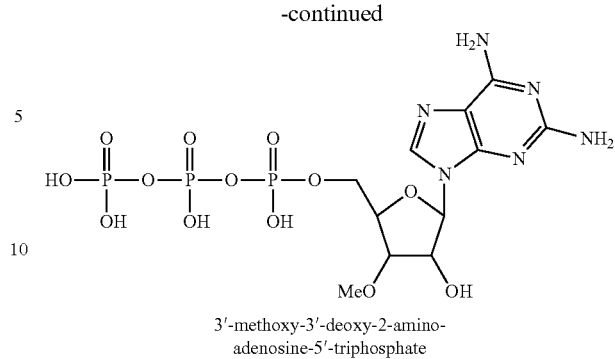

3'-methoxy-3'-deoxy-2-amino-
adenosine-5'-triphosphate

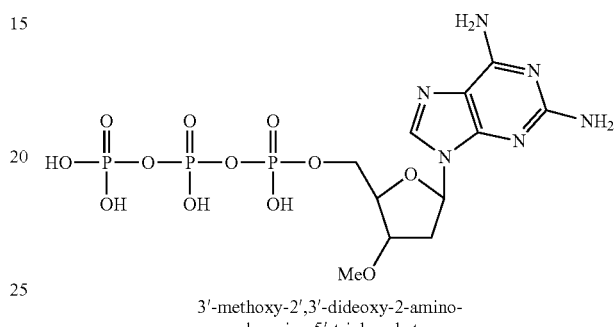

3'-methoxy-2',3'-dideoxy-2-amino-
adenosine-5'-triphosphate

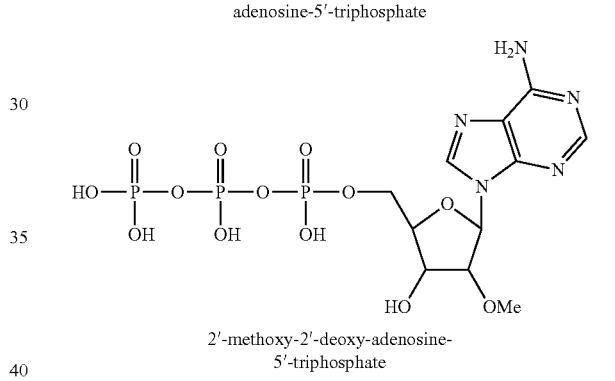

2'-methoxy-2'-deoxy-adenosine-
5'-triphosphate

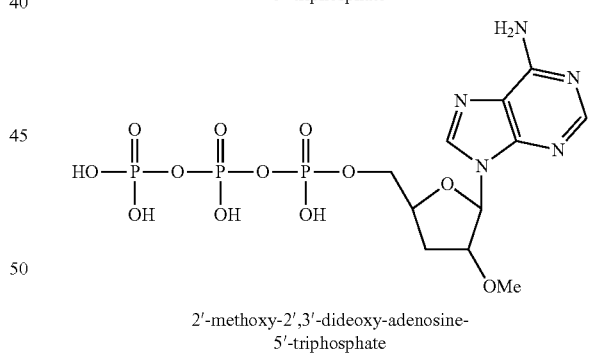

2'-methoxy-2',3'-dideoxy-adenosine-
5'-triphosphate

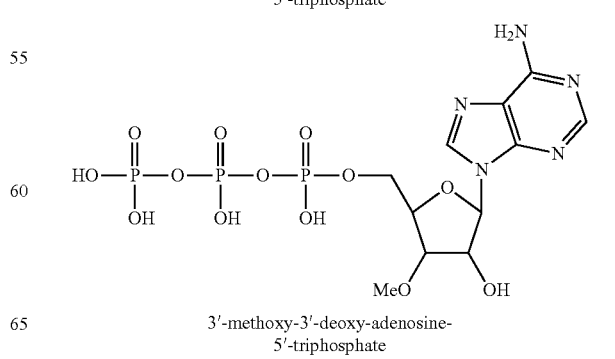

3'-methoxy-3'-deoxy-adenosine-
5'-triphosphate

-continued

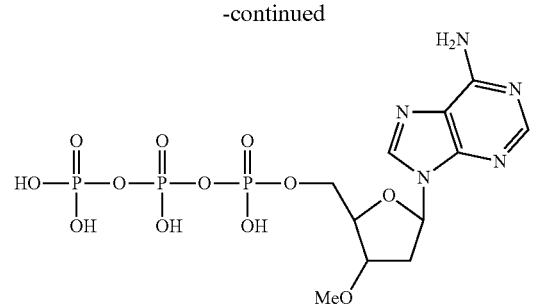

3'-methoxy-2',3'-dideoxy-adenosine-
5'-triphosphate

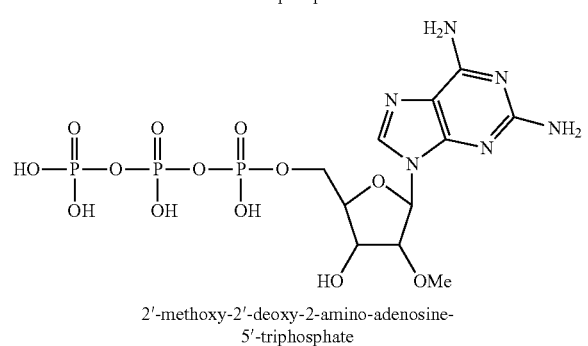

2'-methoxy-2'-deoxy-2-amino-adenosine-
5'-triphosphate

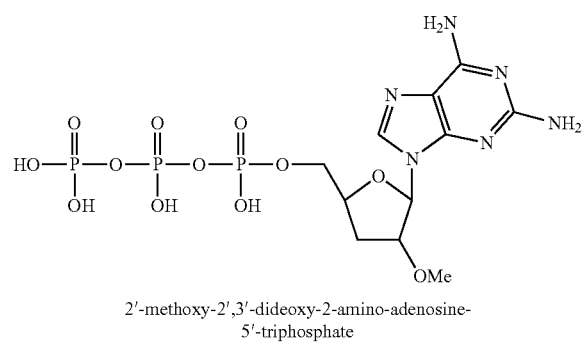

2'-methoxy-2',3'-dideoxy-2-amino-adenosine-
5'-triphosphate

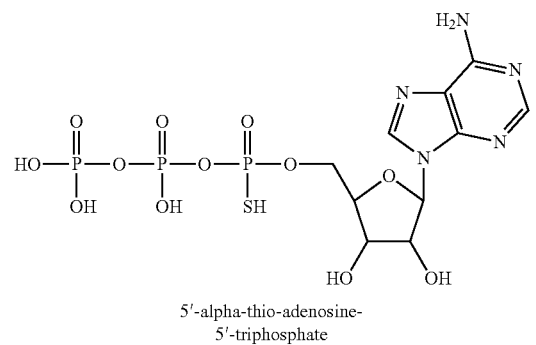

5'-alpha-thio-adenosine-
5'-triphosphate

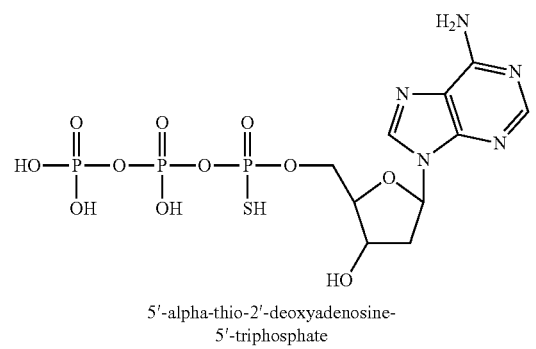

5'-alpha-thio-2'-deoxyadenosine-
5'-triphosphate

-continued

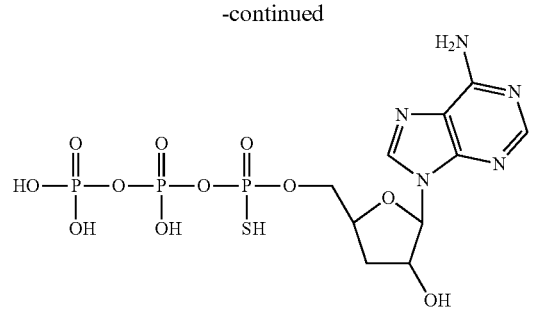

5'-alpha-thio-3'-deoxyadenosine-
5'-triphosphate

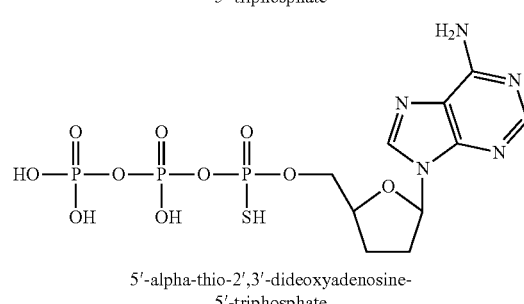

5'-alpha-thio-2',3'-dideoxyadenosine-
5'-triphosphate

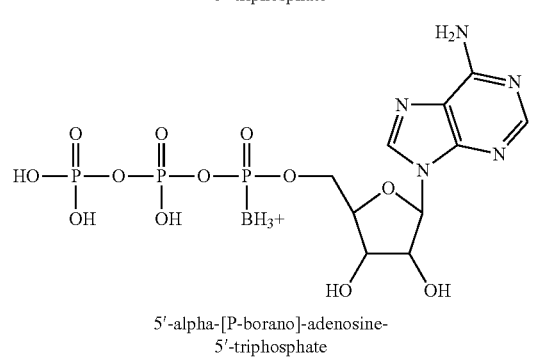

5'-alpha-[P-borano]-adenosine-
5'-triphosphate

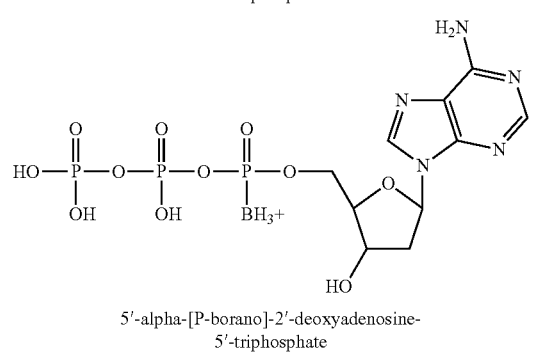

5'-alpha-[P-borano]-2'-deoxyadenosine-
5'-triphosphate

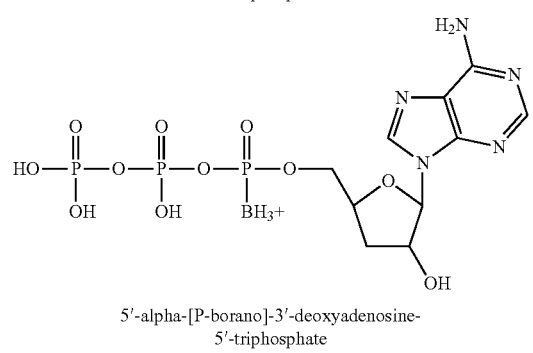

5'-alpha-[P-borano]-3'-deoxyadenosine-
5'-triphosphate

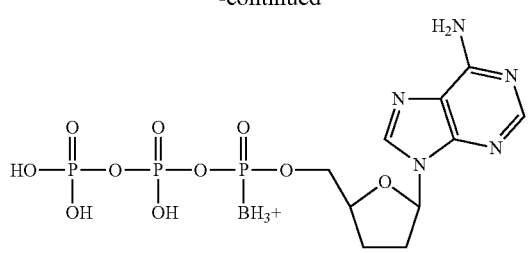

5′-alpha-[P-borano]-2′,3′-dideoxyadenosine-5′-triphosphate

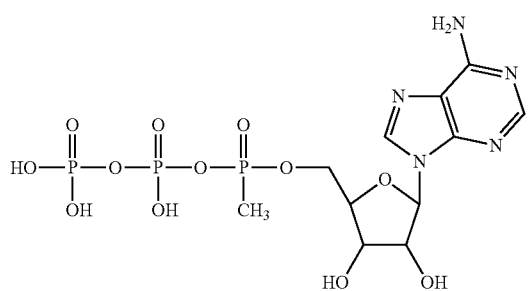

5′-alpha-methylphosphonate-adenosine-5′-triphosphate

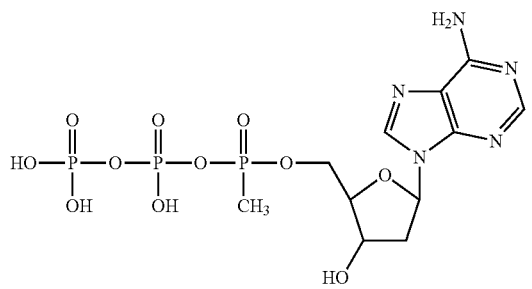

5′-alpha-methylphosphonate-2′-deoxyadenosine-5′-triphosphate

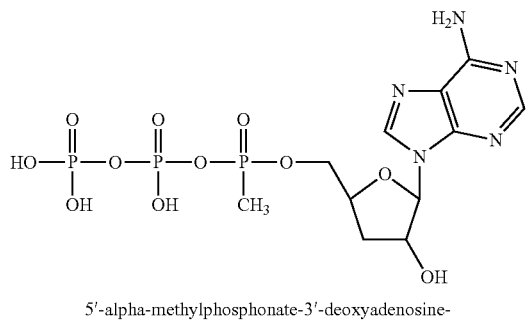

5′-alpha-methylphosphonate-3′-deoxyadenosine-5′-triphosphate

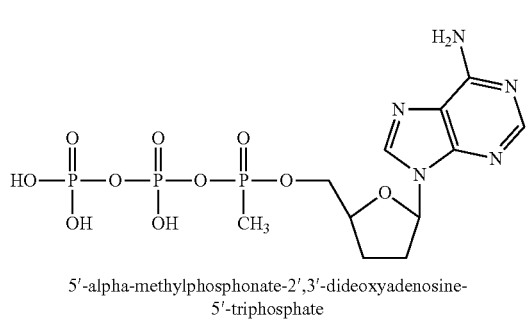

5′-alpha-methylphosphonate-2′,3′-dideoxyadenosine-5′-triphosphate

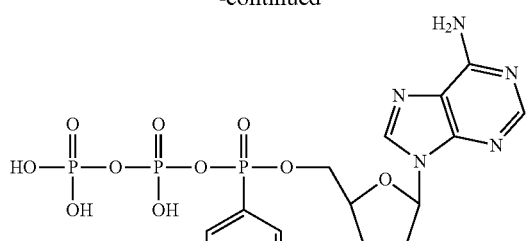

5′-alpha-phenylphosphonate-adenosine-5′-triphosphate

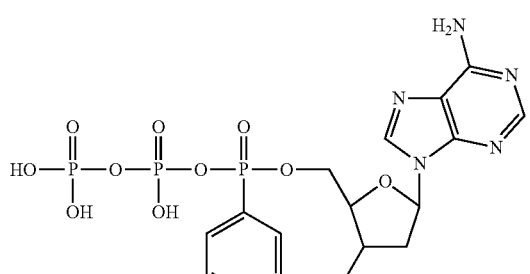

5′-alpha-phenylphosphonate-2′-deoxyadenosine-5′-triphosphate

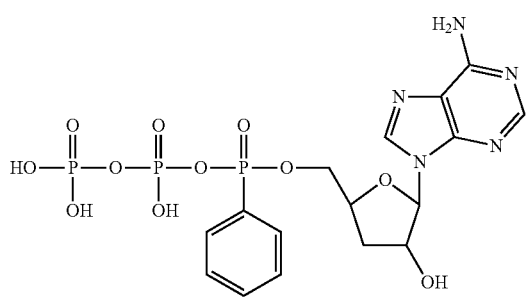

5′-alpha-phenylphosphonate-3′-deoxyadenosine-5′-triphosphate

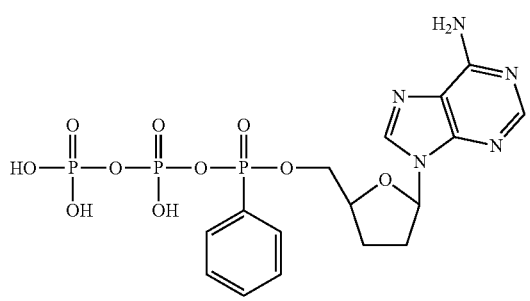

5′-alpha-phenyllphosphonate-2′,3′-dideoxyadenosine-5′-triphosphate

Particularly preferred combinations of modified ligase components are selected from the modified acceptors, modified donors and modified cofactors as follows:

Modified Acceptors:

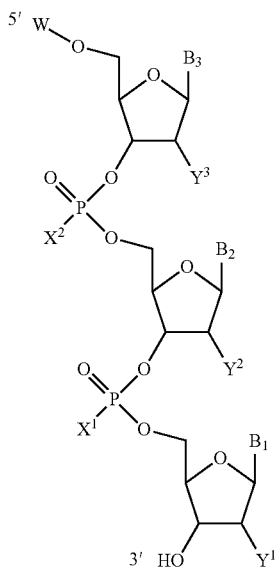

wherein:
- $B^1$, $B^2$, and $B^3$ are each independently selected from the group consisting of a substituted or non-substituted purine or pyrimidine, any aza or deaza derivative thereof, and any "universal base" or "degenerate base", which is preferably recognizable by a nucleic acid polymerase or ligase;
- $X^1$ is selected from the group consisting of H, OH, SH, $OCH_2CH_3$, and $CH_3$;
- $X^2$ is selected from the group consisting of H, OH, SH, $OCH_2CH_3$, and $CH_3$;
- $Y^1$, $Y^2$, and $Y^3$ are each independently selected from the group consisting of H and $OCH_3$; and
- W is selected from H or an oligonucleotidyl residue.

Modified Donors:

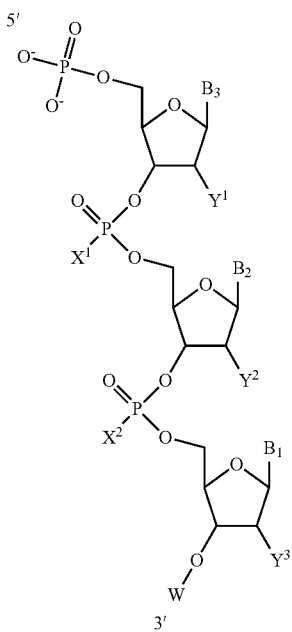

wherein:
- $B^1$, $B^2$, and $B^3$ are each independently selected from the group consisting of a substituted or non-substituted purine or pyrimidine, any aza or deaza derivative thereof, and any "universal base" or "degenerate base", which is preferably recognizable by a nucleic acid polymerase or ligase;
- $X^1$ and $X^2$ are each independently selected from the group consisting of OH, SH, $OCH_2CH_3$, and $CH_3$;
- $Y^1$, $Y^2$, and $Y^3$ are each independently selected from the group consisting of H, and $OCH_3$; and
- W is selected from H or an oligonucleotidyl residue.

Modified Cofactors:

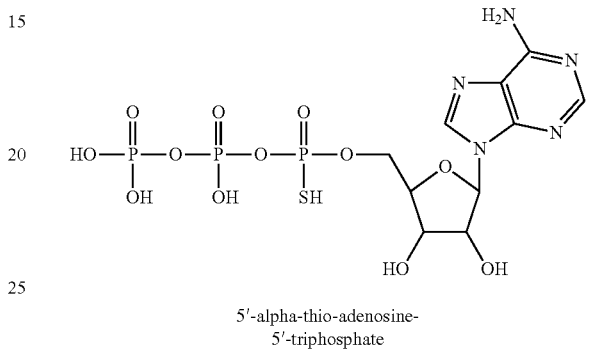

5'-alpha-thio-adenosine-5'-triphosphate

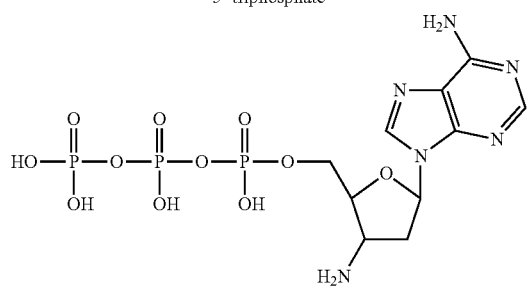

3'-amino-2',3'-dideoxy-adenosine-5'-triphosphate

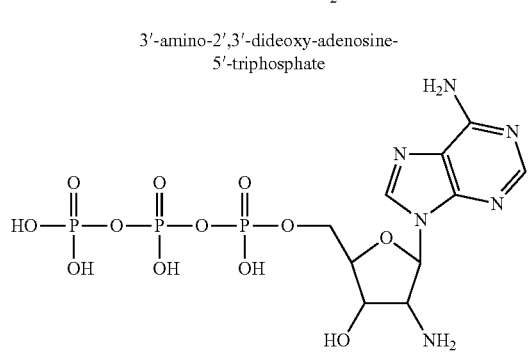

2'-amino-2'-deoxy-adenosine-5'-triphosphate

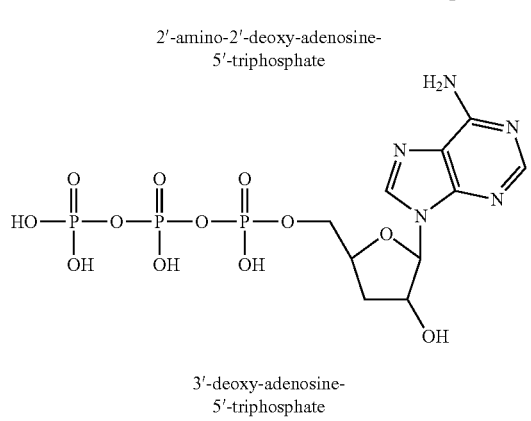

3'-deoxy-adenosine-5'-triphosphate

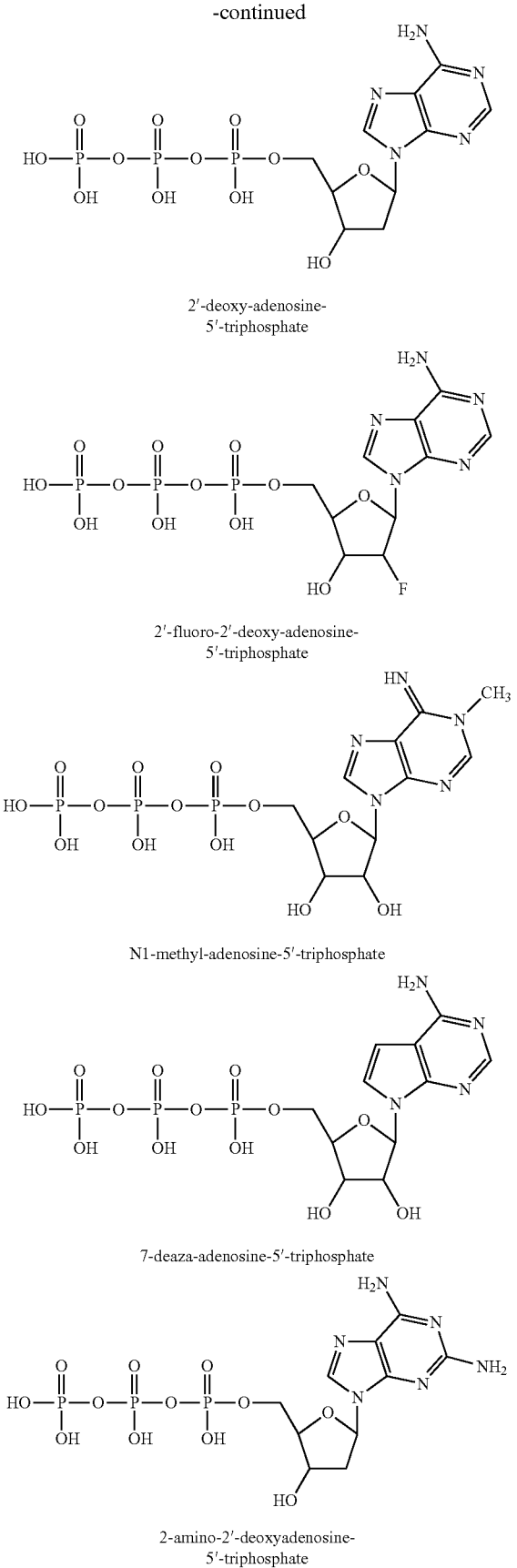

2'-deoxy-adenosine-5'-triphosphate

2'-fluoro-2'-deoxy-adenosine-5'-triphosphate

N1-methyl-adenosine-5'-triphosphate 7-deaza-adenosine-5'-triphosphate 2-amino-2'-deoxyadenosine-5'-triphosphate In one aspect, the methods and compositions herein provide for modified ligase components. In some embodiments, the modified ligase components may have only one substitution group. In other embodiments, the modified ligase components may contain more than one substitution group such as modifications at the base, triphosphate chain, sugar, or combinations thereof. In other embodiments, the modified ligase components may contain more than one type of substitution group. The modified ligase components may have the chemical formula of Formulas I-III described herein.

In another aspect, provided herein are methods of synthesis of modified ligase components having a chemical structure as depicted in Formulas I-III further described herein. The substitution groups, can be integrated into a ligase cofactor, acceptor or donor by using existing synthetic or enzymatic methods. The modified ligase components of the methods and compositions provided herein may be synthesized by any methods well-known in the art. Following synthesis and purification of a modified ligase components, several different procedures may be utilized to determine the acceptability of the modified ligase components in terms of structure and purity. Examples of such procedures are Nuclear Magnetic Resonance Spectroscopy, Mass Spectrometry, Fluorescent Spectroscopy, Ultra Violet Spectroscopy, High Performance Liquid Chromatography. These procedures are well known to those skilled in the art. Current methods employed for separation, purification and analysis in the art are applicable to the modified ligase components of the methods and compositions provided herein as well.

Any substitution group that accomplishes the purposes of the methods and compositions provided herein may be utilized. The substitution group should be one which use reduces or impairs undesired ligation product formation under conditions of a ligation reaction in which the modified ligase components are to be employed.

In some embodiments, the modified ligation components improve ligation specificity compared with the corresponding unmodified ligase component. Improving ligation refers to the ability of the ligase to discriminate between matched nucleic acid and mismatched nucleic acid. Preferably, the presence of the modified ligation component reduces or prevents ligation when there is one mismatch in the donor and/or acceptor as compared to the target nucleic acid (e.g., template). In other embodiments, the modified ligation components improve ligation specificity by decreased efficiency of ligation of mismatched (noncomplementary) nucleic acid targets. In preferred embodiments, the modified ligation components improve ligation specificity by decreasing the efficiency of ligation of nucleic acids with at least one base pair mismatch compared with matched nucleic acid. In preferred embodiments, ligation with a modified ligation component is improves ligation specificity by at least at least 0.1%, 0.2%, at least 0.5%, at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, at least 90%, at least 100%, at least 150%, at least 200%, at least 300%, or at least 400%.

In some ligation reactions, not all ligase cofactor, acceptor and/or donor molecules in the ligation reaction will contain a substitution group. Preferably, even a mixture of both modified ligase cofactor and unmodified ligase cofactor improves efficacy and specificity of ligation in a mixed population, as compared to not using modified ligase cofactors at all. Preferably, prior to incubation at an initial denaturation temperature, modified ligase cofactors make up at least 25% of total ligase cofactor molecules, preferably at least 50% of total ligase cofactor molecules, preferably at least 75% of total ligase cofactor molecules and preferably at least 90% of total ligase cofactor molecules, preferably at least 95% of total ligase cofactor molecules, preferably at least 98% of total ligase cofactor molecules, more preferably at least 99% of total ligase cofactor molecules, and more preferably 100% of total ligase cofactor molecules. In another embodiment, two, three, four or more types of ligase cofactor molecules may be employed in the ligation reaction.

In one embodiment, only one type modified ligase cofactor is present in the ligation reaction. In other embodiments different types of modified ligase cofactor may be present in the same ligation reaction. In another embodiment, two or more types of modified ligase cofactors may be present in the same ligation reaction. In another embodiment, three or more types of modified ligase cofactors may be present in the same ligation reaction. In another embodiment, four or more types of modified ligase cofactors may be present in the same ligation reaction.

Exemplary ligation methods suitable for use with the modified ligase components provided herein include oligonucleotide ligation assay (OLA) (Landegren, U., et al., 241 Science, 1077-1080 (1988)), ligase chain reaction (LCR) (Wiedmann, M., et al., 3 Genome Biol, S51-64 (1994)), Ligase Mediated PCR (LM-PCR) (Mueller, P. R., et al., 246 Science, 780-786 (1989), Pfeifer, G. P., et al., 246 Science, 810-813 (1989)), PCR ligation detection reaction (PCR-LDR) (Cheng, Y. W., et al., 16 Genome Res, 282-289 (2006)), Padlock probes (Antson, D., et al., 28 Nucleic Acids Res, e58 (2000)), PCR oligonucleotide ligation assay (PCR-OLA) (Delahunty, C., et al., 58 Am J Hum Genet, 1239-1246 (1996)), gap LCR approach (Abravaya, K., et al., 23 Nucleic Acids Res, 675-682 (1995)), SNPlex (De la Vega, F. M., et al., 573 Mutat Res, 111-135 (2005), Livak, K. J. 14 Genet Anal, 143-149 (1999)), MLPA (multiplex ligation-dependent probe amplification) (Schouten, J. P., et al., 30 Nucleic Acids Res, e57 (2002)), GoldenGate Genotyping Assay (Fan, J. B., et al., 68 Cold Spring Harb Symp Quant Biol, 69-78 (2003), Oliphant, A., et al., Suppl Biotechniques, 56-58, 60-51 (2002), Shen, R., et al., 573 Mutat Res, 70-82 (2005)), and Molecular Inversion Probe Assay (Fodor, S. P., et al., 251 Science, 767-773 (1991), Matsuzaki, H. S., et al., 1 Nat Methods, 109-111 (2004), Matsuzaki, H., et al., 14 Genome Res, 414-425 (2004), Pease, A. C., et al., 91 Proc Natl Acad Sci USA, 5022-5026 (1994)), proximity ligation (Gustafsdottir, S., et al., 345 Anal Biochem, 2-9 (2005), Söderberg, O., et al., 28 Genet Eng (NY), 85-93 (2007)), and next-generation sequencing by ligation.

Exemplary ligation-based approaches for sequence detection suitable for use with the modified ligase components provided herein include those as described in Barany, F., et al., U.S. Pat. Nos. 7,244,831; 6,312,892 and the use of high fidelity thermostable ligases (U.S. Pat. No. 6,949,370), LDR and PCR coupling (Barany, F., et al., U.S. Pat. Nos. 7,097,980; 6,797,470; 6,268,148; 6,027,889; 7,166,434), ligation using an endonuclease (Barany, F., et al., U.S. Pat. Nos. 7,198,894; 7,014,994), OLA/PCR (Eggerding, F., U.S. Pat. Nos. 5,912,148; 6,130,073), ligation/amplification (Lao, K. Q., U.S. Pat. No. 7,255,994), stepwise ligation and cleavage (Brenner, S., et al., U.S. Pat. Nos. 5,714,330; 5,552,278), proximity ligation (Gustafsdottir, S., et al., 345 Anal Biochem, 2-9 (2005), Soderberg, O., et al., 28 Genet Eng (NY), 85-93 (2007), Fredriksson, S., et al., 20 Nat Biotechnol, 473-477 (2002)), proximity ligation for pathogen detection (Gustafsdottir, S. M., et al., 52 Clin Chem, 1152-1160 (2006)), cytokines detection (Gullberg, M., et al., 101 Proc Natl Acad Sci USA, 8420-8424 (2004)), spore detection (Pai, S., et al., 33 Nucleic Acids Res, e162 (2005)), cancer biomarker detection (Fredriksson, S., et al., 4 Nat Methods, 327-329 (2007)), and proximity ligation for measuring strength of protein-DNA interactions (Gustafsdottir, S., et al., 345 Anal Biochem, 2-9 (2005), Schallmeiner, E., et al., 4 Nat Methods, 135-137 (2007)).

Exemplary ligation-based diagnostic assays suitable for use with the modified ligase components provided herein include detection of HIV drug resistant strains (Lalonde, M., et al., 45 J Clin Microbiol, 2604-2615 (2007)) multiplexed detection of allele-specific products (Macdonald, S. J., et al., 6 Genome Biol, R105 (2005)), SNP detection by ligation including oligonucleotide ligation assay (OLA) (Landegren, U., et al., 241 Science, 1077-1080 (1988)), ligase chain reaction (LCR) (Wiedmann, M., et al., 3 Genome Biol, S51-64 (1994)), SNP detection using combinations of ligation and PCR including Ligase Mediated PCR (LM-PCR) (Mueller, P. R., et al., 246 Science, 780-786 (1989), Pfeifer, G. P., et al., 246 Science, 810-813 (1989)), PCR ligation detection reaction (PCR-LDR) (Cheng, Y. W., et al., 16 Genome Res, 282-289 (2006)), Padlock probes (Antson, D., et al., 28 Nucleic Acids Res, e58 (2000)), PCR oligonucleotide ligation assay (PCR-OLA) (Delahunty, C., et al., 58 Am J Hum Genet, 1239-1246 (1996)), and a gap LCR approach (Abravaya, K., et al., 23 Nucleic Acids Res, 675-682 (1995)), SNPlex (De la Vega, F. M., et al., 573 Mutat Res, 111-135 (2005), Livak, K. J. 14 Genet Anal, 143-149 (1999)), MLPA (multiplex ligation-dependent probe amplification) (Schouten, J. P., et al., 30 Nucleic Acids Res, e57 (2002)), Illumina's GoldenGate Genotyping Assay (Fan, J. B., et al., 68 Cold Spring Harb Symp Quant Biol, 69-78 (2003), Oliphant, A., et al., Suppl Biotechniques, 56-58, 60-51 (2002), Shen, R., et al., 573 Mutat Res, 70-82 (2005)), and Molecular Inversion Probe Assay on Affymetrix GeneChip arrays (Fodor, S. P., et al., 251 Science, 767-773 (1991), Matsuzaki, H., et al., 1 Nat Methods, 109-111 (2004), Matsuzaki, H., et al., 14 Genome Res, 414-425 (2004), Pease, A. C., et al., 91 Proc Natl Acad Sci USA, 5022-5026 (1994)).

Additional exemplary ligation assays suitable for use with the modified ligase components provided herein include traditional Sanger dideoxy sequencing (Sanger, F., et al., 74 Proc Natl Acad Sci USA, 5463-5467 (1977) and next generation sequencing assay such as 454 Sequencing System, the Illumina Genome Analyzer, Knome's KnomeCOMPLETE™ genome sequencing service, and the ABI SOLiD™ System sequencing technology and other sequencing by ligation assays (Ronaghi, M., 11 Genome Res, 3-11 (2001), Mirzabekov, A., 12 Trends Biotechnol, 27-32 (1994), Schmalzing, D., et al., 20 Electrophoresis, 3066-3077 (1999)).

Figure 9:
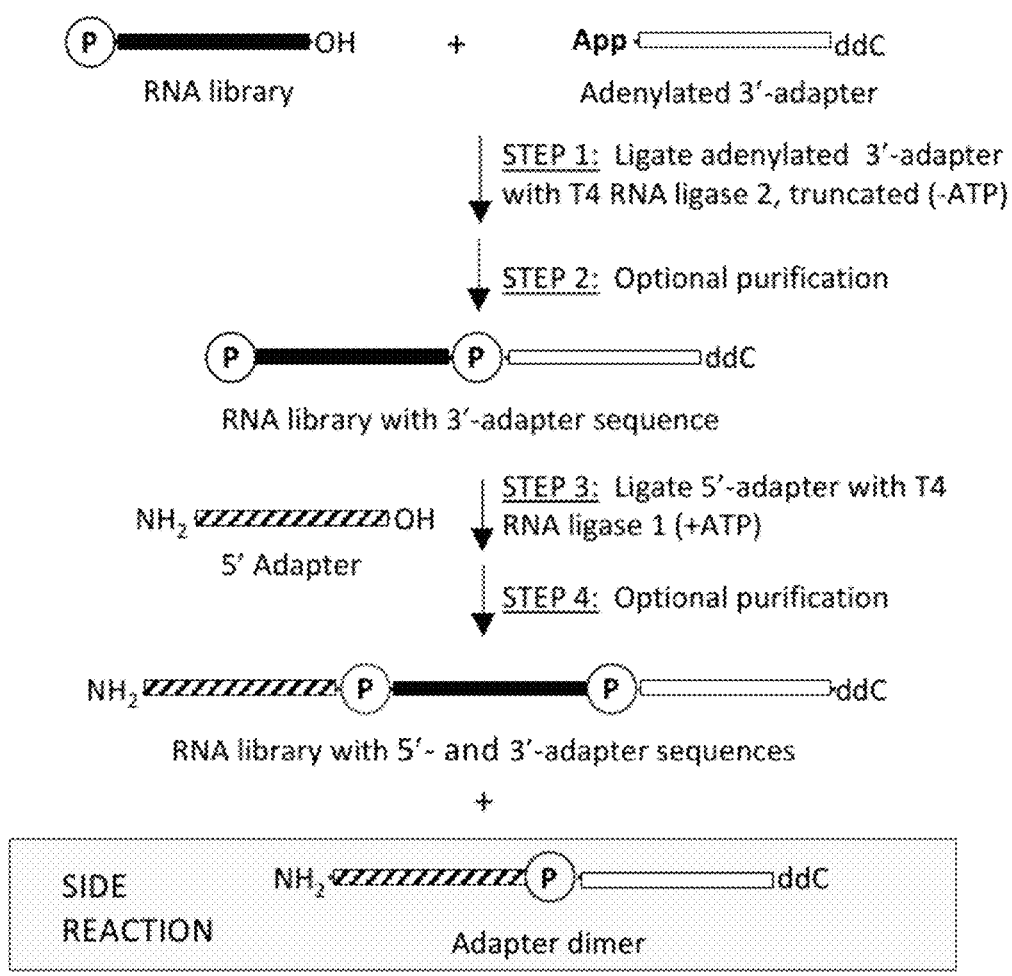
FIG. 9 is a schematic diagram of a traditional two step method for RNA library preparation showing adapter probe dimer formation.
Figure 12:
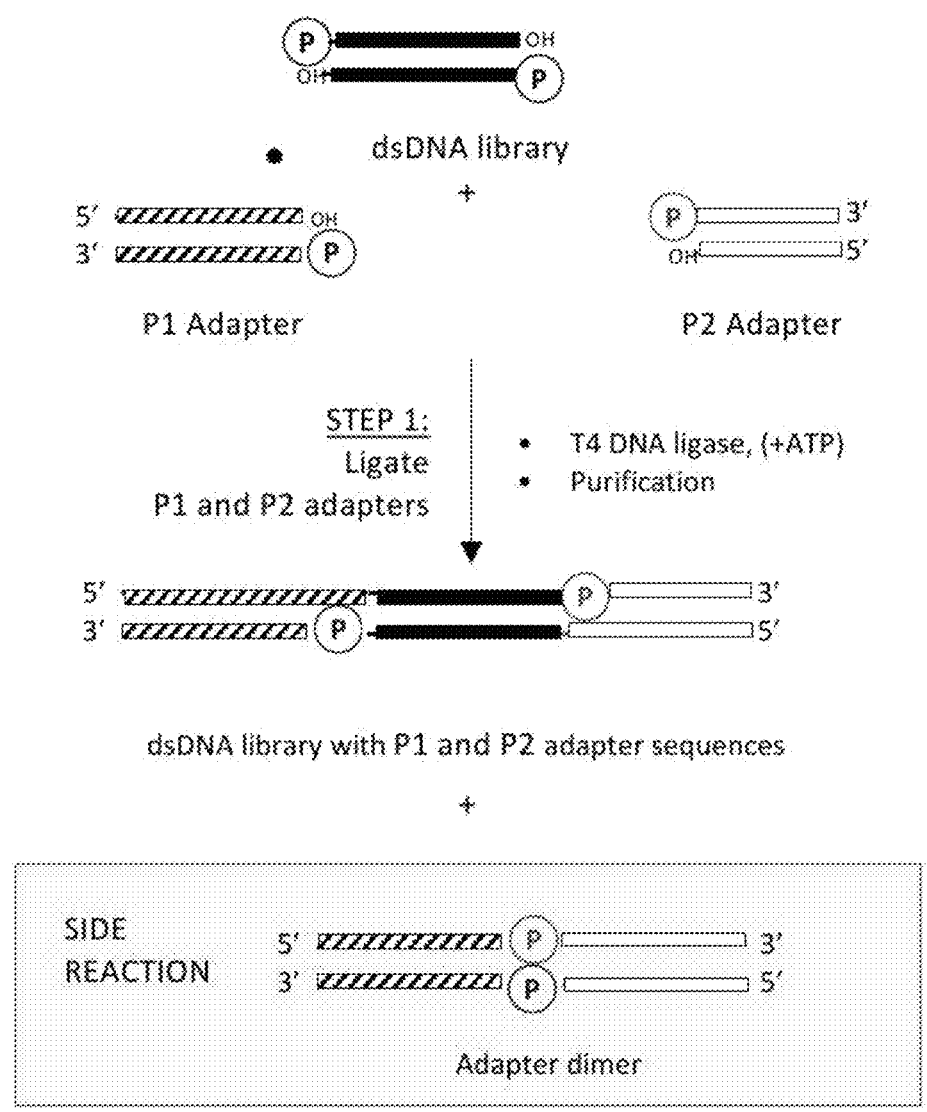
FIG. 12 is a schematic diagram of a traditional method for DNA library preparation utilizing blunt ended double stranded adapter probes.
Figure 14:
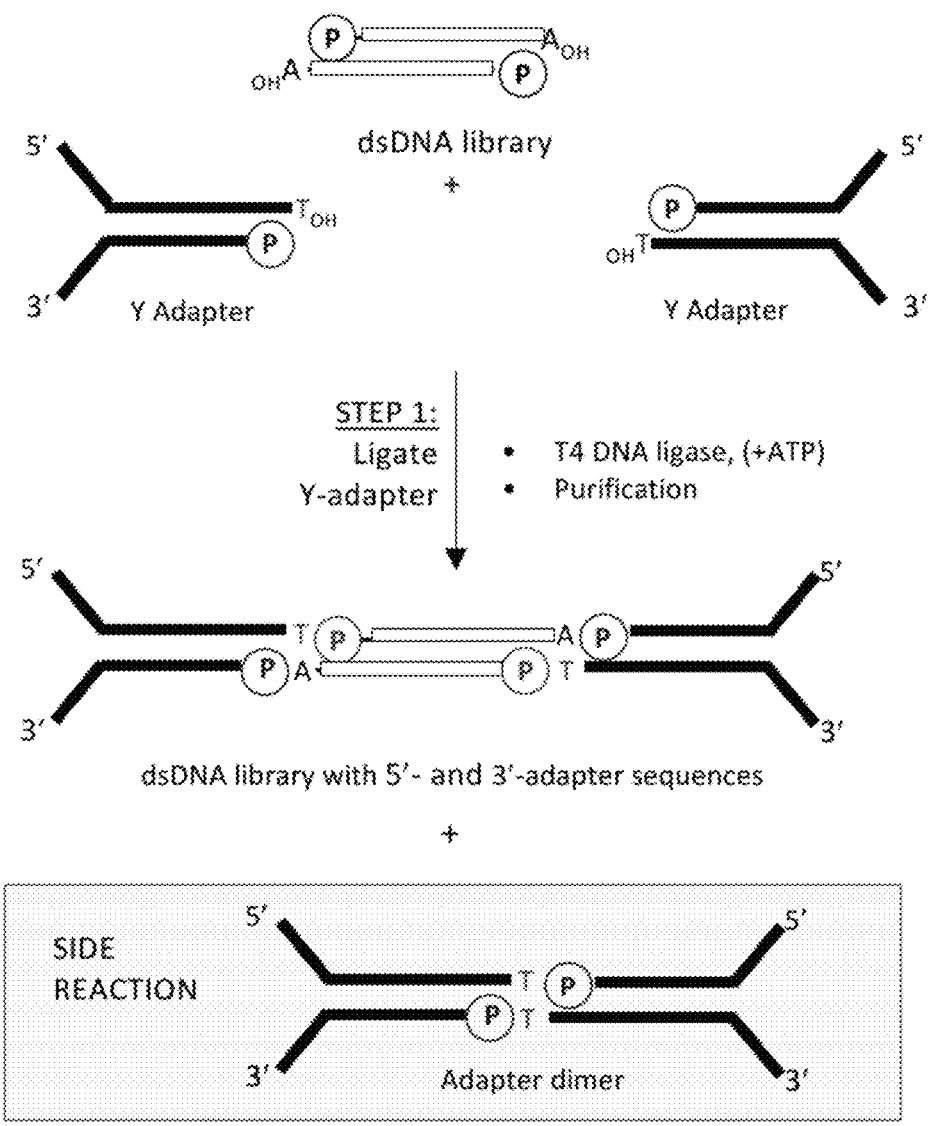
FIG. 14 is a schematic diagram of a traditional method for DNA library preparation utilizing adapters in a "Y" configuration with a T-tail.

Preparation of Nucleic Acid Libraries Utilizing Modified Ligase Cofactors, Modified Acceptor Probes and Modified Donor Probes Next generation sequencing technologies have advanced well beyond traditional Sanger dideoxy sequencing. There are several notable advantages offered by NGS technologies, including the ability to quickly produce gigabases of sequencing data at reduced costs. One common step in NGS sample preparation is the ligation of fixed sequences, called adapters, onto the 5'- and 3'-termini of the starting DNA or RNA library. The ligation step can be plagued by the undesired joining of the adapter sequences to one another without a segment of the library in between, resulting in adapter dimer formation (FIGS. 9, 12 and 14). Although approaches to remove adapter dimers have been developed, most involve a purification step or a selective priming step, which can result in sequence bias or depletion of low abundance sequences. To avoid making unintentional changes to the complexity of the library, it is advantageous to block adapter dimer formation at the ligation step.

Traditional sample preparation typically involves three steps: 1) fragmentation of input libraries into sizes compatible with the read length of the sequencing instrument, 2) introduction of adapter probe sequences onto the 5' and 3' termini of the library, and 3) amplification (FIG. 9). Adapter probe sequences can be introduced by probe ligation or through alternative strategies, such as transposon-based approaches. While the use of transposons has significant promise, there are concerns about library bias. Within ligation-based strategies for library preparation, high efficiency ligation conditions have been developed. However, there is a strong tendency for the 5'- and 3'-adapter probe sequences to ligate to one another forming dimers. "Adapter probe dimers" are undesirable because they reduce the number of functional reads in a NGS run and often necessitate a purification step for their removal. Although purification or selective priming steps can be introduced into the workflow, the complexity of the library can be depleted, especially for low abundance sequences within the population.

Figure 10:
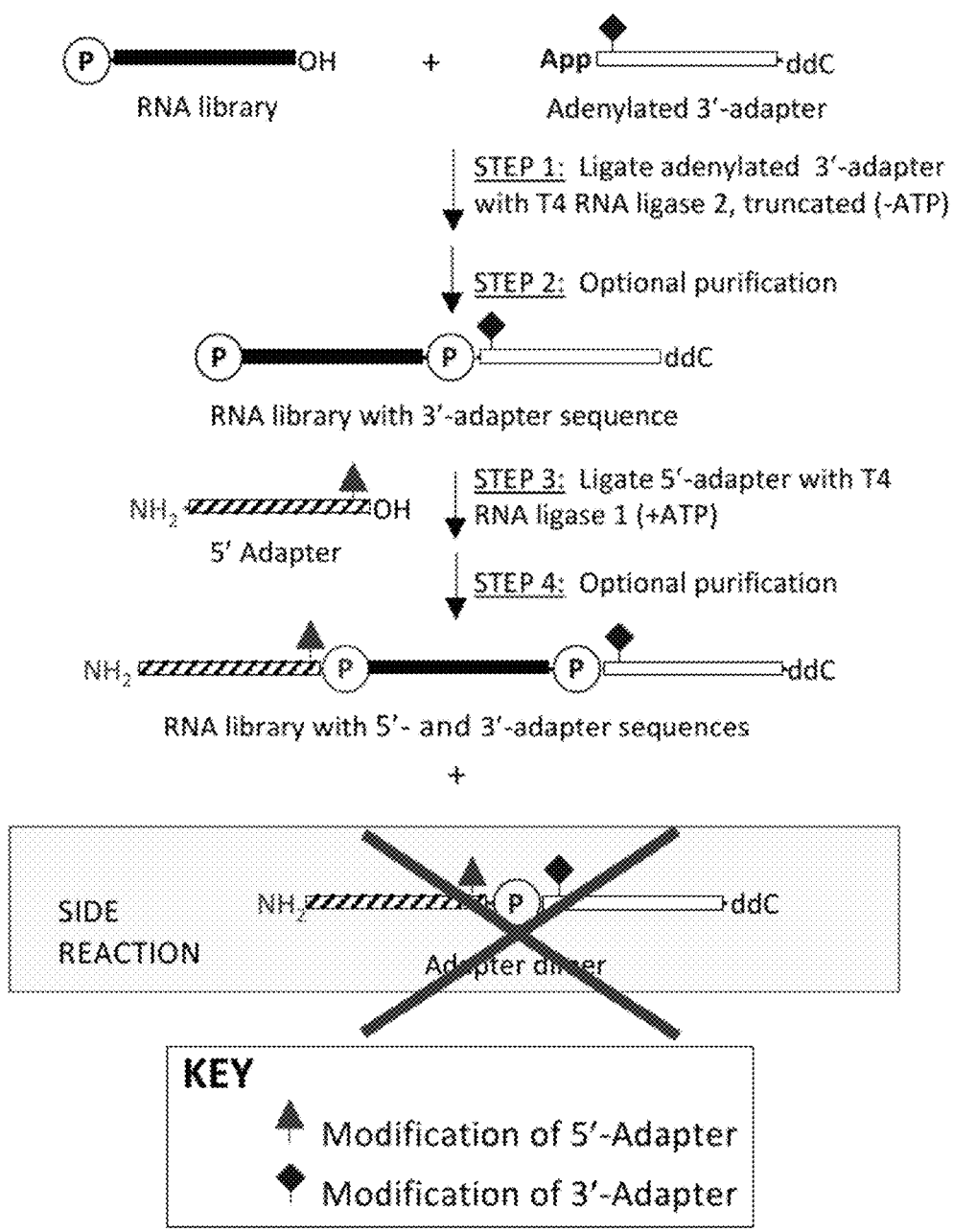
FIG. 10 is a schematic diagram of a modified two step method for RNA library preparation according to the present invention that interfers with or prevents dimerization of adapter probes.
Figure 11:
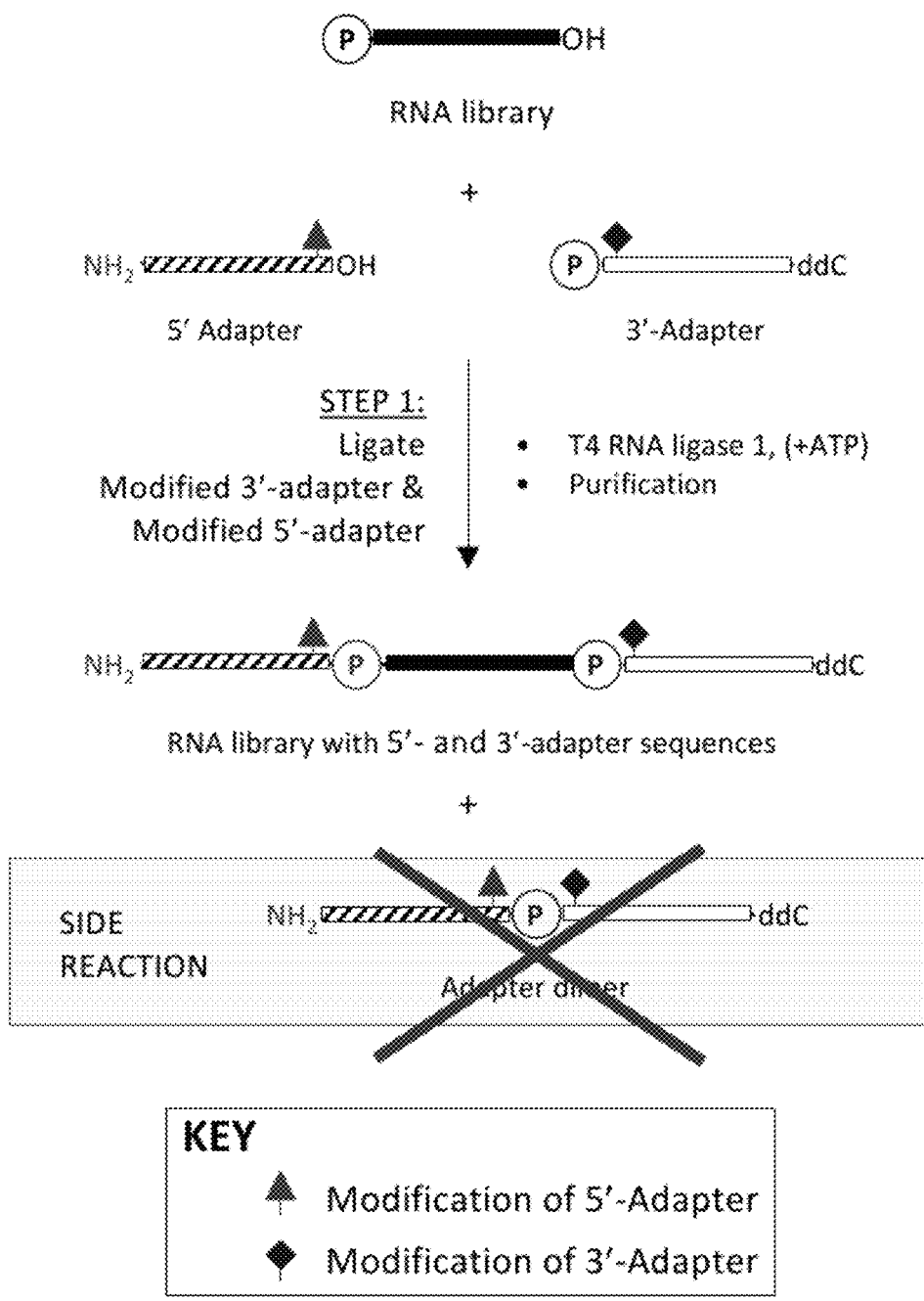
FIG. 11 is a schematic diagram of a modified one step method for RNA library preparation according to the present invention that interfers with or prevents dimerization of adapter probes without purification after the first ligation step.

One aspect of the present invention provides 3'- and 5'-modified adapter probes (i.e. modified acceptor probe and modified donor probe respectively) are added to the library preparation reaction in two sequential ligation steps to minimize adapter probe dimer formation when preparing RNA libraries (FIG. 10). First, an adenylated version of the 3'-modified adapter probe is ligated onto the 3'-termini of the RNA library, in the absence of ATP, using a specialized version of T4 RNA ligase that uses 5'-adenylated, rather than 5'-phosphorylated probes. Next, the 5'-modified adapter probe sequence is added onto the 5'-terminus of the RNA library using T4 RNA ligase 1. In this approach, a pair of modified 5'- and 3'-adapter probe constructs block adapter probe dimer formation while allowing for efficient formation of the adapter-tagged RNA library. This makes the library preparation reaction more specific, allowing for the two reaction steps to be combined into one (FIG. 11). This further streamlining of workflows is advantageous for several reasons. First, the two sequential purification steps outlined in FIG. 9 will be reduced to a single purification step, which will minimize the chance ligase I, eliminating the need for two enzymes in the workflow. Third, by removing the specialized version of T4 RNA ligase, there is no longer the need for the use of a 5'-adenylated version of the 3'-modified adapter probe. The switch to using 5'-phosphorylated adaptor probes rather than 5'-adenylated probes will reduce the cost of the 3'-adapter probe component. Furthermore, this approach will obviate the need for complicated enzymatic steps to prepare adenylated probes. A fourth benefit is that the presence of two adjacent modifications (only present in adapter dimers) could block the extension of reverse transcriptase used in downstream steps, allowing for selective cDNA synthesis of adapter tagged libraries. This would potentially eliminate another purification step from the protocol.

In one aspect, after ligation of the modified adapter probes onto the nucleic acid library, a variety of downstream processing steps can be performed. In one embodiment, the resultant reaction mixture is replicated by a nucleic acid polymerase, such as a DNA polymerase, and RNA polymerase, or a reverse transcriptase. Should any adapter dimer formation arise from the library preparation workflow, it would contain two adjacent modifications. The presence of these sequential modifications will reduce or inhibit replication of the modified adapter dimers by nucleic acid polymerase relative to unmodified adapter dimers. This property further suppresses the level of adapter dimers in the final library, allowing for more specific library formation and downstream next generation sequencing.

Figure 16:
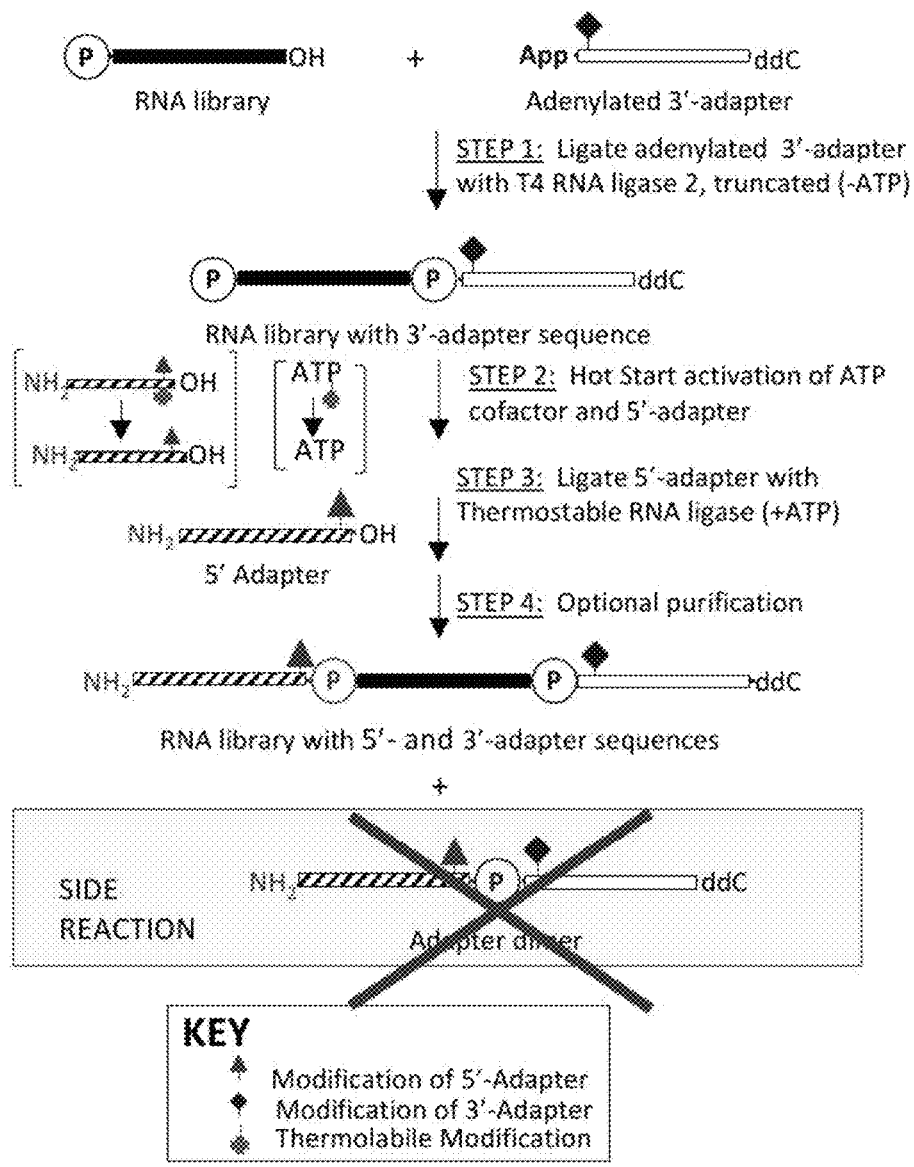
FIG. 16 is a schematic diagram of a modified method for RNA library preparation according to the present invention utilizing cofactor dependent ligase with modified adapters and ligase cofactor comprising thermally labile protection groups.

In one embodiment of this aspect the 3'- and 5'-modified adapter probes further comprise thermally labile substitution groups (FIG. 16). The substitution group cleaves or dissociates during and after the initial heat denaturation step of the ligase reaction. Donor probes, acceptor probes and cofactors having thermally labile substitution groups are described in more detail in patent application PCT/US2012/020109 filed Jan. 3, 2012 and incorporated by reference herein in its entirety. In some embodiments, the thermolabile substitution group is attached modified adapter probes creating, for example, a bulky PTE internucleotide linkage near the 3' end of a modified acceptor probe or the 5'-terminus of a modified donor probe. The bulky PTE group impedes a ligase catalyzed phosphodiester bond formation between adjacent 3'-hydroxyl group of the acceptor probe and 5'-phosphoryl termini of the modified donor probe on a nucleic acid template (e.g., RNA or DNA) prior to the initial heat denaturation step, Hot Start. The modified donor and acceptor probes can have a single substitution site or multiple substitution sites.

The modified adapter probes comprising thermally labile substitution groups disclosed herein have two states. In the first state, the modified adapter probe is in inactive due to the presence of a substitution group, which impedes formation of ligation product prior the initial activation temperature is reached, often 95° C. Upon reaching the initial activation temperature, the modified adapter probe releases the substitution group by a thermally induced intra- or intermolecular fragmentation reaction and transforms to a second state. In the second state, partial or complete dissociation or cleavage of the substitution group preferably occurs after incubation of the modified adapter probe at approximately 95° C. for approximately 0.1-120 minutes. In certain embodiments, dissociation of the substitution group from the modified adapter probe occurs in respect to temperature and does not require other enzymes, chemicals, or specific ligation reaction conditions. Thermolabile substituted internucleotide linkages are described in Beaucage et. al., U.S. Pat. No. 6,762,298; Zon et al., U.S. Patent application 20070281308; Lebedev, Current Protocols in Nucleic Acid Chemistry, Wiley Interscience 2009, unit 4.35; Ashrafi et al., Current Protocols in Molecular Biology, Wiley Interscience 2009, unit 15.9. Hidalgo-Ashrafi, et al., BioTechniques 2009, 47(3): 789-90; Lebedev, et. al. Nucleic Acids Research 2008, 36(20): 131; Shum et al., Analytical Biochemistry 2009, 388: 266-272; Hidalgo-Ashrafi et. al. BSC Molecular Biology 2009, 10: 113.

Figure 13:
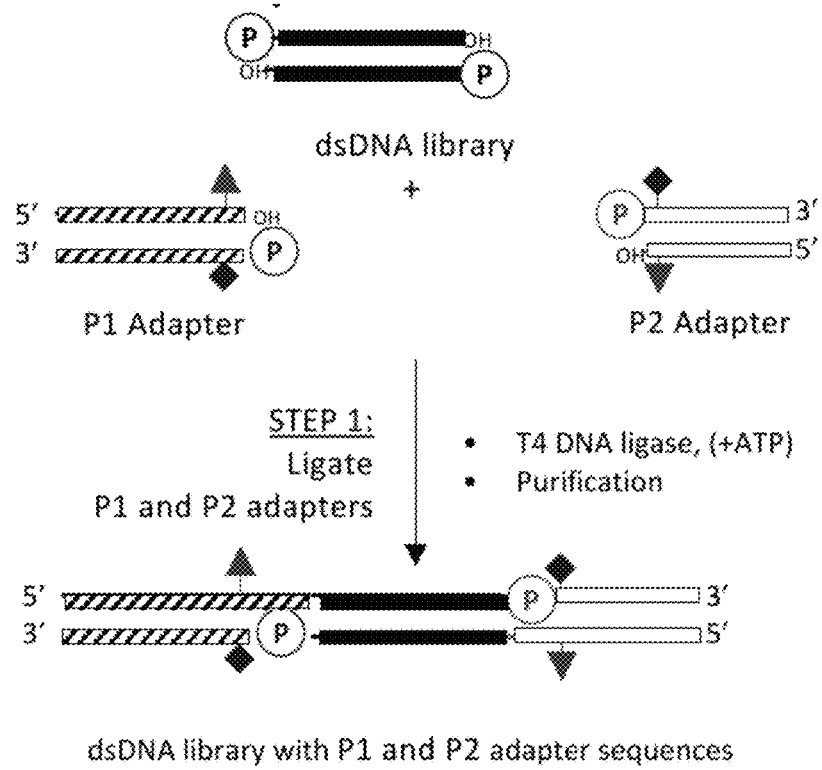
FIG. 13 is a schematic diagram of a modified method for DNA library preparation according to the present invention utilizing double stranded adapter probes with modifications on both strands of each adapter probe.
Figure 13:
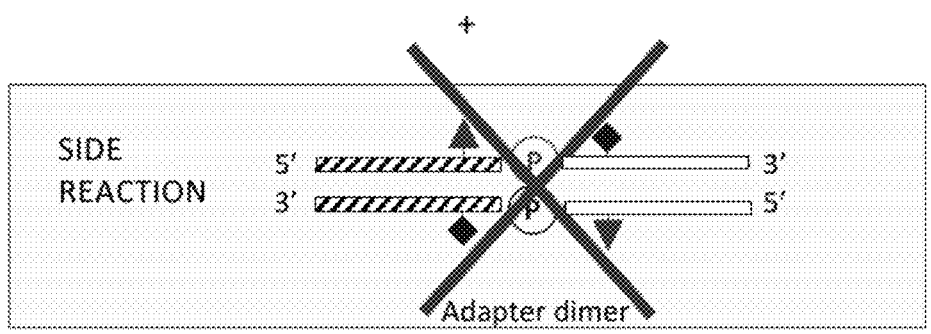
Figure 13:
Figure 15:
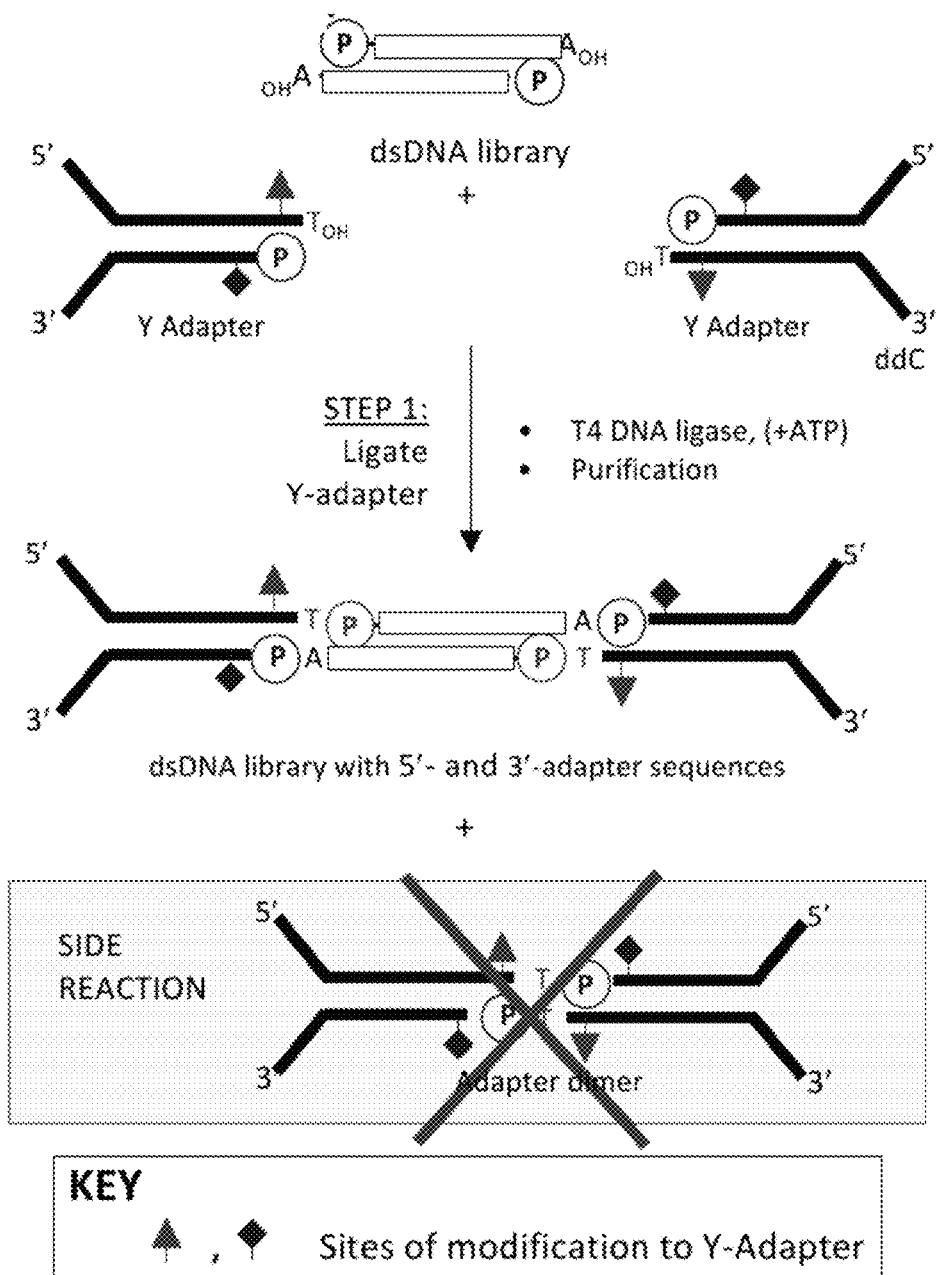
FIG. 15 is a schematic diagram of a modified method for DNA library preparation according to the present invention utilizing double stranded adapter probes in a "Y" configuration with modifications on both strands of each adapter probe.
Figure 21:
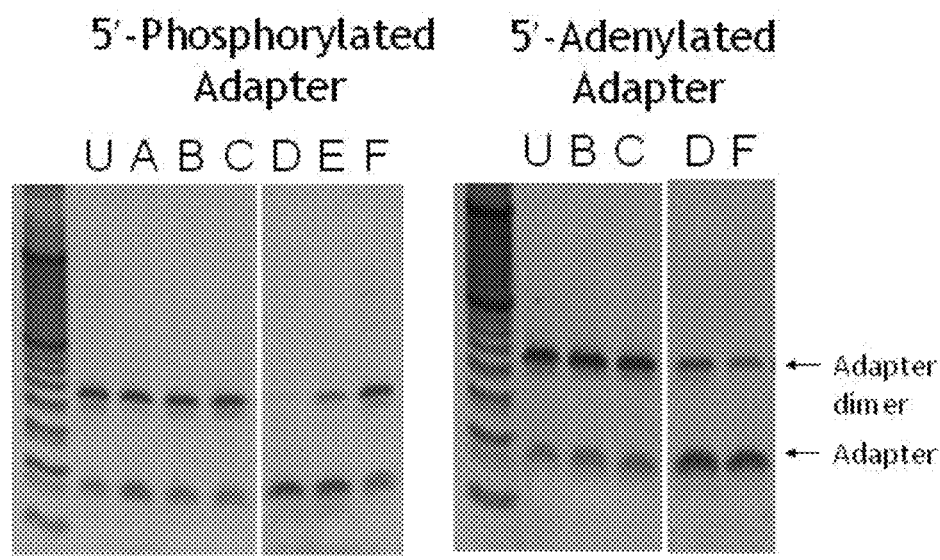
FIG. 21 is a polyacrylamide gel electrophoresis image showing adapter dimer suppression in a DNA library preparation workflow using modified 5'- and 3'-adapters hybridized to form a modified double stranded blunt ended adapter probe construct and T4 DNA ligase.
Figure 22:
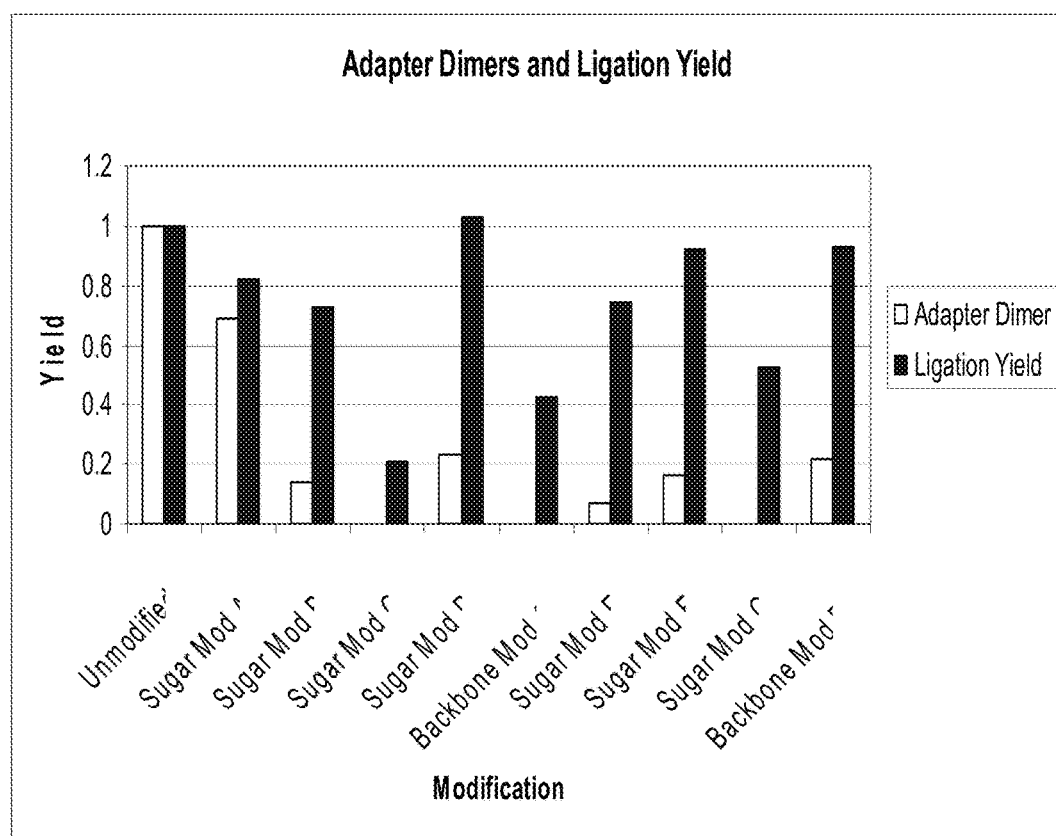
FIG. 22 is a bar graph representing adapter dimer suppression and tagged library formation in a DNA library preparation workflow using modified 5'- and 3'-adapters hybridized to form a modified double stranded blunt ended adapter probe construct and T4 DNA ligase.

Another aspect of the present invention provides modified double stranded adapter probes added may be utilized to minimize adapter probe dimer formation when preparing dsDNA libraries. The modified adapter probes are double stranded in nature and may be blunt ended (FIG. 13) or may have an overlapping nucleotide (FIG. 15). Furthermore, the double stranded adapter probes may contain a 5'-phosphate or a 5'-adenylate. In the traditional approach (FIGS. 12 and 14), the double stranded adapter sequences are added onto both ends of the dsDNA library using T4 DNA ligase. Blunt ended double stranded adapter ligation strategies and T-tailed double stranded adapter ligation strategies are typical platforms for preparing dsDNA libraries. Each of these approaches is prone to adapter dimer formation. To overcome adapter probe dimer formation, a modified version of the P1 and P2 double stranded adapter probes block the undesired side reaction (FIG. 21). Although two modifications are indicated on each double stranded adapter probe construct, a single modification (to either the sense or antisense strand) of the probe construct can provide suppression of adapter-adapter ligation. In this approach, the presence of two or more modifications at the ligation junction suppresses ligation of adapter probe dimers. In addition, the modified double stranded adapter probes may be combined with the target dsDNA fragments reducing adapter dimer formation as compared to traditional methods (FIG. 22). Furthermore, the dual suppression of ligation and DNA polymerase extension by the modifications in adapter probe dimers has the potential to eliminate the purification step from Step 1 of the workflow.

Figure 17:
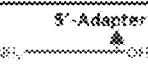
FIG. 17 (A) is a table of dimer ligation yields for library preparation using unmodified 3'-adapter in combination with modified 5'-adapter and (B) unmodified 5'-adapter in combination with modified 3'-adapter. Ligation yield is relative to the corresponding unmodified adapter probe (++++: 75-100%; +++: 50-74%; ++: 25-49%; +: 1-25%; –: not detected).

Modifications are introduced near the 3'-end of the 5'-adapter probe and near the 5'-end of the 3'-adapter probe. These modifications include 2'-fluoro- and 2'-methoxy sugar modifications and backbone modifications such as phosphorothioate and methylphosphonate, all of which are compatible with DNA and RNA polymerases. More specifically, adapter probes containing these modifications do not significantly suppress or interfere with ligation and replication when joined to a nucleic acid library. The modified 5'- and 3'-adapter probe's ability to suppress adapter probe dimer formation is determined by ligation experiments in the absence of 5'-phosphorylated synthetic RNA. In these experiments, modified 5'-adapter probes are ligated in the presence of unmodified 3'-adapter probes to assess the modified 5'-adapter probes that do not suppress ligation yield (score of +++ to ++++, FIG. 17A) relative to an unmodified 5'-adapter probe. Likewise, 3'-adapter probes are assessed by ligation to unmodified 5'-adapter probes without suppression ligation yield (score of +++ to ++++, FIG. 17A) relative to an unmodified 3' adapter probe. Modified 5'- and 3'-adapter probes that provide the desired results are combined and ligated with one another to identify combination(s) that suppress adapter probe dimer formation (score of − to +, FIG. 18).

Figure 19:
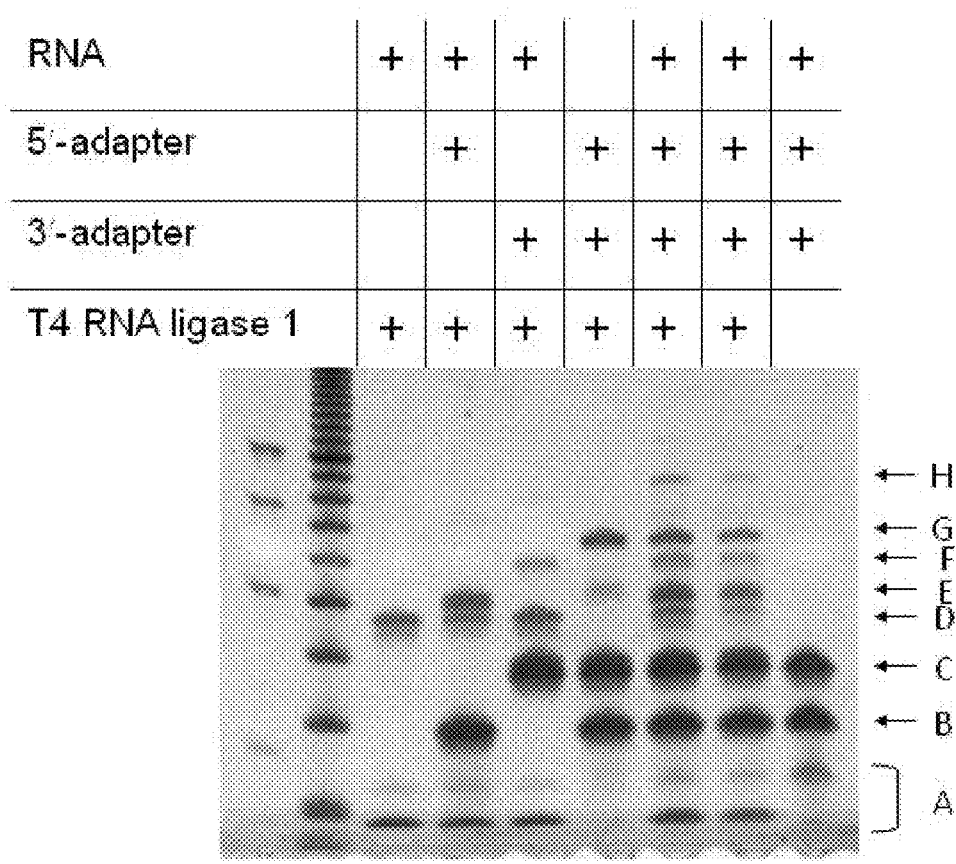
FIG. 19 is a polyacrylamide gel electrophoresis image showing ligation yields for RNA library preparation using modified 5'- and 3'-adapters and T4 RNA ligase 1.

Next, the modified 5'- and 3'-adapter probe pairs that suppress adapter probe dimer formation are combined with a single 5'-phosphorylated synthetic RNA sequence. In these experiments, each of the modified 5'- and 3'-adapter probe pairs are added into a reaction with a synthetic 5'-phosphorylated RNA and T4 RNA ligase I and suppression of adapter dimers and efficiency of ligation to the RNA assessed (FIG. 19).

Figure 20:
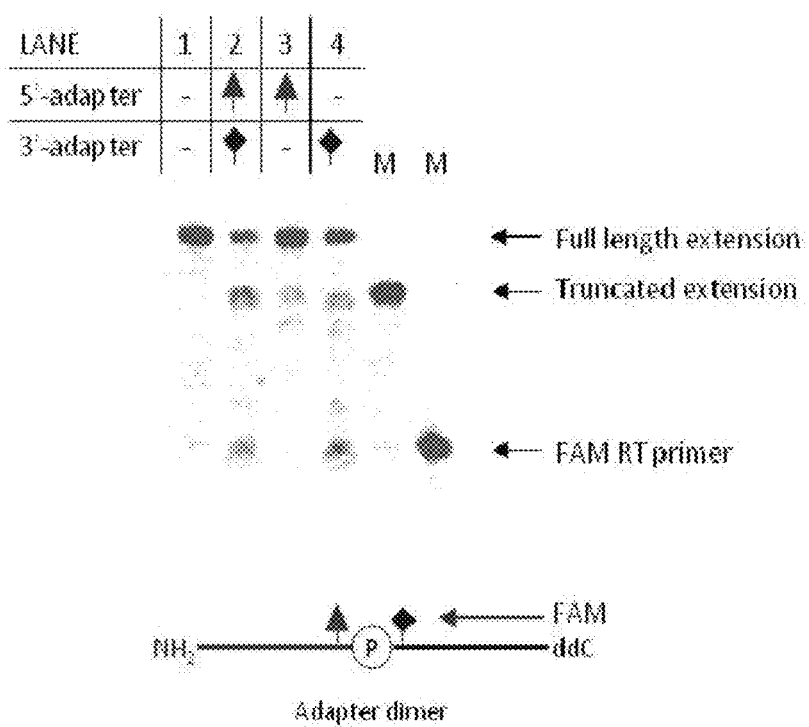
FIG. 20 is a polyacrylamide gel electrophoresis image showing reverse transcriptase activity for RNA library preparation using adapter dimers with 5' and 3' modifications.

Next, an assay for determining the efficiency of ligation of adapter probes onto the library and the suppression of adapter dimer formation is developed (FIG. 20). Reactions contain T4 RNA Ligase 1, 1 mM ATP; unmodified 5'- and 3'-adapter probe pairs, synthetic let-7d miRNA, 10% PEG 8000 and were incubated at 16° C. The resultant sample was analyzed on denaturing polyacrylamide gel stained with SYBR Gold nucleic acid stain. In this experiment, each of the components is systematically added into the reaction to deduce which ligation products were forming. Ligation products to form adapter dimer and adapter-tagged library are evident. Using this reaction set-up as a starting point, modified versions of the adapter probes can be tested for suppression of adapter dimer formation and for efficient tagged library formation.

The ligation products from the previous step are tested using a cDNA synthesis step to ensure that the modifications do not cause termination. In these experiments, a short DNA primer which is complementary to the 3'-end of the 3'-adapter probe is annealed and extended along the resultant ligation product using M-MLV reverse transcriptase, with analysis of the cDNA synthesis product by denaturing polyacrylamide gel electrophoresis (PAGE) analysis (FIG. 21). Ideal modified adapter probe pair(s) are those that suppress adapter probe dimer formation and produce abundant full-length product. In addition, the efficiency of the two adjacent modifications in a modified adapter probe dimer is assessed to determine their ability to block reverse transcription of the dimer.

The methods of the present invention may also be used to prepare tagged RNA libraries. The 5'-phosphorylated synthetic RNA library is designed to have a fixed length and sequence (~20 nucleotides) with three nucleotides of randomized sequence (equimolar ratio of A:C:G:U) at the 5'- and 3'-ends of the RNA. Next, the modified 3'- and 5'-adapter probe pair(s) are used to tag the RNA library using the workflow in FIG. 11. For comparison, a library is also prepared using the traditional protocol depicted in FIG. 9. After the modified adapter probes are ligated onto the library, a cDNA copy is generated by extension of a DNA primer along the library using reverse transcriptase. The cDNA synthesis product(s) is then amplified by emulsion PCR to maintain the abundance of the library components. The resultant amplicons are cloned into a vector and transformed into *E. coli* to isolate individual colonies. The plasmids are isolated from individually picked colonies and submitted for Sanger dideoxy sequencing. A statistically significant number of sequences are analyzed for suppression of adapter probe dimerization, the degree of concatamerization of the RNA library and maintenance of the composition of the input library.

Another aspect of the present invention provides methods for preparing libraries from small RNAs. Small RNAs are typically between 20 and 30 nucleotides in length and include classes such as microRNAs (miRNAs), small interfering RNAs (siRNAs) and Piwi interacting RNAs (piRNAs). Ligation-based approaches for small RNA library preparation using T4 RNA ligase 1 have demonstrated sequence biases for efficient ligation at the 5' (C>U≥A>G) and 3'-ends (A>G~C>U) of the small RNA sample. In addition, sample preparation workflows for small RNA deep sequencing (smRNA-Seq) cannot include a size enrichment step such as AMPure to remove unligated adapters and adapter dimers from the adapter-tagged library due their similarity in size. As a result, a gel purification step is commonly used to enrich the adapter-tagged library.

The limitation in smRNA-Seq workflows imparted by the need for a gel purification step is further evidenced by the recent description of two miRNA library prep approaches to suppress adapter dimer formation. In the first approach, adapter dimer formation is suppressed by hybridization of the cDNA synthesis primer after ligation of the 3'-adapter and before the 5'-adapter ligation step. This hybridization step creates a duplex with the 3'-adapter that suppresses ligation to form adapter dimers. While successful, this approach adds an additional step to the workflow, which increases the time for library preparation. Furthermore, this method may be further complicated should more than one cDNA synthesis primer be needed, as is the case for barcoding. In the second approach, a LNA sequence, which is complementary to the adapter dimer, is hybridized after the ligation steps to block cDNA primer extension by reverse transcriptase. This approach adds an additional sequence to the workflow, which adds expense because of the modifications. As was the case for the hybridization approach, the LNA-based workflow will be further complicated in the event that bar coded adapters are utilized. The modified adapter probes of the present invention, applied to small RNA sample preparations, block the formation of adapter dimers while allowing for efficient formation of adapter tagged libraries, without the need for a hybridization step.

In another aspect of the present invention, sense and antisense modified adapter probes are provided that suppress adapter:adapter ligation using the DNA library workflow. These probes contain a single modification to both the sense and antisense strands of the adapter probe, where modifications include 2'-fluoro- and 2'-methoxy sugar modifications and backbone modifications such as phosphorothioate and methylphosphonate. Hairpin versions of the modified P1 adapter probe are used to ensure that the sense and antisense strands are equimolar in concentration. In one experiment, only the P1 version of the modified hairpin adapter probe is used in order to simplify interpretation of the effect of the modification(s) on adapter dimer formation. Each of the modified hairpin adapter probes is ligated in the presence and absence of a synthetic ~40 base pairs 5'-phosphorylated dsDNA sequence using T4 DNA ligase and ranked for (a) suppression of adapter probe dimer formation and for (b) efficient ligation to a synthetic 5'-phosphorylated dsDNA sequence.

Once the modified hairpin adapter probes are selected, the corresponding modified P1 and P2 adapter probes are synthesized. The modified P1 and P2 adapter probes are compared with the unmodified probe constructs for suppression of adapter probe dimer and efficient tagged library formation using the same synthetic 5'-phosphorylated dsDNA sequence tested with the modified hairpin probes. The resultant tagged libraries are used as templates for a primer extension reaction using Taq DNA polymerase to ensure that the modifications of the P1 and P2 adapter probes do not block downstream replication.

A synthetic 5'-phosphorylated dsDNA library is prepared to confirm that the modified P1 and P2 adapter probes may be used to prepare adapter tagged dsDNA libraries. The 5'-phosphorylated synthetic dsDNA library is designed to have a fixed length and sequence (~40 base pairs) with one or two nucleotides of randomized sequence (equimolar ratio of A:C:G:T) at the 5'- and 3'-ends of the DNA. The lead modified P1 and P2 adapter probe constructs are used to tag the dsDNA library using the workflow in FIG. 13. For comparison, a library is also prepared using the traditional protocol depicted in FIG. 12. The adapter tagged library is then amplified by emulsion PCR to maintain the relative abundance of the library components, cloned into a vector and transformed into E. coli to isolate individual colonies. The plasmids are isolated from individually picked colonies and submitted for Sanger dideoxy sequencing. A statistically significant number of sequences are analyzed for suppression of modified adapter probe dimerization, the degree of concatamerization of the DNA library and maintenance of the composition of the input library.

The methods and compositions provided herein will now be described in greater detail by reference to the following non-limiting examples.

EXAMPLE 1

Detection of Ligation Yield Using PAGE Analysis

Figure 2:
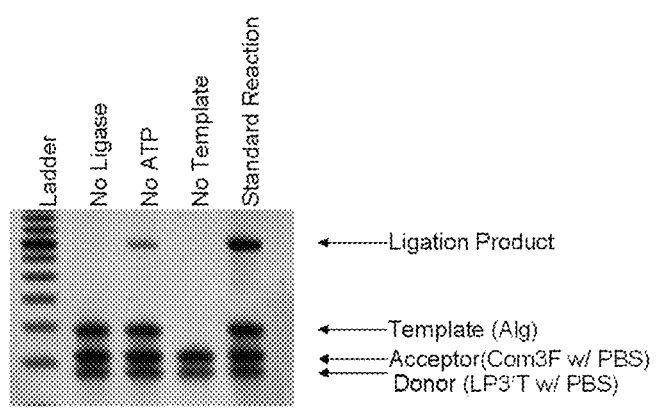
FIG. 2 shows PAGE gel results of ligation reactions in the absence of ligase (lane 2), in the absence of ATP (lane 3), in the absence of nucleic acid template (lane 4), and a positive control (donor, acceptor, ATP cofactor, ligase, and template) (lane 5).

Donors and acceptors (LP3'T Acceptor w/PBS and Com3F Donor w/PBS, respectively) with primer binding sequences ("PBS") were assessed for their ability to be joined by T4 DNA ligase in the presence of complementary template (Alg Template). Four experimental set-ups were performed (FIG. 2). A first ligation reaction mixture was set up that included donor, acceptor, ATP cofactor, template and no ligase. No ligation was detected. A second ligation reaction mixture was set up that included donor, acceptor, ATP cofactor, ligase, and no template. No ligation was detected. A third ligation reaction mixture was set up that included donor, acceptor, ligase, template, and no additional ATP cofactor was added. A small amount of ligation product was detected, which is likely due to a small amount of adenylated ligase that was isolated during the purification process. A fourth ligation reaction mixture was set up that included donor, acceptor, ATP cofactor, ligase, and template. A majority of the donor and acceptor were consumed, with efficient conversion to the joined ligation product.

Each 20 μL reaction was performed in buffer containing 50 mM Tris-HCl (pH 7.5), 10 mM $MgCl_2$, 10 mM dithiothreitol, 25 μg/ml bovine serum albumin. 1 mM ATP was added to the buffer separately. The donor (LP3'T w/PBS), acceptor (Com3F w/PBS), and template (Alg) were at 0.1 μM equimolar amounts. The acceptor, donor, and template were denatured at 95° C. for 3 minutes and annealed at 4° C. for 3 minutes. Ligation was initiated by adding 400 units of T4 ligase (New England Biolabs) to each reaction. Ligation proceeded at 16° C. for 20 minutes. Ligation was terminated by heating the reaction to 65° C. for 10 minutes and adding an equal volume of 2×TBE-Urea buffer (Invitrogen). Samples were run on 6% TBE-Urea Novex gels (Invitrogen). The gels were stained with SYBR Gold nucleic acid stain (Invitrogen) according to manufacturer's protocol.

TABLE 1

Donor and Acceptor Polynucleotide Sequences.

| Sequence Name | Sequence (5' → 3') |
|---|---|
| LP3'T For | TAGCGTCTTGATAGTCTCGTG (SEQ ID NO: 1) |
| Com3F Rev | GTACCAGTCGCCTAGAATACT (SEQ ID NO: 2) |
| LP3'T Acceptor w/PBS | <u>TAGCGTCTTGATAGTCTCGTG</u>CCCTGTTCCAGC GTCGGTGTTGCGTT (SEQ ID NO: 3) |
| LP3'G Acceptor w/PBS | <u>TAGCGTCTTGATAGTCTCGTG</u>CCCTGTTCCAGC GTCGGTGTTGCGTG (SEQ ID NO: 4) |
| LP3'C Acceptor w/PBS | <u>TAGCGTCTTGATAGTCTCGTG</u>CCCTGTTCCAGC GTCGGTGTTGCGTC (SEQ ID NO: 5) |
| LP3'A Acceptor w/PBS | <u>TAGCGTCTTGATAGTCTCGTG</u>CCCTGTTCCAGC GTCGGTGTTGCGTA (SEQ ID NO: 6) |
| Com3F Donor w/PBS | AGTTGTCATAGTTTGATCCTCTAGTCTGGG<u>AGT ATTCTAGGCGACTGGTAC</u> (SEQ ID NO: 7) |
| Alg Template | CCCAGACTAGAGGATCAAACTATGACAACTAAC GCAACACCGCAGACGCTGGAACAGGG (SEQ ID NO: 8) |

* The underlined portion represents the primer binding sequence (PBS).

EXAMPLE 2

Detection of Ligation Yield Using Real-Time PCR Analysis

Figure 3B:
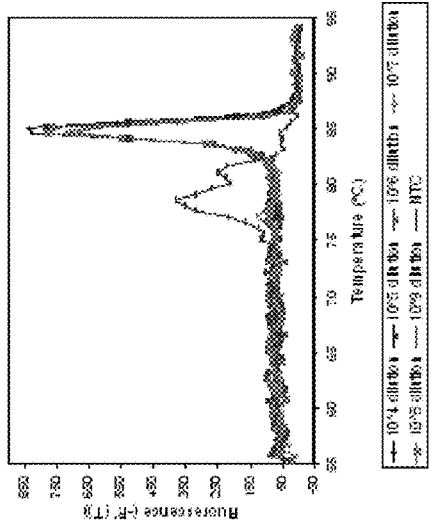
FIGS. 3A-3C shows results of a Real-time PCR experiment to detect ligation product.
Figure 3C:
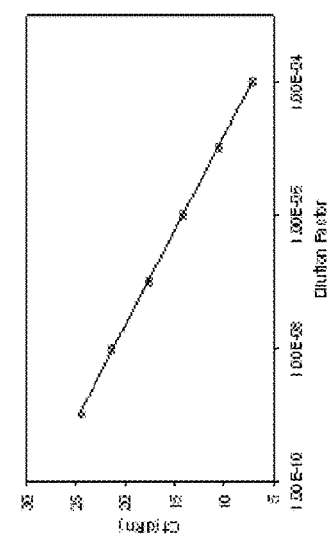
Figure 3A:
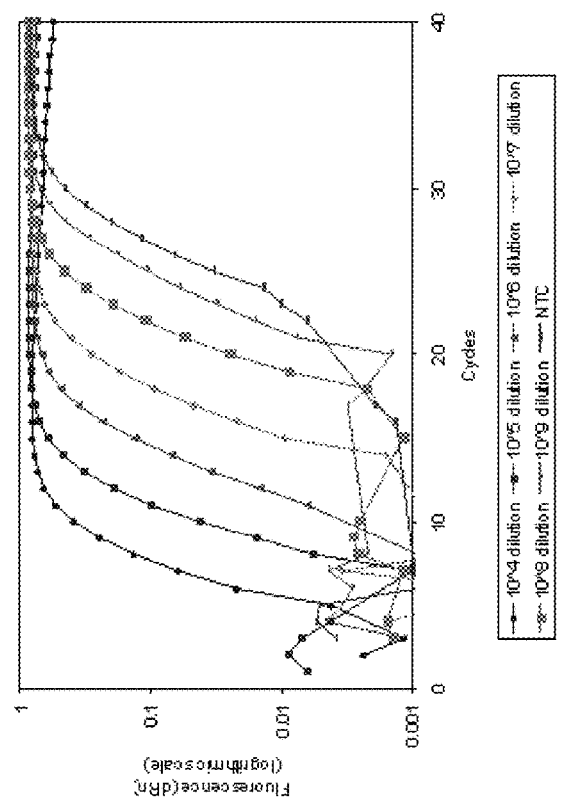

Ligation product between donor and acceptor polynucleotides (LP3'T Acceptor w/PBS and Com3F Donor w/PBS, respectively) was detected using real-time quantitative PCR. The ligation reactions were conducted with T4 DNA ligase in the presence of complementary template (Alg Template) and detected using real-time PCR. Serial dilutions of product from the ligation reactions ($10^4$ to $10^9$ dilutions of the ligation product) were used as template in subsequent PCR reactions. Reaction mixture consisted of 1×PCR buffer (20 mM Tris (pH 8.4), 50 mM KCl, 1.5 mM $MgCl_2$), PCR primers specific to primer binding sites designed at the 5'-end of the acceptor (LP3'T For) and 3'-end of the donor (Com3F Rev) (0.1 µM each), Taq DNA polymerase (5 U/ul) (Invitrogen), a SYBR Green I nucleic acid dye (1:60,000 dilution) (Invitrogen), a ROX reference dye (1:30,000 dilution) (Stratagene) in a 25 µl reaction. Thermocycling conditions were 95° C. for 10 minutes initial denaturation, followed by 40 cycles of 95° C. for 40 seconds, 56° C. for 30 seconds, 72° C. for 1 minute, and ending with a final extension step of 72° C. for 7 minutes. Reactions were performed in a Stratagene M×3005P® QPCR System instrument. As can be seen from FIG. 3, each of the six dilutions were detected using amplification plots (FIG. 3A), with the NTC (ligation performed in the absence of template) having an amplification curve with a significantly delayed Ct. The dissociation curve (FIG. 3B) revealed that all ligations performed in the presence of template had the same melting temperature, with the NTC having a lower melting temperature, which is likely due to extension of the Com 3F Rev along Com3F Donor w/PBS. Finally, the Ct values were extracted from the standard curve, and all dilutions of the ligation reaction could be detected with good linearity (FIG. 3C). Due to its ability to quantify nucleic acid target this assay will be of high importance to tease out subtle differences in the efficacy of a modified ligation component, in this instance, a modified ligase cofactor.

EXAMPLE 3

Figure 4:
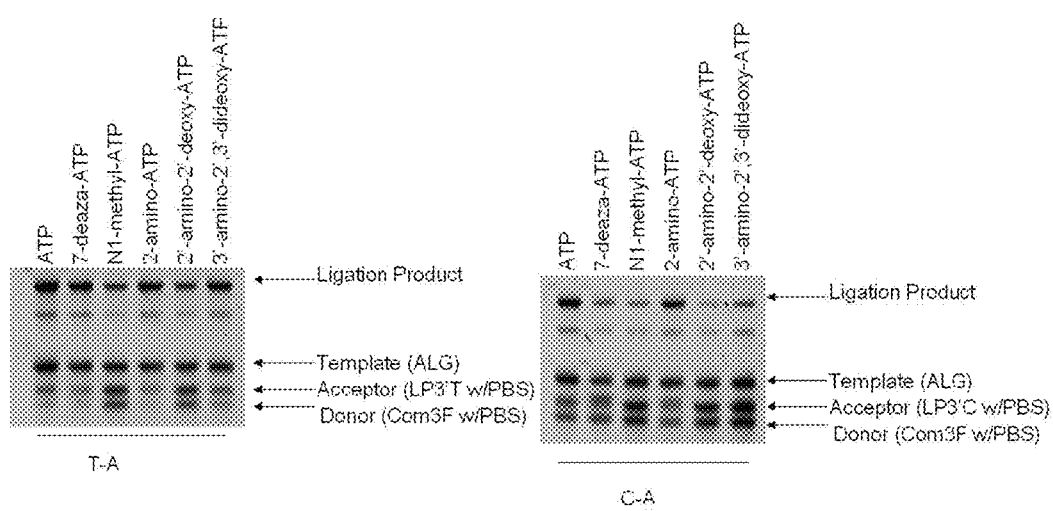
FIG. 4 shows PAGE gel results from ligation reactions with the following modified cofactors: 7-deaza-ATP, N1-methyl-ATP, 2-amino-ATP, 2'-amino-2'-deoxy-ATP, 3'-amino-2',3'-dideoxy-ATP compared to ligation reactions using ATP with matched (T-A) and mismatched (C-A) base pairs at the 3'-end of the acceptor strand.

Evaluating Discrimination of Modified Cofactors Between Matched and Mismatched Templates Using PAGE Analysis ATP analogs were compared to the corresponding natural ATP cofactor for their ability to join matched and mismatched templates (FIG. 4). ATP analogs were evaluated for relative ligation yield in the presence of matched template (LP3'T Acceptor w/PBS and Alg template; T-A matched base pair at the 3'-end of the acceptor strand) to the relative yield when a mismatched template was used (LP3'C Acceptor w/PBS and Alg template; C-A mismatched base pair on 3'-end of the acceptor strand). Reactions were performed as described for Example 1, with a cofactor of interest included in the reaction at 1 mM concentration. Natural ATP substrate was compared to the following modified cofactors: 7-deaza-ATP (7-deaza-adenosine-5'-triphosphate), N1-methyl-ATP (N1-methyl-adenosine-5'-triphosphate), 2-amino-ATP (2-amino-adenosine-5'-triphosphate), 2'-amino-2'-deoxy-ATP (2'-amino-2'-deoxyadenosine-5'-triphosphate), 3'-amino-2',3'-dideoxy-ATP (3'-amino-2',3'-dideoxy-adenosine-5'-triphosphate) (FIG. 4). All modified cofactors supported ligation with similar efficiency to natural ATP when a matched template was employed. However, when a mismatched template was employed, the use of modified cofactors resulted in a significant decrease in ligation yield when compared to the natural ATP.

EXAMPLE 4

Determination of Specificity Number

One method of determining the ligation yield of a ligation component of interest (e.g., modified ligase cofactors, modified donors or modified acceptors) is by assigning a specificity number. Specificity numbers can be determined for example, by dividing the ligation yield of a matched case by the ligation yield of a mismatched case where a single base pair differs relative to the matched case. Ligation yields are first determined by densitometry readings of the PAGE gels as demonstrated in Example 1. The yields are then normalized to the template readings in the same reaction, with subsequent normalization to the ligation yield for a reaction including the natural (ATP) cofactor, where ATP has a normalized yield of 1.0. For example, in the case of 2'-deoxy-ATP (2'-deoxy-adenosine-5'-triphosphate; FIG. 4), the ligation yield in the matched case (LP3'T Acceptor w/PBS and Alg template; T-A matched base pair on 3' end of the acceptor strand) was 1.34. In the mismatched case (LP3'C Acceptor w/PBS and Alg template; C-A mismatched base pair on 3' end of the acceptor strand) the ligation yield was 0.18. Accordingly, the specificity number assigned to 2'-deoxy-ATP in a C-A mismatch case was 1.34÷0.18 or 7.44. A value greater than one is indicative of improved ligation specificity. A value less than one is indicative of reduced ligation specificity.

EXAMPLE 5

Figure 5:
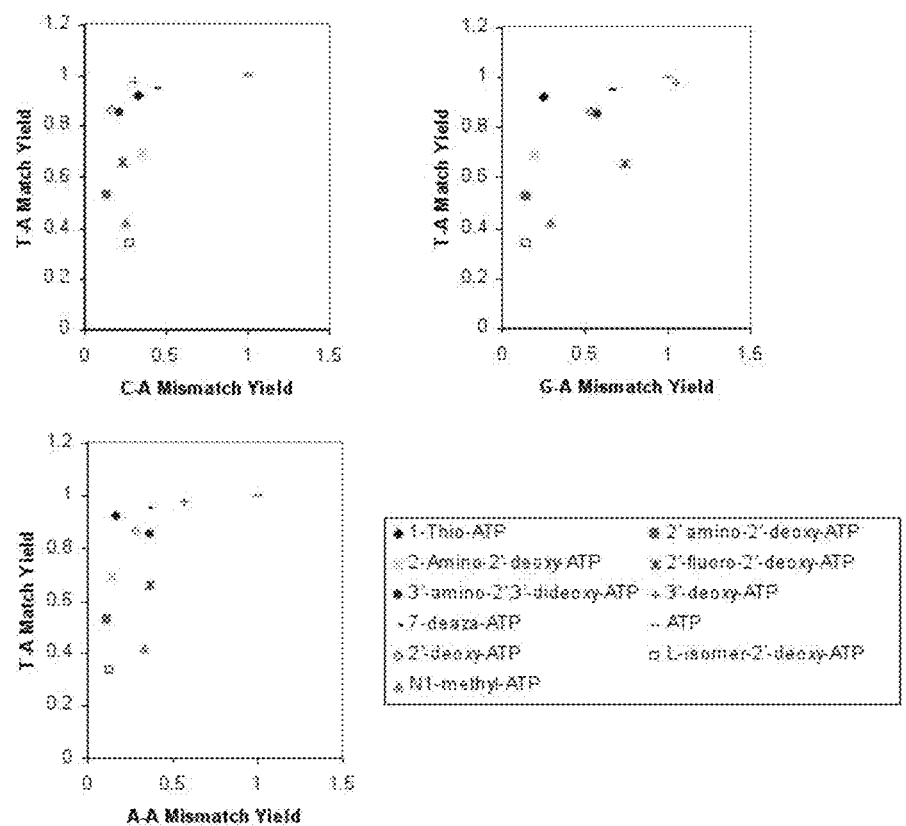
FIG. 5 is a series of scatter plots evaluating 10 modified ATP cofactors for relative ligation yield in the presence of a matched base pair at the 3'-end of the acceptor strand (T-A) to the relative yield with three different templates mismatched base pairs at the 3'-end of the acceptor strand (C-A, G-A and A-A). Preferably, a modified cofactor with improved specificity relative to an unmodified cofactor has similar ligation yield to a T-A match (value close to 1 on the y-axis) and mismatch ligation yield (C-A, G-A, and A-A) close to zero on the x-axis.

Matrix Evaluation to Identify Discrimination of Modified Cofactor Between Matched and Mismatched Templates ATP analogs were compared to the natural ATP cofactor for their ability to join matched and mismatched templates for relative ligation yield in the presence of matched template (LP3'T Acceptor w/PBS and Alg template; T-A matched base pair on 3'-end of the acceptor strand) relative to the yield of templates which contained a mismatched base pair on 3'-end of the acceptor: 1) LP3'C Acceptor w/PBS and Alg template; C-A mismatch, 2) LP3'G Acceptor w/PBS and Alg template; G-A mismatch, and 3) LP3'A Acceptor w/PBS and Alg template; A-A mismatch (FIG. 5). Reactions were performed as described for Example 1, with a cofactor of interest included in the reaction at 1 mM concentration. Natural ATP cofactor was compared to the following ten modified cofactors: 5'-alpha-thio-adenosine-5'-triphosphate (1-thio-ATP), 2' amino-2'-deoxy-adenosine-5'-triphosphate (2'-amino-2'-deoxy-ATP), 2-Amino-2'-deoxy-adenosine-5'-triphosphate (2-amino-2'-deoxy-ATP), 2'-fluoro-2'-deoxy-adenosine-5'-triphosphate (2'-fluoro-2'-deoxy-ATP), 3'-amino-2',3'-dideoxy-adenosine-5'-triphosphate (3'-amino-2',3'-dideoxy-ATP), 3'-deoxy-adenosine-5'-triphosphate (3'-deoxy-ATP), 7-deaza-adenosine-5'-triphosphate (7-deaza-ATP), 2'-deoxy-adenosine-5'-triphosphate (2'-deoxy-ATP), L-isomer-2'-deoxy-adenosine-5'-triphosphate (L-isomer of 2'-deoxy-ATP), and N1-methyl-adenosine-5'-triphosphate (N1-methyl-ATP). The results of the integration from PAGE analysis of ligation yields for the four different base pairs of interest: T-A, G-A, C-A, and A-A, were plotted in a series of three scatter plots. Each scatter plot compares the normalized yield for a matched template (T-A) to the normalized yield for each of the three different mismatched templates (C-A, G-A, and A-A) (FIG. 5). Lead modifications of interest will have a comparable ligation yield to natural ATP in the matched case (T-A), with a low ligation yield in the presence of a mismatched template (C-A, G-A, and A-A). From this panel of analogs, 5'-alpha-thio-adenosine-5'-triphosphate, 2'-deoxy-adenosine-5'-triphosphate, and 3'-amino-2',3'-dideoxy-adenosine-5'-triphosphate were identified as lead modifications of interest.

EXAMPLE 6

Matrix Evaluation to Identify Discrimination of a Modified Acceptor Between Matched and Mismatched Templates Various sugar and backbone modified acceptor strands were compared to the natural unmodified acceptor strand for their ability to join matched and mismatched templates. The modified acceptor strands were evaluated for relative ligation yield in the presence of matched template (LP3'T Acceptor w/PBS and Alg template; T-A matched base pair on 3' end of the acceptor) relative to the yield of templates which contained a mismatched base pair at the 3'-end of the template: 1) LP3'T Acceptor w/PBS and Glg template; T-G mismatch, 2) LP3'T Acceptor w/PBS and Clg template; T-C mismatch, and 3) LP3'T Acceptor w/PBS and Tlg template; T-T mismatch. Reactions were performed as described for Example 1 using T4 DNA ligase and with the acceptor strand of interest included in the reaction at 1 µM concentration. Further experiments were performed with *E. coli* ligase, a NAD dependent ligase (not shown) in which the performance of the natural acceptor strand was compared to ten modified acceptors having the formula as shown below:

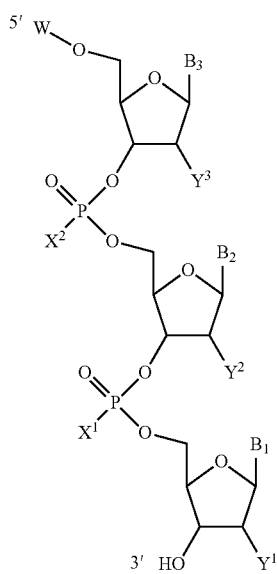

wherein:
$X^1$ and $X^2$ are each independently selected from the group consisting of OH, SH, and $CH_3$, and
$Y^1$, $Y^2$, and $Y^3$ are each independently selected from the group consisting of H, F and $OCH_3$; and
W is an oligonucleotidyl residue.

Figure 6:
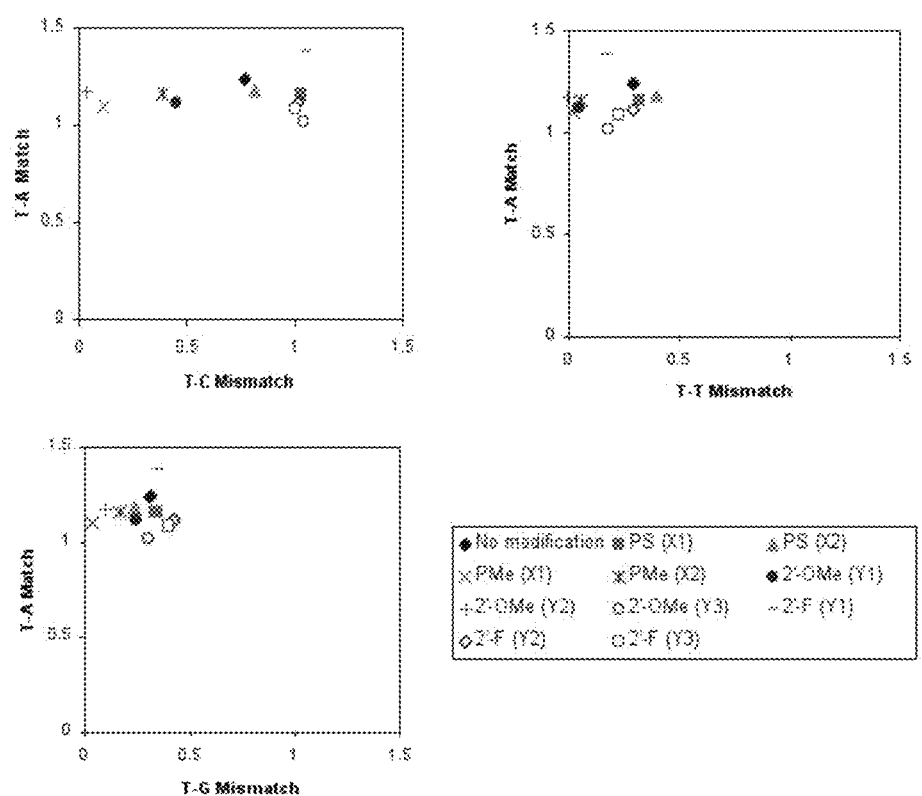
FIG. 6 is a series of scatter plots evaluating modified acceptors for relative ligation yield in the presence of matched base pair at the 3'-end of the acceptor strand (T-A) to the relative yield with three different mismatched base pairs at the 3'-end of the acceptor strand (T-G, T-C and T-T), as described in Example 1. Modified acceptors studied contained a single substitution group: PS (X1) indicates S at the X$^1$ position, PS (X2) indicates S at the X$^2$ position, PMe (X1) indicates Me at the X$^1$ position, PMe (X2) indicates Me at the X$^2$ position, 2'-OMe (Y1) indicates OCH$_3$ at the Y$^1$ position, 2'-OMe (Y2) indicates OCH$_3$ at the Y$^2$ position, 2'-OMe (Y3) indicates OCH$_3$ at the Y$^3$ position, 2'-F (Y1) indicates F at the Y$^1$ position, 2'-F (Y2) indicates F at the Y$^2$ position, and 2'-F (Y3) indicates F at the Y$^3$ position, as defined in Formula II. Preferably, a candidate modified acceptor with improved specificity relative to an unmodified acceptor will have similar ligation yield to a T-A match (value near 1 on the y-axis) and mismatch ligation yield (C-A, G-A, and A-A) close to zero on the x-axis.

In the natural acceptor, $X^1$ and $X^2$ are OH and $Y^1$, $Y^2$, and $Y^3$ are H (FIG. 6, No modification). Each of the ten modified acceptors has a modification at one of sites $X^1$, $X^2$, $Y^1$, $Y^2$, or $Y^3$ relative to the natural acceptor such that $X^1$ is SH or $CH_3$ (FIG. 6, PS (X1) and PMe (X1), respectively), $X^2$ is SH or $CH_3$ (FIG. 6, PS (X2) and PMe (X2), respectively), $Y^1$ is F or $OCH_3$ (FIG. 6, 2'-F (Y1) or 2'-OMe (Y1), respectively), $Y^2$ is F or $OCH_3$ (FIG. 6, 2'-F (Y2) or 2'-OMe (Y2), respectively), and $Y^3$ is F or $OCH_3$ (FIG. 6, 2'-F (Y3) or 2'-OMe (Y3), respectively).

Ligation yields, determined from PAGE gel analysis, for the four different base pairs of interest: T-A, T-G, T-C, and T-T, were plotted in a series of three scatter plots. Each scatter plot compared the normalized yield for a matched template (T-A) to the normalized yield each of the three different mismatched templates (T-G, T-C, and T-T) (FIG. 6). Lead modifications of interest will have a comparable ligation yield to ATP in the matched case (T-A), with a low ligation yield in the presence of a mismatched template (T-G, T-C, and T-T). From this panel modified acceptors, $CH_3$ modification at the $X^1$ position (FIG. 6, PMe (X1)) and $OCH_3$ modification at the $Y^2$ position (FIG. 6, 2'-OMe (Y2)) were identified as the lead acceptor modifications of interest.

EXAMPLE 7

Matrix Evaluation to Identify Discrimination of a Modified Donor Between Matched and Mismatched Templates Various sugar and backbone modified donor strands were compared to the natural donor strand for their ability to join matched and mismatched templates. The modified donor strands were evaluated for relative ligation yield in the presence of matched template (Com3F Donor w/PBS, LP3'T Acceptor w/PBS and Alg template; T-A matched base pair on 3' end of the acceptor strand) relative to the yield of templates which contain a mismatched base pair at 3'-end of the template: 1) Com3F Donor w/PBS, LP3'T Acceptor w/PBS, and Clg template; T-C mismatch and 2) Com3F w/PBS, LP3'C w/PBS, and Alg; C-A mismatch. Reactions were performed as described for Example 1 with T4 DNA ligase and the donor strand of interest included into each reaction at 1 µM concentration. Further experiments were performed with *E. coli* ligase, a NAD dependent ligase (not shown). Natural donor strand was compared to the following five modified donors:

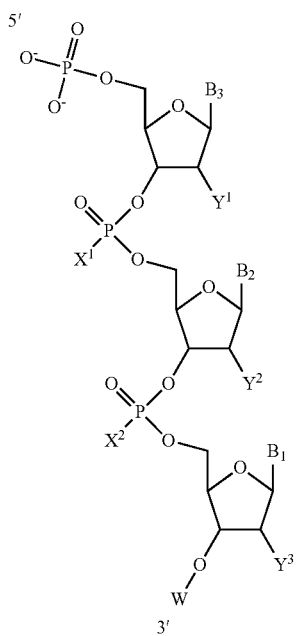

where $X^1$ and $X^2$ are each substituted separately with OH or $CH_3$, and $Y^1$, $Y^2$, and $Y^3$ are each substituted separately with H or $OCH_3$.

Figure 7:
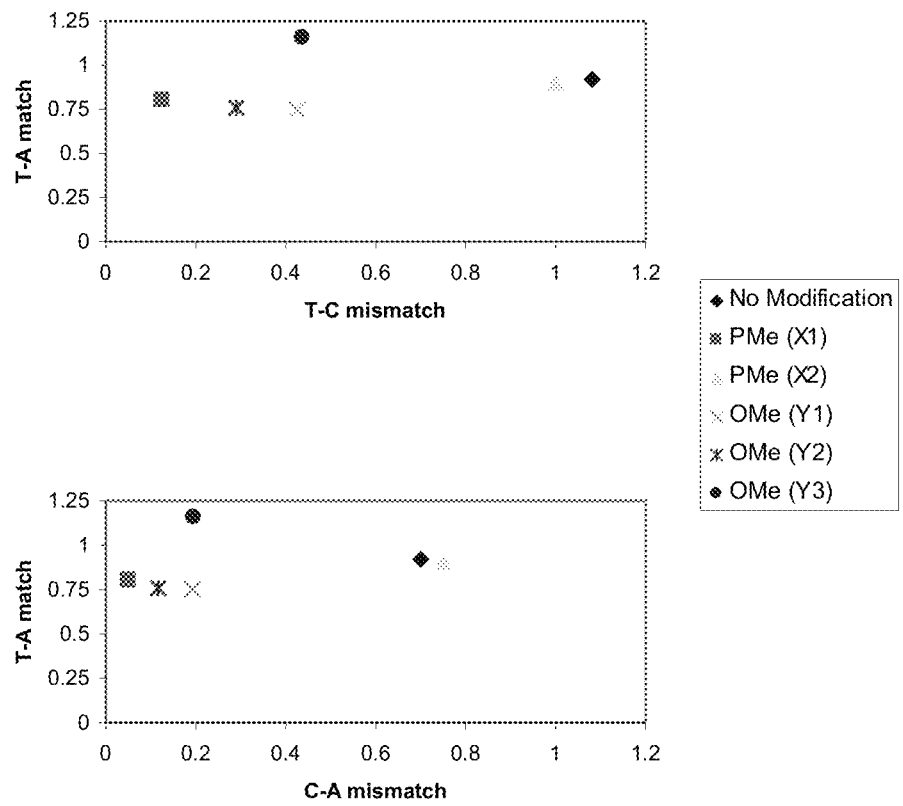
FIG. 7 is a series of scatter plots evaluating modified donors for relative ligation yield in the presence of matched base pair at the 3'-end of the acceptor strand (T-A) to the relative yield with two different mismatched base pairs at the 3'-end of the acceptor strand (T-C, and C-A), as described in Example 1. Modified donors contained a single substitution group: PMe (X1) indicates Me at the X$^1$ position, PMe (X2) indicates Me at the X$^2$ position, 2'-OMe (Y1) indicates OCH$_3$ at the Y$^1$ position, 2'-OMe (Y2) indicates OCH$_3$ at the Y$^2$ position, and 2'-OMe (Y3) indicates OCH$_3$ at the Y$^3$ position, as defined in Formula III. Preferably, a modified donor with improved specificity relative to an unmodified donor has similar ligation yield to a T-A match (value near 1 on the y-axis) and mismatch ligation yield (C-A, G-A, and A-A) close to zero on the x-axis.

In the natural donor, $X^1$ and $X^2$ are OH and $Y^1$, $Y^2$, and $Y^3$ are H (FIG. 7, No modification). Each of the five modified donors has a modification at one of sites $X^1$, $X^2$, $Y^1$, $Y^2$, or $Y^3$ relative to the natural donor such that $X^1$ is $CH_3$ (FIG. 7, PMe (X1)), $X^2$ is $CH_3$ (FIG. 7, PMe (X2)), $Y^1$ is $OCH_3$ (FIG. 7, 2'-OMe (Y1)), $Y^2$ is $OCH_3$ (FIG. 7, 2'-OMe (Y2)), or $Y^3$ is $OCH_3$ (FIG. 7, 2'-OMe (Y3)).

Normalized ligation yields determined from PAGE gel analysis for the three different base pairs of interest: T-A, T-C, and C-A, were plotted in a series of three scatter plots. Each scatter plot compared a matched template (T-A) to each of the three different mismatched templates (T-C, and C-A) (FIG. 7). Lead modifications of interest will have a comparable ligation yield to ATP in the matched case (T-A), with a low ligation yield in the presence of a mismatch (T-C and C-A). From this panel modified acceptors, $CH_3$ modification at the $X^1$ (PMe $X^1$) and $X^2$ (PMe $X^2$) positions were identified as the lead donor modifications of interest.

EXAMPLE 8

Evaluation to Identify a Modified Acceptor in Combination with a Modified ATP Cofactor that Best Discriminates Between Matched and Mismatched Templates Continuing upon the studies depicted in Examples 1, 3, 4, and 5, a number of sugar and backbone modified acceptor strands in combination with several modified ATP cofactors were compared to the natural acceptor strand and ATP for their ability to join upon matched versus mismatched templates. These studies evaluated the combination of modified acceptor strands with modified ATP cofactors for relative ligation yield in the presence of matched template (Com3F Donor w/PBS, LP3'T Acceptor w/PBS and Alg template; T-A matched base pair on 3' end of the acceptor strand) to the relative yield when a single template which contained a mismatched base pair on 3' end of the template strand was employed: 1) Com3F Donor w/PBS, LP3'T Acceptor w/PBS, and Clg template; T-C mismatch. Reactions were performed as described for Example 1 with the acceptor strand of interest included into each reaction at 1 µM concentration and the ATP cofactor at 1 mM concentration. In these studies, the performance of the natural acceptor strand was compared to the following five modified acceptors:

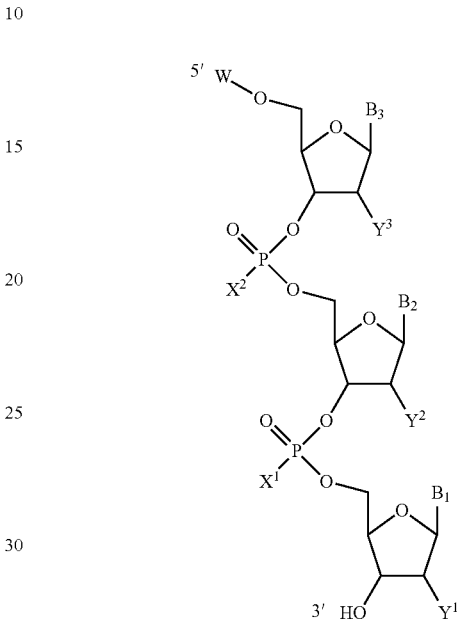

where $X^1$ is independently selected from the group consisting of OH, SH and $CH_3$, and $X^2$ is independently selected from the group consisting of OH and $CH_3$, and $Y^1$ and $Y^2$ are each independently selected from the group consisting of H and $OCH_3$.

In the natural acceptor (FIG. 8, No modification), $X^1$ and $X^2$ are OH and $Y^1$ and $Y^2$ are H. Each of the five modified acceptors has a modification at one of sites $X^1$, $X^2$, $Y^1$, or $Y^2$ relative to the natural acceptor such that $X^1$ is SH (FIG. 8, PS (X1)), $X^1$ is $CH_3$ (FIG. 8, PMe (X1)), $X^2$ is $CH_3$ (FIG. 8, PMe (X2)), $Y^1$ is $OCH_3$ (FIG. 8, 2'-OMe (Y1)) or $Y^2$ is $OCH_3$ (FIG. 8, 2'-OMe (Y2)).

These five modified acceptor strands were assayed in combination with six modified ATP analogs including: 2'-deoxy-ATP (2'-deoxy-adenosine-5'-triphosphate), 1-thio-ATP (5'-alpha-thio-adenosine-5'-triphosphate), 2'-amino-2'-deoxy-ATP (2'-deoxy-adenosine-5'-triphosphate), 2-amino-ATP (2-amino-adenosine-5'-triphosphate), 3'-amino-2',3'-dideoxy-ATP (3'-amino-2',3'-dideoxy-adenosine-5'-triphosphate), and 2-amino-2'-deoxy-ATP (2-amino-2'-deoxy-adenosine-5'-triphosphate). All possible combinations of ATP analogs and modified acceptor strands were tested.

Ligation yields (normalized to ATP), determined from PAGE gel analysis, for the two different base pairs of interest: T-A and T-C, were recorded in a chart (FIG. 8). The charts include the relative litagion yields using sugar and backbone modified acceptor strands in combination with different modified ATP cofactors. These values are relative to the ligation yields using natural acceptor strands and ATP with matched (T-A) and mismatched (T-C) base pairs at the 3'-end of the acceptor strand, as described in Example 1. In the matched case (T-A), values in dot-shaded cells represent greater than 0.85 relative ligation yield, values in unshaded cells represent 0.70-0.85 relative ligation yield, and values in gray-shaded cells represent 0-0.70 relative ligation yield. In the mismatched case (T-C), dot-shaded cells represent 0-0.01 relative ligation yield, unshaded cells represent 0.01-0.1 relative ligation yield, and gray cells represent 0.10-1.00 relative ligation yield. All presented yields were normalized to the combination of ATP with an unmodified acceptor strand. Combinations with preferred performance criteria have greater than 0.85 relative yield in the matched case (T-A) (e.g., dot-shaded cells in FIG. 8, top chart) and less than 0.01 relative ligation yield in the presence of a mismatched template (T-C) (e.g., dot-shaded cells in FIG. 8, bottom chart). From these possible combinations, a CH3 modification at the X1 position (FIG. 8, PMe (X1)) with 3'-amino-2',3'-dideoxy-ATP (3'-amino-2',3'-dideoxy-adenosine-5'-triphosphate) was identified as the lead modified cofactor and modified acceptor combination of interest, with a matched yield of 1.22 and a mismatched yield of 0.00.

EXAMPLE 9

Evaluation of Modified Probe Constructs for Suppression of Dimer Formation

The following modified adapter probes shown in the table below were prepared. These modified adapter probes were evaluated for their ability to suppress adapter probe dimer formation. Following the approach as outlined in FIG. 11, a series of modified 5'- and 3'-adapter probes were prepared and tested as substrates for T4 RNA ligase 1 in the absence of RNA. First, ten modified 5'-adapter probe constructs were tested in combination with unmodified versions of the 3'-adapter probe to identify modified probes that supported strong ligation yields. In parallel, ten modified 3'-adapter probe constructs were tested in combination with unmodified versions of the 3'-adapter probe. These data are summarized in FIG. 17. Most of the modified probes supported ligation with the corresponding unmodified probe, where modifications to the 5'-adapter probe had a greater effect on ligation yield.

| Probe Type | Name | Sequence (5'-3') |
|---|---|---|
| Acceptor | Unmodified | NH2-r(GUUCAGAGUUCUACAGUCCGACGAUC) (SEQ ID NO: 9) |
| | Phosphorothioate (n) | NH2-r(GUUCAGAGUUCUACAGUCCGACGAU(PS)C) (SEQ ID NO: 10) |
| | Phosphorothioate (n − 1) | NH2-r(GUUCAGAGUUCUACAGUCCGACGA(PS)UC) (SEQ ID NO: 11) |
| | Methylphosphonate (n) | NH2-r(GUUCAGAGUUCUACAGUCCGACGA)T(PMe)r(C) (SEQ ID NO: 12) |
| | Methylphosphonate (n − 1) | NH2-r(GUUCAGAGUUCUACAGUCCGACG)A(PMe)r(UC) (SEQ ID NO: 13) |
| | 2'-Methoxy (n) | NH2-r(GUUCAGAGUUCUACAGUCCGACGAUC(OMe)) (SEQ ID NO: 14) |
| | 2'-Methoxy (n − 1) | NH2-r(GUUCAGAGUUCUACAGUCCGACGAU(OMe)C) (SEQ ID NO: 15) |
| | 2'-Methoxy (n − 2) | NH2-r(GUUCAGAGUUCUACAGUCCGACGA(OMe)UC) (SEQ ID NO: 16) |
| | Fluoro (n) | NH2-r(GUUCAGAGUUCUACAGUCCGACGAUC(F)) (SEQ ID NO: 17) |
| | Fluoro (n − 1) | NH2-r(GUUCAGAGUUCUACAGUCCGACGAU(F)C) (SEQ ID NO: 18) |
| | Fluoro (n − 2) | NH2-r(GUUCAGAGUUCUACAGUCCGACGA(F)UC) (SEQ ID NO: 19) |
| Donor | Unmodified | P-AGTTGTCATAGTTTGATCCTCTAGTCTGGGAGTATTCTAGGCGACTGGTA-ddC (SEQ ID NO: 20) |
| | Phosphorothioate (n − 1) | P-A(PS)GTTGTCATAGTTTGATCCTCTAGTCTGGGAGTATTCTAGGCGACTGGTA-ddC (SEQ ID NO: 21) |
| | Phosphorothioate (n − 2) | P-AG(PS)TTGTCATAGTTTGATCCTCTAGTCTGGGAGTATTCTAGGCGACTGGTA-ddC (SEQ ID NO: 22) |
| | Methylphosphonate (n − 1) | P-A(PMe)GTTGTCATAGTTTGATCCTCTAGTCTGGGAGTATTCTAGGCGACTGGTA-ddC (SEQ ID NO: 23) |
| | Methylphosphonate (n − 2) | P-AG(PMe)TTGTCATAGTTTGATCCTCTAGTCTGGGAGTATTCTAGGCGACTGGTA-ddC (SEQ ID NO: 24) |
| | 2'-Methoxy (n) | P-A(OMe)GTTGTCATAGTTTGATCCTCTAGTCTGGGAGTATTCTAGGCGACTGGTA-ddC (SEQ ID NO: 25) |

| Probe Type | Name | Sequence (5'-3') |
|---|---|---|
| | 2'-Methoxy (n - 1) | P-AG(OMe)TTGTCATAGTTTGATCCTCTAGTCTGGGAGTA TTCTAGGCGACTGGTA-ddC (SEQ ID NO: 26) |
| | 2'-Methoxy (n - 2) | P-AGU(OMe)TGTCATAGTTTGATCCTCTAGTCTGGGAGTA TTCTAGGCGACTGGTA-ddC (SEQ ID NO: 27) |
| | 2'-Fluoro (n) | P-A(F)GTTGTCATAGTTTGATCCTCTAGTCTGGGAGTATT CTAGGCGACTGGTA-ddC (SEQ ID NO: 28) |
| | 2'-Fluoro (n - 1) | P-AG(F)TTGTCATAGTTTGATCCTCTAGTCTGGGAGTATT CTAGGCGACTGGTA-ddC (SEQ ID NO: 29) |
| | 2'-Fluoro (n - 2) | P-AGU(F)TGTCATAGTTTGATCCTCTAGTCTGGGAGTATT CTAGGCGACTGGTA-ddC (SEQ ID NO: 30) |

Figure 18:
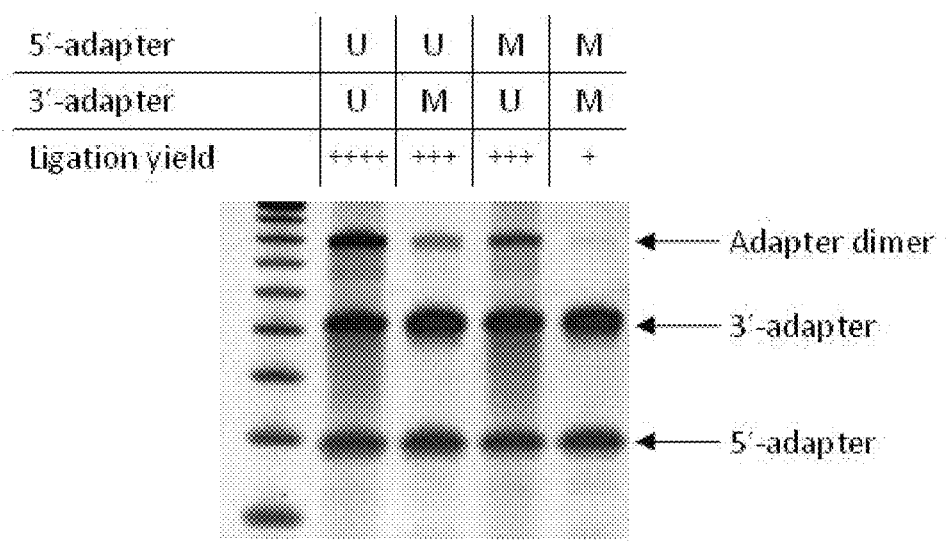
FIG. 18 is a polyacrylamide gel electrophoresis image showing ligation yields for adapter dimer suppression in a RNA library preparation workflow using modified 5'- and 3'-adapters and T4 RNA ligase 1.

Next, a pair of the modified 5'- and 3'-adapter probe constructs (2'-methoxy modified and methylphosphonate modified, respectively) that showed strong ligation yields with unmodified probes (FIG. 17) were tested for suppression of adapter probe dimer formation (FIG. 18). These modified adapter probes ligate efficiently to unmodified probes (+++) and suppressed adapter probe dimer yield significantly (+). These findings validate that modifications can be identified that are compatible with T4 RNA ligase I. Furthermore, this data suggests that similar types of modifications can be identified for use in dsDNA library preparation workflows with T4 DNA ligase.

EXAMPLE 10

Development of a One-Step Protocol for RNA Library Preparation

Next, an assay for determining the efficiency of ligation of adapter probes onto the library and the suppression of adapter dimer formation was developed (FIG. 19). Reactions contained 1×T4 RNA Ligase 1 Buffer (from New England Biolabs), 1 mM ATP; unmodified 5'- and 3'-adapter probe pairs (listed in Example 9; at 1 or 2 µM concentration), synthetic let-7d miRNA (5' P-CUAUACGACCUGCUGC-CUUUCU 3' (SEQ ID NO:57); 0.1 or 0.5 µM), 10% PEG 8000, and 20 U of T4 RNA Ligase 1 in a 10 µL reaction volume. The reaction mixture was incubated at 16° C. for 16 hours and quenched with an equal volume of TBE-urea gel loading buffer. The resultant sample was loaded on a 10% denaturing polyacrylamide gel and stained with SYBR Gold nucleic acid stain. The experiment was designed to systematically add each of the components into the reaction to deduce which ligation products were forming. Ligation products to form adapter dimer and adapter-tagged library were evident. Using this reaction set-up as a starting point, modified versions of the adapter probes can then be tested for suppression of adapter dimer formation and for efficient tagged library formation.

EXAMPLE 11

Evaluation of Modified Probe Constructs for Ability to Block Reverse Transcription The goal of these studies was to determine whether the presence of two consecutive modifications would block formation of full-length reverse transcription product along an adapter probe dimer. A FAM labeled reverse primer (5'-FAM-ATAGTCTCGTGCCCTGC-3' (SEQ ID NO:58)) was prepared and annealed to an adapter probe dimer ligation product from Example 9 and incubated in the presence of SuperScript III reverse transcriptase (FIG. 20). When the adapter probe dimer was unmodified (Lane 1), complete conversion to full-length extension was observed. When the adapter probe dimer was singly modified (Lanes 3 and 4), some indications of truncated extension were evident, but there was significant read-through to full-length extension. When the adapter probe dimer was double-modified (Lane 2), the majority of the extension products were truncated. This data helps to support the hypothesis that the presence of two adjacent modifications on adapter probe dimers can block reverse transcription, thereby further enriching the population of adapter-tagged libraries.

EXAMPLE 12

Comparison of Protocols for Preparing Small RNA Libraries with Modified Probe Constructs Versus Traditional Methods The small RNA library preparation protocol of the present invention is compared to the traditional small RNA library protocol utilizing a synthetic mock small RNA library that mimics the relative ratios of the ten miRNAs present in the liver at high, medium, and low expression levels is prepared (Table 2). The synthetic mock small RNA library is used as a template for library preparation using the optimized one step library workflow in comparison to TruSeq Small RNA Sample Preparation Kit (traditional protocol; Illumina, San Diego, Calif.). The resultant adapter tagged libraries are quantified using Real-time PCR to determine whether the relative abundances of the mock small RNA library are maintained between approaches. Next a human liver total RNA sample enriched for small RNA is used as a template for library preparation using the optimized one-step protocol and the traditional protocol. After the modified adapter probes are ligated onto the library, a cDNA copy is generated by reverse transcriptase extension, followed by PCR amplification. The resultant libraries are sequenced in a paired end read on a Hi-Seq System (Illumina, San Diego, Calif.). To avoid reported biases due to the use of barcodes, the tagged libraries generated from each approach are each sequenced in an independent lane on the instrument, with the sequencing run and data analysis being performed by GENEWIZ. The dataset yields sufficient data to count the relative abundances of each of the miRNA in the sample that allows for analysis of adapter probe dimer suppression, the degree of concatamerization of the RNA library, and maintenance of the composition of the input library from library preparation workflow to workflow.

TABLE 2 comparison to traditional small RNA library protocol utilizing a synthetic mock small RNA library that mimics the relative ratios of the ten miRNAs present in the liver at high, medium, and low expression levels.

| Name | miRNA sequence (5'-3') | Expression in Liver |
|---|---|---|
| Hsa-miR-122 | UGGAGUGUGACAAUGGUGUUUG (SEQ ID NO: 31) | 1006 |
| Hsa-miR-16-1 | CCAGUAUUAACUGUGCUGCUGA (SEQ ID NO: 32) | 47 |
| Hsa-miR-22 | AGUUCUUCAGUGGCAAGCUUUA (SEQ ID NO: 33) | 19 |
| Hsa-miR-143 | UGAGAUGAAGCACUGUAGCUC (SEQ ID NO: 34) | 15 |
| Hsa-miR-125b | ACGGGUUAGGCUCUUGGGAGCU (SEQ ID NO: 35) | 14 |
| Hsa-let-7b | CAACAAAUCACAGUCUGCCAUA (SEQ ID NO: 36) | 13 |
| Hsa-miR-99a | CAAGCUCGCUUCUAUGGGUCUG (SEQ ID NO: 37) | 12 |
| Hsa-let-7c | CAACAAAUCACAGUCUGCCAUA (SEQ ID NO: 38) | 7 |
| Hsa-miR-451a | AAACCGUUACCAUUACUGAGUU (SEQ ID NO: 39) | 6 |
| Hsa-miR-30d | UGUAAACAUCCCCGACUGGAAG (SEQ ID NO: 40) | 6 |

EXAMPLE 13

Evaluation of Modified Double Stranded Adapter Probes for Suppression of Adapter Dimer Formation In these studies the hypothesis that the use of a double stranded modified adapter probe constructs could be used to suppress adapter dimer formation in blunt ended library preparation schemes was tested. In these studies a number of sugar variants for the adapter probes were tested including 2'-fluoro and 2'-methoxy modified constructs (see table below). In addition to the sugar modifications, two variants of double stranded adapter probes were prepared—one with a 5'-phosphate and one with a 5'-adenylate. Double stranded adapter probes were formed by hybridization of a donor and acceptor probe. The double stranded modified adapter probe constructs (0.15 μM) were incubated in the presence 1× Reaction Buffer (50 mM Tris-HCl (pH 7.5), 10 mM MgCl$_2$, 10 mM DTT, 5% PEG 4000, and ATP (0.5 mM for 5'-phosorylated adapters and 0 mM 5'-adenylated adapters) in a reaction volume of 50 μL at 22° C. for 2 hour. The ligation product was analyzed by 10% native polyacrylamide gel electrophoresis. Results show that liagtions can occur with 5'-phoshorylated or 5'-adenylated adapters. Furthermore, results demonstrate suppression of adapter dimer formation for a number of the double stranded modified adapter probe constructs.

| Probe Type | Name | Sequence |
|---|---|---|
| Donor | Unmodified-P | P-AGT TGT CAT AGT TTG ATC CTC T-(C3 Propyl spacer) (SEQ ID NO: 41) |
| Donor | Unmodified-App | Adenylate-AGT TGT CAT AGT TTG ATC CTC T-(C3 Propyl spacer) (SEQ ID NO: 42) |
| Acceptor | Unmodified | NH2-TTTGTAGAGGATCAAACTATG ACAACT (SEQ ID NO: 43) |
| | 2'-Fl (n) | NH2-TTTGTAGAGGATCAAACTATG ACAAC (X = 2'Fluoro) (SEQ ID NO: 44) |
| | 2'-Fl (n − 1) | NH2-TTTGTAGAGGATCAAACTATG ACAAXT (X = 2'Fluoro) (SEQ ID NO: 45) |
| | 2'-Fl (n − 2) | NH2-TTTGTAGAGGATCAAACTATG ACAXCT (X = 2'Fluoro) (SEQ ID NO: 46) |
| | 2'-FANA (n) | NH2-TTTGTAGAGGATCAAACTATG ACAACX (X = 2'FANA) (SEQ ID NO: 47) |
| | 2'-FANA (n − 1) | NH2-TTTGTAGAGGATCAAACTATG ACAAXT (X = 2'FANA) (SEQ ID NO: 48) |
| | 2'-FANA (n − 2) | NH2-TTTGTAGAGGATCAAACTATG ACAXCT (X = 2'FANA) (SEQ ID NO: 49) |
| | 2'-Methoxy (n) | NH2-TTTGTAGAGGATCAAACTATG ACAACX (X = 2'OMe) (SEQ ID NO: 50) |
| | 2'-Methoxy (n − 1) | NH2-TTTGTAGAGGATCAAACTATG ACAAXT (X = 2'OMe) (SEQ ID NO: 51) |
| | 2'-Methoxy (n − 2) | NH2-TTTGTAGAGGATCAAACTATG ACAXCT (X = 2'OMe) (SEQ ID NO: 52) |
| | Methyl-phosphonate (n) | NH2-TTTGTAGAGGATCAAACTATG ACAAC(mp)T (SEQ ID NO: 53) |
| | Methyl-phosphonate (n − 1) | NH2-TTTGTAGAGGATCAAACTATG ACAA(mp)CT (SEQ ID NO: 54) |
| | Phosphorothioate (n) | NH2-TTTGTAGAGGATCAAACTATG ACAAC(ps)T-3' (SEQ ID NO: 55) |
| | Phosphorothioate (n − 1) | NH2-TTTGTAGAGGATCAAACTATG ACAA(ps)CT (SEQ ID NO: 56) |

EXAMPLE 14

Evaluation of Modified Double Stranded Adapter Probes for Suppression of Adapter Dimer Formation in a Library Prep Scheme In this experiment, the studies depicted in Example 13 were further expanded to include blunt ended ligation to a double stranded DNA library. In these studies a number of sugar variants for the adapter probes were tested including 2'-fluoro, 2'-methoxy, 2'-FANA, and 2'-hydroxy, as well as a number of modified backbones were tested (phosphorothioate, methylphosphonate) modified constructs (see table in Example 13 for sequences). Each of the double stranded adapter probes were prepared with a 5'-adenylated donor probe. The double stranded modified adapter probe constructs (0.15 µM) and double stranded DNA library (0.01 µM) were incubated in the presence of 1× Reaction Buffer (50 mM Tris-HCl (pH 7.5), 10 mM $MgCl_2$, 10 mM DTT) and 5% PEG 4000, in a reaction volume of 50 µL at 22° C. for 2 hour. The ligation product was analyzed by 10% native polyacrylamide gel electrophoresis. Gel integration reveals at least five of the sugar modified probe constructs and at least one of the backbone modified probe constructs suppressed adapter dimer formation, while allowing for efficient ligation to the double stranded DNA library.

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "a" and "an" and "the" and similar referents in the context of describing the invention (especially in the context of the following claims) are to be construed to cover both the singular and the plural, unless otherwise indicated herein or clearly contradicted by context. The terms "comprising", "having," "including," "containing", etc. shall be read expansively and without limitation (e.g., meaning "including, but not limited to,"). Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention. Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Applicants reserve the right to physically incorporate into this application any and all materials and information from any such articles, patents, patent applications, or other physical and electronic documents.

Other embodiments are set forth within the following claims.

What is claimed is:

1. A method for preparing a nucleic acid library that reduces or inhibits acceptor:donor probe dimer formation, said method comprising: incubating target nucleic acid fragments in a reaction mixture comprising a ligase, a modified donor probe and a modified acceptor probe to prepare a nucleic acid library, wherein said nucleic acid library contains target nucleic acid fragments comprising said modified donor probe ligated to the 3'-terminus and said acceptor probe ligated to the 5'terminus, wherein dimerization of said modified donor probe to said modified acceptor probe is reduced or inhibited and wherein said modified donor probe has the formula 5'-phosphate-$X_{(n1)}$-$Y_{(n2)}$$Z_{(n3)}$-3' or 5'-adenylate-$X_{(n1)}$-$Y_{(n2)}$-$Z_{(n3)}$-3' and said modified acceptor probe has the formula 5'-$D_{(n4)}$-$E_{(n5)}$-$F_{(n6)}$-hydroxy-3', wherein (n2), (n3), (n4), and (n5) are each independently any positive integer, wherein (n1) and (n6) are each independently 1, 2, 3 or 4, wherein X, Y, Z, D, E, and F are nucleotide positions, wherein at least one of $X_{(n1)}$, at least one of $Z_{(n3)}$ and at least one of $F_{(n6)}$ nucleotide positions are modified.

2. The method according to claim 1, wherein the nucleic acid library is an RNA nucleic acid library or a DNA nucleic acid library.

3. The method according to claim 1, wherein said target nucleic acid is an RNA target nucleic acid or a DNA target nucleic acid.

4. The method according to claim 1, wherein said modified donor probe and modified acceptor probe may be single stranded or double stranded polynucleotide probes.

5. The method according to claim 1, wherein said modified donor probe is ligated onto the 3'-terminus of said target nucleic acid fragments.

6. The method according to claim 1, wherein said modified acceptor probe is ligated onto the 5'-terminus of said target nucleic acid fragments.

7. The method according to claim 1, wherein the ligase is a DNA ligase or RNA ligase.

8. The method according to claim 1, wherein said ligase comprises one or more ligases selected from the group consisting of bacteriophage T4 DNA ligase, *Escherichia coli* (*E. coli*) DNA ligase, *Aquifex aeolicus* DNA ligase, *Thermus aquaticus* (Taq) DNA ligase, 9degree N™ DNA ligase, *Methanobacterium thermoautotrophicum* RNA ligase, *Ferroplasma acidiphilum* DNA ligase, Human DNA ligase I, Human DNA ligase II, Human DNA ligase III, Human DNA ligase IV, Vaccinia virus DNA ligase, Chlorella virus DNA ligase, *Pyrococcus furiosis* DNA ligase, *Haloferax volcanii* DNA ligase, *Acidianus ambivalens* DNA ligase, *Archaeoglobus fulgidus* DNA ligase, *Aeropyrum pernix* DNA ligase, *Cenarcheon symbiosum* DNA ligase, *Haloarcula marismortui* DNA ligase, *Ferroplasma acidarmanus* DNA ligase, *Natronomonas pharaosis* DNA ligase, *Haloquadratum walsbyi* DNA ligase, *Halobacterium salinarum* DNA ligase, *Methanosarcina acetivorans* DNA ligase, *Methanosarcina barkeri* DNA ligase, *Methanococcoides burtonii* DNA ligase, *Methanospirillum hungatei* DNA ligase, *Methanocaldococcus jannaschii* DNA ligase, *Methanopyrus kandleri* DNA ligase, *Methanosarcina mazei* DNA ligase, *Methanococcus maripaludis* DNA ligase, *Methanosaeta thermophila* DNA ligase, *Methanosphaera stadtmanae* DNA ligase, *Methanothermobacter thermautotrophicus* DNA ligase, *Nanoarchaeum equitans* DNA ligase, *Pyrococcus abyssi* DNA ligase, *Pyrobaculum aerophilum* DNA ligase, *Pyrococcus horikoshii* DNA ligase, *Picrophilus torridus* DNA ligase, *Sulfolobus acidocaldarius* DNA ligase, *Sulfolobus shibatae* DNA ligase, *Sulfolobus solfataricus* DNA ligase, *Sulfolobus tokodaii* DNA ligase, *Thermoplasma acidophilum* DNA ligase, *Thermococcus fumicolans* DNA ligase, *Thermococcus kodakarensis* DNA ligase, *Thermococcus* sp. NA1 DNA ligase, *Thermoplasma volcanium* DNA ligase, *Staphylococcus aureus* DNA ligase, *Thermus scotoductus* NAD.sup.+-+DNA ligase, T4 RNA ligase, *Staphylococcus*

*aureus* DNA ligase, *Methanobacterium* thermoautotrophicum DNA ligase, *Thermus* species AK16D DNA ligase, *Haemophilus influenzae* DNA ligase, *Thermus thermophilus* DNA ligase, bacteriophage T7 DNA ligase, *Haemophilus influenzae* DNA ligase, *Mycobacterium tuberculosis* DNA ligase, Deinococcus radiodurans RNA ligase, *Methanobacterium thermoautotrophicum* RNA ligase, *Rhodothermus marinus* RNA ligase, *Trypanosoma brucei* RNA ligase, bacteriophage T4 RNA ligase 1, Ampligase, and bacteriophage T4 RNA ligase 2.

9. The method according to claim 1, wherein ligation comprises one or more enzymatic ligation methods selected from the group consisting of a single-stranded ligation, blunt ended ligation, and ligation of cohesive ends.

10. The method according to claim 1, wherein dimerization of said modified donor probe to said modified acceptor probe is reduced or inhibited by about 5% to about 100% relative to dimerization of an unmodified donor probe to an unmodified acceptor probe.

11. The method according to claim 1, wherein dimerization of said modified donor probe to said modified acceptor probe is reduced or inhibited by about 75% to about 100% relative to dimerization of an unmodified donor probe to an unmodified acceptor probe.

12. The method according to claim 1 wherein said modified donor probe and said modified acceptor probe are ligated onto said target nucleic acid fragments with similar efficiency to ligation onto said target nucleic acid fragments with an unmodified donor probe and an unmodified acceptor probe.

13. The method according to claim 12, wherein said efficiency is about 5% to about 200%.

14. The method according to claim 12, wherein said efficiency is about 50% to about 200%.

15. The method according to claim 12, wherein said efficiency is about 50% to about 150%.

16. The method according to claim 1, wherein said modified acceptor has the structure of Formula II:

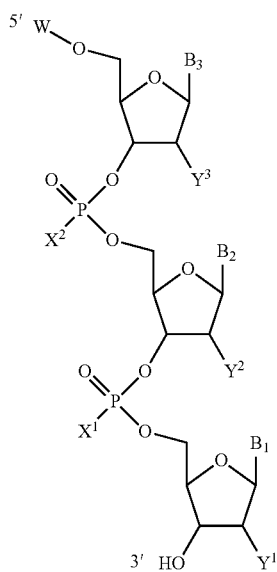

wherein: each $B_1$, $B_2$, and $B_3$ is independently selected from the group consisting of a substituted or non-substituted purine or pyrimidine, any aza or deaza derivative thereof, and any "universal base" or "degenerate base", which is preferably recognizable by a nucleic acid polymerase or ligase; each $X^1$ and $X^2$ is independently selected from the group consisting of OH, SH, $CH_3$, and $OCH_2CH_3$; each $Y^1$, $Y^2$, and $Y^3$ is independently selected from the group consisting of H, F, OH, and $OCH_3$; wherein at least one $X^1$, $X^2$, $Y^1$, $Y^2$ or $Y^3$ is selected from the group consisting of SH, $BH_3^-$, $CH_3$, $OCH_3$, $OCH_2CH_3$ and alkoxy and W is selected from H or an oligonucleotidyl residue.

17. The method according to claim 1, wherein said modified acceptor has the structure of Formula II:

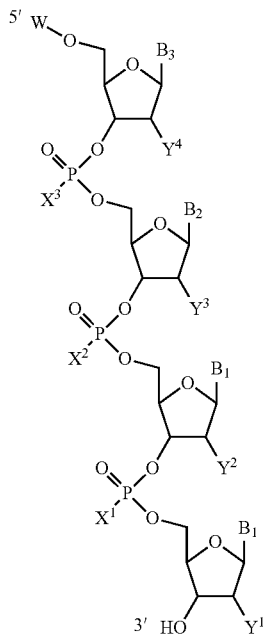

wherein: each $B_1$, $B_2$, and $B_3$ is independently selected from the group consisting of a substituted or non-substituted purine or pyrimidine, any aza or deaza derivative thereof, and any "universal base" or "degenerate base", which is preferably recognizable by a nucleic acid polymerase or ligase; each $X^1$, $X^2$, and $X^3$ is independently selected from the group consisting of OH, SH, $CH_3$, $BH_3^-$, and alkoxy; each $Y^1$, $Y^2$, $Y^3$, and $Y^4$ is independently selected from the group consisting of H, F, OH, $NH_2$ and alkoxy; wherein at least one $X^1$, $X^2$, $X_3$, $Y^1$, $Y^2$, $Y^3$, or $Y^4$ is selected from the group consisting of SH, $BH_3^-$, $CH_3$, $OCH_3$, $OCH_2CH_3$ and W is selected from H or an oligonucleotidyl residue.

18. The method according to claim 1, wherein said modified donor has the structure of Formula III:

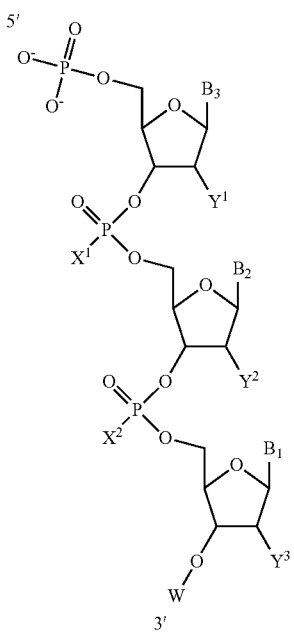

wherein: each $B_1$, $B_2$, and $B_3$ is independently selected from the group consisting of a substituted or non-substituted purine or pyrimidine, any aza or deaza derivative thereof, and any "universal base" or "degenerate base", which is preferably recognizable by a nucleic acid polymerase or ligase; each $X^1$ and $X^2$ is independently selected from the group consisting of OH, SH, $CH_3$, and $OCH_2CH_3$; each $Y^1$, $Y^2$, and $Y^3$ is independently selected from the group consisting of H, F, OH, and $OCH_3$; wherein at least one $X^1$, $X^2$, $Y^1$, $Y^2$ or $Y^3$ is selected from the group consisting of SH, $BH_3^-$, $CH_3$, $OCH_3$, $OCH_2CH_3$ and alkoxy and W is selected from H or an oligonucleotidyl residue.

19. The method according to claim 1, wherein said modified donor has the structure of Formula III:

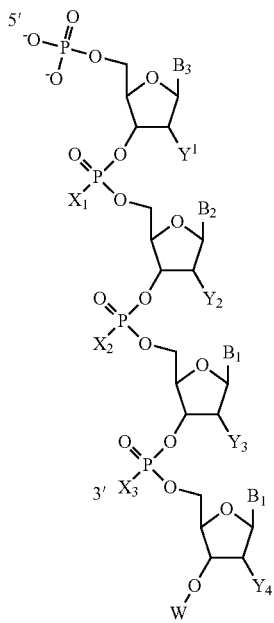

wherein: each $B_1$, $B_2$, and $B_3$ is independently selected from the group consisting of a substituted or non-substituted purine or pyrimidine, any aza or deaza derivative thereof, and any "universal base" or "degenerate base", which is preferably recognizable by a nucleic acid polymerase or ligase; $X^1$, $X^2$, and $X^3$ is independently selected from the group consisting of OH, SH, $CH_3$, $BH_3^-$, and alkoxy; each $Y^1$, $Y^2$, $Y^3$, and $Y^4$ is independently selected from the group consisting of H, F, OH, $NH_2$, and alkoxy; wherein at least one $X^1$, $X^2$, $X^3$, $Y^1$ $Y^2$, $Y^3$ or $Y^4$ is selected from the group consisting of SH, $BH_3^-$, $CH_3$, $OCH_3$, $OCH_2CH_3$ and alkoxy and W is selected from H or an oligonucleotidyl residue.

20. The method according to claim 1, wherein said modified donor has the structure of Formula IV:

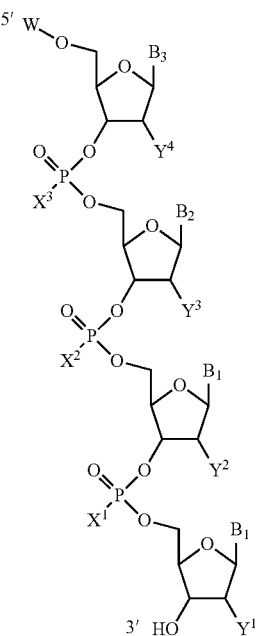

wherein: A is adenine; each $B_1$, $B_2$, and $B_3$ is independently selected from the group consisting of a substituted or non-substituted purine or pyrimidine, any aza or deaza derivative thereof, and any "universal base" or "degenerate base", which is preferably recognizable by a nucleic acid polymerase or ligase; each $X^1$ and $X^2$ is independently selected from the group consisting of OH, SH, $CH_3$, and $OCH_2CH_3$; each $Y^1$, $Y^2$, and $Y^3$ is independently selected from the group consisting of H, F, OH, and $OCH_3$; wherein at least one $X^1$, $X^2$, $Y^1$, $Y^2$ or $Y^3$ is selected from the group consisting of SH, $BH_3^-$, $CH_3$, $OCH_3$, $OCH_2CH_3$ and alkoxy and W is selected from H or an oligonucleotidyl residue.

21. The method according to claim 1, wherein said modified donor has the structure of Formula IV:

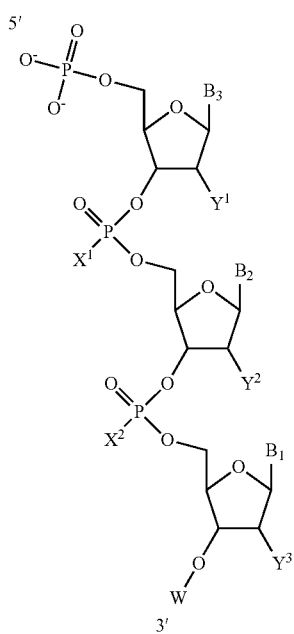

wherein: A is adenine; each $B_1$, $B_2$, and $B_3$ is independently selected from the group consisting of a substituted or non-substituted purine or pyrimidine, any aza or deaza derivative thereof, and any "universal base" or "degenerate base", which is preferably recognizable by a nucleic acid polymerase or ligase; each $X^1$, $X^2$, and $X^3$ is independently selected from the group consisting of OH, SH, $CH_3$, $BH_3^-$, and alkoxy; each $Y^1$, $Y^2$, $Y^3$, and $Y^4$ is independently selected from the group consisting of H, F, OH, $NH_2$, and alkoxy; wherein at least one $X^1$, $X^2$, $X^3$, $Y^1$ $Y^2$, $Y^3$ or $Y^4$ is selected from the group consisting of SH, $BH_3^-$, $CH_3$, $OCH_3$, $OCH_2CH_3$ and alkoxy and W is selected from H or an oligonucleotidyl residue.

22. The method according to claim 1, wherein said modified acceptor probe and said modified donor probe do not prevent ligation of said probes to said target nucleic acid fragments.

23. The method according to claim 1, wherein said modified acceptor probe and said modified donor probe when ligated together to form a probe dimer interfere or prevent replication of said dimer.

24. The method according to claim 1, wherein said modified acceptor probe and said modified donor probe are single stranded nucleic acids.

25. The method according to claim 1, wherein said modified acceptor probe is a double stranded nucleic acid and said modified donor probe is a double stranded nucleic acid.

26. The method according to claim 1, wherein said modified acceptor probe is complementary to said modified donor probe.

27. The method according to claim 1, wherein said complementarity is partial or complete.

* * * * *